(12) United States Patent  (10) Patent No.: US 8,182,983 B2
Hakansson et al.  (45) Date of Patent: May 22, 2012

(54) METHOD FOR DETERMINING IMMUNE SYSTEM AFFECTING COMPOUNDS

(75) Inventors: Leif Hakansson, Vikingstad (SE);
Annika Hakansson, Vikingstad (SE);
Birgitta Clinchy, Ljungsbro (SE)

(73) Assignee: Canimguide Therapeutics AB, Hollviken (SE)

( * ) Notice: Subject to any disclaimer, the term of this patent is extended or adjusted under 35 U.S.C. 154(b) by 0 days.

(21) Appl. No.: 12/822,013

(22) Filed: Jun. 23, 2010

(65) Prior Publication Data

US 2010/0323370 A1  Dec. 23, 2010

Related U.S. Application Data

(63) Continuation of application No. 10/997,985, filed on Nov. 29, 2004, now abandoned, which is a continuation of application No. PCT/SE03/00869, filed on May 27, 2003.

(60) Provisional application No. 60/411,517, filed on Sep. 18, 2002.

(30) Foreign Application Priority Data

May 27, 2002  (SE) ...................................... 0201563

(51) Int. Cl.
*C12Q 1/00*  (2006.01)
(52) U.S. Cl. ............................................. 435/4
(58) Field of Classification Search ......................... None
See application file for complete search history.

(56) References Cited

U.S. PATENT DOCUMENTS

| | | | |
|---|---|---|---|
| 5,284,750 | A | 2/1994 | Silvestrini et al. |
| 6,737,057 | B1 | 5/2004 | Zaghouani |
| 7,960,126 | B2 | 6/2011 | Håkansson et al. |
| 2003/0021792 | A1 | 1/2003 | Roben et al. |
| 2005/0153329 | A1 | 7/2005 | Hakansson et al. |
| 2009/0081649 | A1 | 3/2009 | Håkansson et al. |
| 2011/0262470 | A1 | 10/2011 | Håkansson et al. |
| 2011/0287969 | A1 | 11/2011 | Håkansson et al. |

FOREIGN PATENT DOCUMENTS

| | | |
|---|---|---|
| JP | 62-016430 | 1/1987 |
| JP | 2005089325 | 4/2005 |
| WO | WO 91/09619 | 7/1991 |
| WO | WO 00/28072 | 5/2000 |
| WO | WO 02/30465 | 4/2002 |
| WO | WO 03/099312 | 12/2003 |
| WO | WO 2004/048933 | 6/2004 |
| WO | WO 2006/043891 | 4/2006 |
| WO | WO 2006/110091 | 10/2006 |
| WO | WO 2008/136736 | 11/2008 |

OTHER PUBLICATIONS

Tockman et al (Cancer Res., 1992, 52:2711s-2718s).*
Falconer et al (Cancer, 1995, 75(8): 2077-2082).*
Neuwelt et al (J Neurosurg, 1986, 65(2): Abstract).*
Anderson, et al., "Contributions of the Mac-1 Glycoprotein Family to Adherence-Dependent Granulocyte Functions: Structure-Function Assessments Employing Subunit-Specific Monoclonal Antibodies" The Journal of Immunology, Jul. 1, 1986, pp. 15-27, vol. 137 No. 1.
Bajpai, et al., "Immunomodulating Activity of Analogs of Noninflammatory Fragment 163-171 of Human Interleukin-1 B", Immunopathology, 1998, 38:237-245.
Belluco, et al., "Interleukin-6 Blood Level is Associate With Circulating Carcinoembryonic Antigen and Prognosis in Patients With Colorectal Cancer" Annals of Surgical Oncology, 2000, pp. 133-138, vol. 7, No. 1.
Bhol, et al., "The autoantibodies to alpha 6 beta 4 integrin of patients affected by ocular cicatricial pemphigoid recognize predominantly epitopes within the large cytoplasmic domain of human beta 4." J. Immunol. Sep. 1, 2000;165(5):2824-9.
Brevig, et al., "The recognition of adsorbed and denatured proteins of different topographies by beta2 integrins and effects on leukocyte adhesion and activation." Biomaterials. Jun. 2005;26(16):3039-53.
Brocks et al., "Radioimmunoassay of Laminin in Serum and its Application to Cancer Patients", Clinical Chemistry, 1986, 32/5: 787-791.
Chung, et al., "Serum Interleukin-6 Levels Reflect the Disease Status of Colorectal Cancer" Journal of Curgical Oncology, 2003, pp. 222-226, vol. 83.
Cioli, et al., "A New Protein Antidenaturant Agent, Bindarit, Reduces Secondary Phase of Adjuvant Arthritis in Rats", Journal of Rheumatology 1992 vol. 19, No. 11 pp. 1735-1742.
Clinchy, et al., "Preoperatvie interleukin-6 production by mononuclear blood cells predicts survival after radical surgery for colorectal carcinoma." Cancer. May 1, 2007;109(9):1742-9.
Davis, et al., "The α4β1 integrin can mediate leukocyte adhesion to casein and denatured protein substrates" Journal of Leukocyte Biology, 1997, pp. 318-328, vol. 62.
Davis, George E., "The Mac-1 and p150, 95 β2 Integrins Bind Denatured Proteins to Mediate Leukocyte Cell-Substrate Adhesion" Experimental Cell Research, 1992, pp. 242-252, vol. 200.
Drachenberg et al., "Circulating Levels of Interleukin-6 in Patients with Hormone Refractory Prostate Cancer", The Prostate, 41:127-133 (1999). (Abstract).
Galizia, et al., "Prognostic Significance of Circulating IL-10 and IL-6 Serum Levels in Colon Cancer Patients Undergoing Surgery" Clinical Immunology, Feb. 2002, pp. 169-178, vol. 102, No. 2.
Gruel, et al., "Bypassing tumor-specific and bispecific antiboides: triggering of antitumor immunity by expression of anti-FcγR scFv on cancer cell surface" Gene Therapy (2001) 8: 1721-1728.
Håkansson, A. et al., "Biochemotherapy of metastatic malignant melanoma. Predictive value of tumor-infiltrating lymphocytes" British Journal of Cancer, 2001, pp. 1871-1877, vol. 85, No. 12.

(Continued)

*Primary Examiner* — Sean Aeder
(74) *Attorney, Agent, or Firm* — Knobbe, Martens, Olson & Bear, LLP

(57) ABSTRACT

The present invention relates to a method for increasing efficacy and/or possibility of therapeutic treatment of cancer, wherein any dys-regulatory mechanism, including inducing factor/s, of the production of immunoregulatory substances, including one or more cytokines, including IL-1β, IL-1Ra, IL-6, IL-10, IL-17, TNF-α, and others, is therapeutically controlled to minimise pathological production of such immunoregulatory substances, to enhance the therapeutic control of a malignant tumour in a subject suffering from a cancer, a method for analysing dys-regulatory mechanism controlling substances, kit for such analysis, use of certain compounds for preparing pharmaceutical preparations, and pharmaceutical preparations.

8 Claims, 22 Drawing Sheets

OTHER PUBLICATIONS

Håkansson, A. et al., "Tumor-infiltrating lymphocytes in metastatic malignant melanoma and response to interferon alpha treatment" British Journal of Cancer, 1996, pp. 670-676, vol. 74.

Hauptman, et al., "Antibodies to human albumin in cirrhotic sera." J. Clin Invest. Jul. 1974;54(1):122-7.

Kaminska, et al., "Clinical Significance of Serum Cytokine Measurements in Untreated Colorectal Cancer Patients: Soluble Tumor Necrosis Factor Receptor Type I—An Independent Prognostic Factor" Tumor Biology, 2005, pp. 186-194, vol. 26.

Kaminska, et al., "CRP, TNFα, IL-1ra, IL-6, IL-8 and IL-10 in Blood Serum of Colorectal Cancer Patients" Pathology Oncology Research, 2000, pp. 38-41, vol. 6, No. 1.

Kinoshita, et al., "Serum Interleukin-6 Level Reflects the Tumor Proliferative Activity in Patients with Colorectal Carcinoma" Cancer, Jun. 15, 2009, pp. 2526-2531, vol. 85, No. 12.

Kuntz, "Structure-based strategies for drug design and discovery." Science. 1992 257(5073):1078-1082.

Maccio et al., "High Serum Levels of Soluble IL-2 Receptor, Cytokines, and C Reactive Protein Correlate with Impairment of T Cell Response in Patients with Advanced Epithelial Ovarian Cancer", Gynecological Oncology, 1998, 69: 248-252.

Miller, et al., "Ligand binding to proteins: the binding landscape model." Protein Sci. Oct. 1997;6(10):2166-79.

Nikiteas, et al., "Serum IL-6, TNFα and CRP levels in Greek colorectal cancer patients: Prognostic implications" World Journal of Gastroenterology, 2005, pp. 1639-1643, vol. 11.

Oyama, et al., "Autoantibodies to extracellular matrix protein 1 in lichen sclerosus." Lancet. Jul. 12, 2003;362(9378):118-23.

Piancatelli, et al., "Local Expression of Cytokines in Human Colorectal Carcinoma: Evidence of Specific Interleukin-6 Gene Expression", Journal of Immunotherapy, 1999, vol. 22, p. 25-32.

Rich, et al., "Elevated Serum Cytokines Correlated with Altered Behavior, Serum Cortisol Rhythm, and Dampened 24-Hour Rest-Activity Patterns in Patients with Metastatic Colorectal Cancer" Clinical Cancer Research, Mar. 1, 2005, pp. 1757-1764, vol. 11.

Rouard, et al, "Fc Receptors as Targets for Immunotherapy" Intern. Rev. Immunol. (1997) 16: 147-185.

Ruka, et al., "Alterations of routine blood tests in adult patients with soft tissue sarcomas: Relationships to cytokine serum levels and prognostic significance" Annals of Oncology (2001) 12: 1423-1432.

Saso, et al., "Inhibition of Protein Denaturation by Fatty Acits, Bile Salts and Other Natural Substances: A New Hypothesis for the Mechanism of Action of Fish Oil in Rheumatic Diseases" Japan Journal of Pharmacology, 1999, vol. 79 pp. 89-99.

Siedlar, et al., "Depressed Tumor Necrosis Factor Alpha and Interleukin-12p40 Production by Peripheral Blood Mononuclear Cells of Gastric Cancer Patients: Associate with IL-IR-Associated Kinase-1 Protein Expression and Disease State", Internation Journal Cancer, 2005, vol. 114, p. 144-152.

Tamura, et al., "Anti-albumin antibodies in sera of patients with liver disease." Gastroenterol Jpn. Oct. 1982;17(5):469-75.

Ueda, et al., "Serum levels of cytokines in patients with colorectal cancer: Possible involvement of interleukin-6 and interleukin-8 in hematogenous metastasis" J. Gastroenterol. (1994) 29: 423-429.

Wood et al., "The Clinical Significance of the Pattern of Elevated Serum Carcinoembryonic Antigen (CEA) Levels in Recurrent Colorectal Cancer", BR. J. Surg., 1980, 67(1): 46-48 (Abstract).

Wu et al., "Serum Interleukin-6 Levels Reflect Disease Status of Gastric Cancer", American Journal of Gastroenterology, 1996, 91(7): 1417-1422 (Abstract).

International Search Report, dated Nov. 4, 2003, issued in PCT/SE03/00869.

International Search Report, dated Feb. 6, 2006, issued in PCT/SE05/001582.

International Search Report, dated Jul. 13, 2006, issued in PCT/SE06/000440.

International Preliminary Report on Patentability, date Dec. 4, 2006, issued in PCT/SE06/000440.

International Search Report, dated Jan. 5, 2009, issued in PCT/SE08/000314.

Shacter E. et al. "Stimuation of interleukin-6 and prostaglandin E2 secretion from peritoneal macrophages by polymers of albumin", Blood, 82:2853-2864 (1993). 13 pages.

Canadian Application No. 2526950, filed May 27, 2003.

* cited by examiner

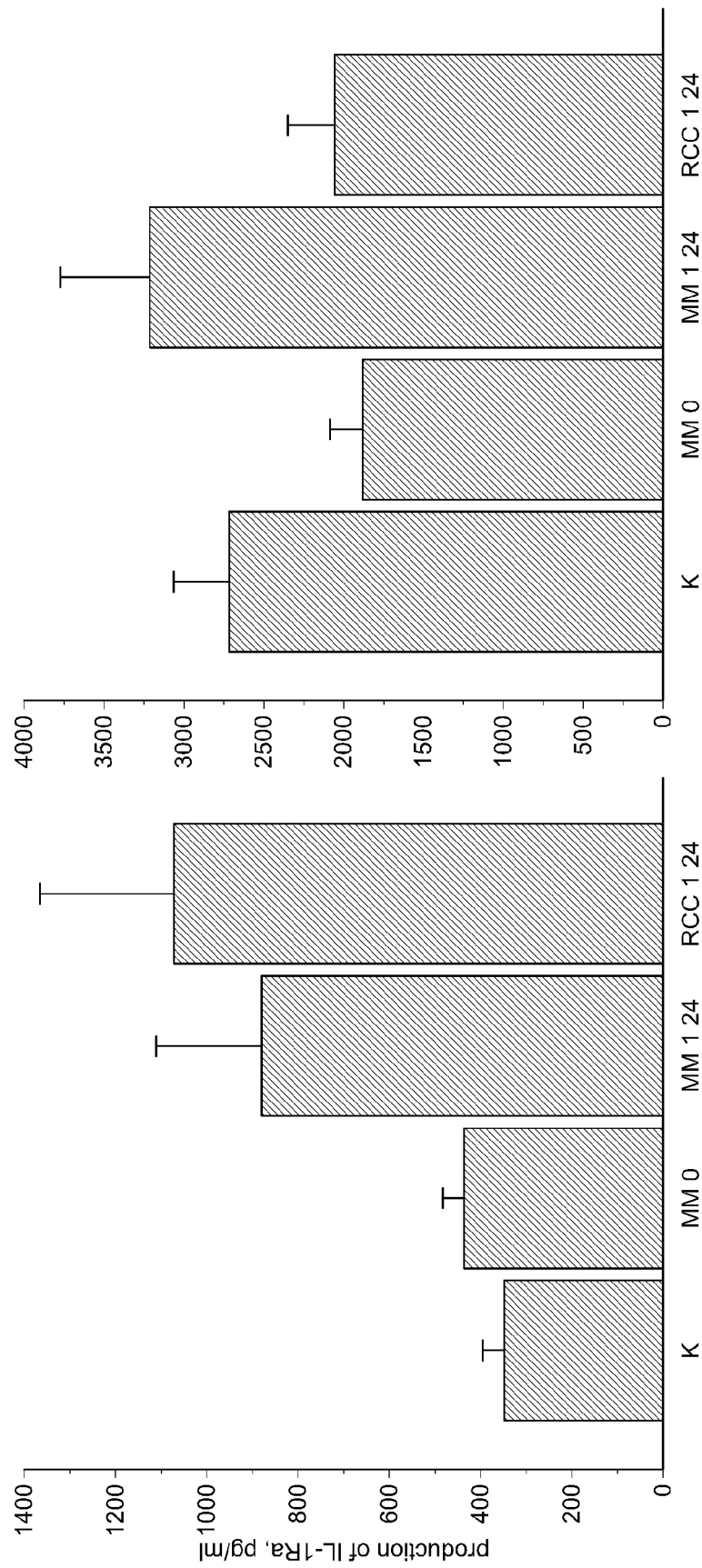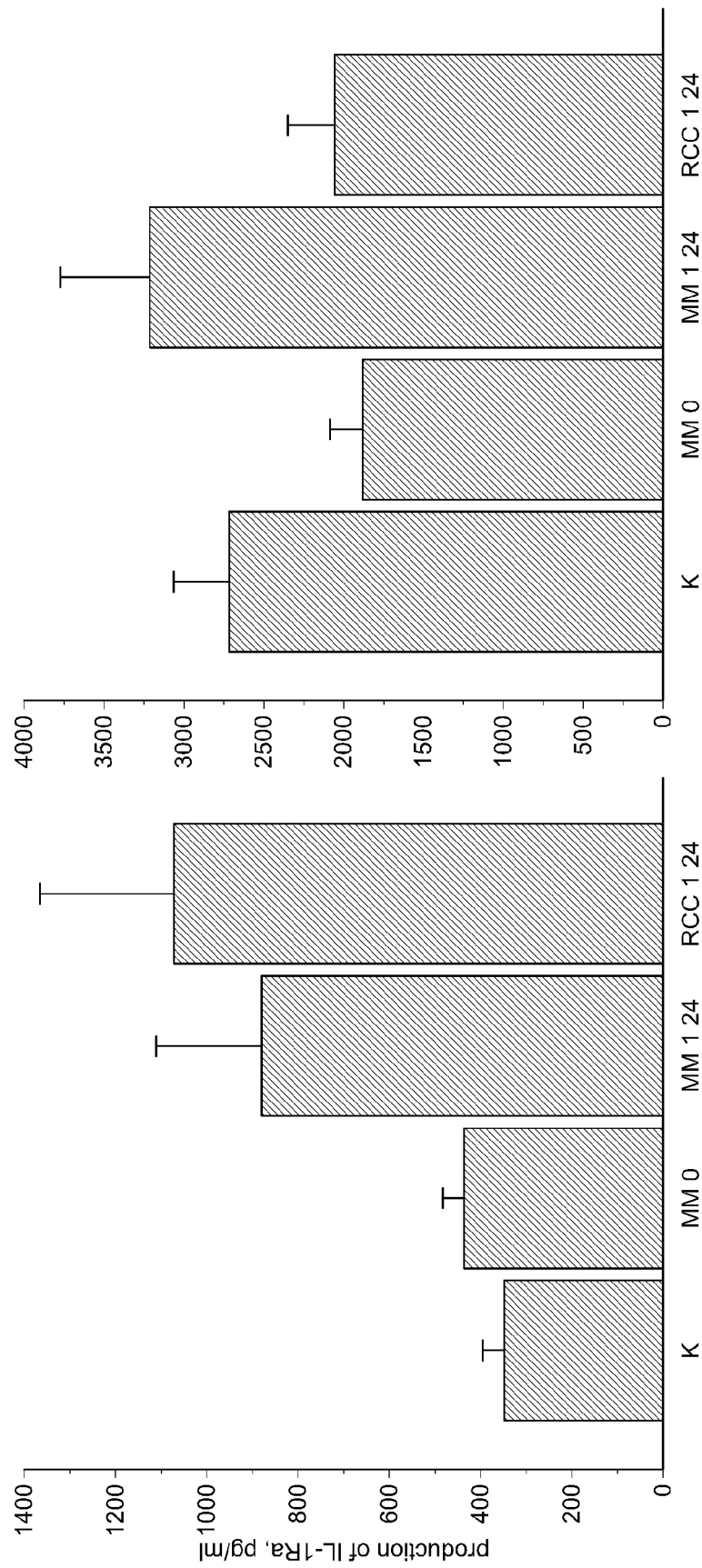
FIG. 3A
FIG. 3B

METHOD FOR DETERMINING IMMUNE SYSTEM AFFECTING COMPOUNDS

CROSS REFERENCE TO RELATED APPLICATIONS

This application is a continuation of and claims the benefit of priority to U.S. patent application Ser. No. 10/997,985, filed Nov. 29, 2004, which is a continuation of and claims the benefit of priority to PCT International Application Number PCT/SE03/00869, filed May 27, 2003, designating the United States of America and published in the English language, which is an International Application of and claims the benefit of priority to U.S. Provisional Patent Application No. 60/411,517, filed Sep. 18, 2002, and Swedish National Application No. 0201563-4, filed May 27, 2002. The disclosures of the above-referenced applications are hereby expressly incorporated by reference in their entireties.

TECHNICAL FIELD

The present invention relates to method for treating cancer, method for determining immunoregulatory substances, kit for carrying out said determination, use of certain compounds for preparation of pharmaceutical compositions, as well as pharmaceutical compositions.

BACKGROUND OF THE INVENTION

Evidence of the occurrence of immunogenic tumours among a majority is of different types of human cancers is increasing, e.g., specific cytotoxic T-lymphocytes, CTLs, are found in the blood of cancer patients, antibodies against tumour associated antigens have been identified, inflammatory cells are infiltrating the tumours, there is often a correlation between these cells and prognosis or response to immunotherapy and an immune mediated anti-tumour reactivity has been demonstrated after therapy.

The function of immune cells in cancer patients is, however, often impaired. Generally this is more pronounced in tumour infiltrating mononuclear cells (Vose et al., 1977), TIMC, than in cells obtained from peripheral blood. It has for example repeatedly been demonstrated that the proliferative response to mitogens, such as phytohemagglutinin (PHA) or concanavalin A (ConA), is inhibited, natural killer cell (NK-cell) activity and cytotoxic activity of CTLs are reduced as is the maturation and function of dendritic cells and the immune balance seems to be directed to a T-helper 2 situation (Pawelec et al. 2000).

Immunosuppression of TIMC can, however, at least to some extent be overcome, either by washing, preincubation before stimulation, or culturing in interleukin-2. Amazingly, the down-regulation of the immune system, which relates to cancer, does not result in a seriously increased incidence of infectious diseases in these patients.

The demonstration of concomitant immunity shows the existence of regional immunosuppression in the absence of systemic suppression, indicating a regional—systemic gradient of immunosuppression (North, 1985). Systemic immunosuppression can thus be regarded as a systemic dissemination, or "spill-over" of intra-tumoural suppression.

Extracts or supernatants from tumours are often immunosuppressive (Sulitzeanu, 1993). Several factors have been suggested to mediate this suppression, e.g., TGF-$\beta$, PGE$_2$, IL-10, IL-4 and others, either being produced by the tumour cells as such or by tumour-infiltrating lymphocytes (TIL) or tumour associated macrophages (TAM) (e.g. Ménétrier-Caux et al., 1999; Heimdal et al., 2000; Heimdal et al., 2001). However, no fundamental mechanism has been identified so far (Mocellin, 2001).

The immunosuppression of cancer patients described above often involves an ongoing systemic, chronic inflammation with an increased production of cytokines, in particular IL-6 and TNF-$\alpha$seems to be important mediators in this process. This results in a paraneoplastic syndrome with a poor performance status—impaired general condition, which is characterized by anorexia, fatigue, subfebrility and distortion of various biochemical laboratory parameters, e.g., low haemoglobin concentration, high numbers of platelets, increased numbers of blood monocytes, increased concentration of acute phase reactants, increased c-reactive protein (CRP) and erythrocyte sedimentation rate (ESR) and other factors (Barton™, 2001; Blay et al., 1992; Blay et al., 1997; Gadducci et al., 2001; Walther et al., 1998). This condition is correlated to the tumour burden of the patient, being worse in more advanced disease. In the clinical situation, attempts are often made to ameliorate the poor general condition of these patients by corticosteroid treatment.

Chronic inflammatory reactions in cancer patients often result in a poor response to the immunotherapy (Blay et al. 1992; Deehan et al., 1994; Lissoni et al., 1999; Tartour et al., 1996). There are some animal and human reports on the importance of the immune status of tumour bearers for response to cytotoxic treatment/chemotherapy or radiotherapy. (Goldin et al., 1980; Milas et al., 2001)

Immunostimulatory treatment of the dysregulated immune system of cancer patients might be counter-productive. If the immune system in cancer is directed to down-regulation of the chronic inflammatory reaction there is a risk that further therapeutic immunostimulation will enhance the immunosuppression and thereby further down-regulate the immune reactivity against the tumour cells. The strategy should therefore be to eliminate mediators of immunosuppression before the immune system is stimulated.

In developing immunotherapeutic strategies in cancer several critical steps, of major importance for initiation and maintenance of immune mediated anti-tumour reactivity, have to be considered.

For initiation of an immune response the tumour has to be recognised as non-self. The initial induction of an immune response to tumour associated antigens takes place at an early stage of the malignant disease while the tumour burden is still reasonably small and tumour related immunosuppressive mechanisms are not yet activated. In this situation the immune reactivity to the tumour is beneficial and control the malignant growth for some time.

In order to get an immune response a proper interaction between antigen presenting cells (APCs) and lymphocytes has to take place with a well-orchestrated production of cytokines and expression/interaction of co-stimulatory molecules.

In cancer patients with macroscopic, progressive tumour a different situation prevails. The anti-tumour immune reactivity has been suppressed. In a small subset of patients the immunostimulatory therapeutic strategies, which are available, e.g., interferons, interleukins, vaccination, can overcome this immunosuppression, which results in objective tumour regression in only about 10-15 percent of the patients and short-lasting minor regressions in some more. The poor efficacy of such treatment strategy depends on the occurrence of non-immunogenic tumours, serious immunosuppression (which can not be overcome by current therapeutic methods) and down-regulation of the immune reactivity during immunotherapy. Tumour related suppressor substances might interfere with these mechanisms during development of immunosuppression. Immune mediated anti-tumour reactivity also seems to be down regulated via interaction with FcR, in particular FcγR.

Tumour related immunosuppression takes place at four levels: Activation, recruitment of effector cells to the tumour, migration of these cells from stromal areas close to the tumour cells and cytotoxic activity.

Mechanisms by which malignant tumours can down-regulate the immune system are tumour derived non-immunogenic substances with suppressor activity;
well-characterized immunomodulating substances, cytokines, e.g., transforming growth factor beta (TGF-β), IL-10, as well as $PGE_2$,
tumour associated antigen (TAA) resulting in antigenic overload, production of antibody and immunocomplex (IC);
serum blocking factors, which are probably related to immune complexes, cross-linking Fc receptor (FcγR);
proteolytic fragments from tumour substances, e.g., extracellular matrix (ECM);
T-helper 1/T helper 2 (Th1/Th2) balance Stimulation of the inhibited immune reactivity to the tumour can be achieved using several therapeutic strategies. However, several function parameters are down-regulated during the treatment, particularly in tumour areas with the most pronounced regressive changes.

It would thus be of great importance in the treatment of cancer patients to identify the mechanisms by which the immune system is dys-regulated and to develop proper diagnostic tests of this condition. The ultimate goal is then, based on these tests to find measures to treat, eliminate the immunosuppression, and thereby improve the general condition of cancer patients and increase the therapeutic efficacy in cancer.

SUMMARY OF THE PRESENT INVENTION

It has been found that efficacy and possibility of therapeutic treatment of cancer can be increased, whereby any dysregulatory mechanism of the production of immunoregulatory substances, is therapeutically controlled to minimise pathological production of such immunoregulatory substances, to enhance the therapeutic control of a malignant tumour in a subject suffering from a cancer and the chronic inflammatory reaction in cancer patients which latter reaction plays an important role in cancer therapy.

The object of the present invention is thus to obtain a method for increasing the possibility of treating cancer, a method for determining factor(-s) related to prognosis and allowing prediction and monitoring therapy of cancer, and a kit for determining such factor(-s), use of substances to prepare pharmaceutical compositions, as well as pharmaceutical compositions.

DESCRIPTION OF THE PRESENT INVENTION

It has now surprisingly been found a method for increasing efficacy and possibility of therapeutic treatment of cancer, wherein any regulatory mechanism, including inducing factor/s, of the production of immunoregulatory substances, including IL-1β, IL-1Ra, IL-6, IL-10, IL-17, TNF-α, and others, is therapeutically controlled to minimise pathological production of such immunosuppressive immunoregulatory substances or to stimulate the production of immunosupportive immunoregulatory substances to enhance the performance status of a patient and/or to enhance the therapeutic control of a malignant tumour in a subject suffering from a cancer.

According to a preferred embodiment any dysregulatory mechanism of immunoregulatory substances, including one or more cytokines, including IL-1β, IL-1Ra, IL-6, IL-10, IL-17, TNF-α and others, production in a patient suffering from cancer is modulated by therapeutically treating the patient to provide a FcR modulation by administering a therapeutically effective amount of a FcR modulating agent.

According to another preferred embodiment any dysregulatory mechanism of immunoregulatory substances, including one or more cytokines, including IL-1β, IL-1Ra, IL-6, IL-10, IL-17, TNF-α, and others, production in a patient suffering from cancer is modulated by therapeutically treating the patient to provide a FcR/FcγR modulation by administering a therapeutically effective amount of a FcR/FcγR blocking agent.

According to another preferred embodiment any dysregulatory mechanism of immunoregulatory substances, including one or more cytokines, including IL-1β, IL-1Ra, IL-6, IL-10, IL-17, TNF-α, and others, production in a patient suffering from cancer is modulated by therapeutically treating the patient to provide a FcR/FcγR modulation by administering a therapeutically effective amount of a FcR/FcγR is cross-linking agent.

According to another preferred embodiment blocking or cross-linking of FcR is carried out using a therapeutically active amount of at least one immunoglobulin, FcR antibodies or fragments of antibodies or synthetic constructs including peptides directed to FcR.

According to another preferred embodiment at least one FcR-modulating substance minimising production of interleukin-1 receptor antagonist is administered in a therapeutically effective amount.

According to another preferred embodiment wherein the modulation is carried out by blocking FcR by administering F(ab), or F(ab')2-fragments.

According to another preferred embodiment the modulating substance is a soluble receptor, fragment, peptide or synthetic construct directed to the Fc-part of immunoglobulins.

According to another preferred embodiment FcγR I, FcγR II and/or FcγR III is modulated to stimulate IL-2 stimulation of clonal expansion of lymphocytes.

According to another preferred embodiment any compound blocking the production or biological activity of a factor inducing pathological production of any dysregulatory mechanism of immunoregulatory substances, including one or more cytokines, including IL-1β, IL-1Ra, IL-6, IL-10, IL-17, TNF-α, and others, production, is administered in a therapeutically effective amount.

According to another preferred embodiment the blocking compound is a receptor blocking compound.

According to another preferred embodiment the blocking compound is a monoclonal antibody, fragments thereof, peptides or synthetic constructs.

According to another preferred embodiment a compound having the ability of inhibiting the activation or activity of enzymes generating immunomodulatory fragments is administered in a therapeutically effective amount.

According to another preferred embodiment the inhibiting compound is a monoclonal antibody, an anti-integrin antibody, peptides and/or synthetic constructs.

According to another preferred embodiment the modulating substance is an enzyme inhibitor.

According to another preferred embodiment the inhibiting compound is a matrix metalloproteinase inhibitor.

According to another preferred embodiment any compound blocking the factor inducing IL-6 production is administered in a therapeutically effective amount.

According to another preferred embodiment any compound blocking the factor inducing IL-1β production is administered in a therapeutically effective amount.

According to another preferred embodiment any compound blocking the factor inducing IL-10 production is administered in a therapeutically effective amount.

According to another preferred embodiment any compound blocking the factor inducing TNF-α production is administered in a therapeutically effective amount.

According to another preferred embodiment any compound blocking the factor inducing IL-1Ra production is administered in a therapeutically effective amount.

According to another preferred embodiment monoclonal antibodies directed to enzymes generating immunomodulatory fragments are administered in a therapeutically effective amount.

According to another preferred embodiment at least one anti-integrin antibody, peptide or construct is administered in a therapeutically effective amount.

Further preferred embodiments are as follows.

According to another preferred embodiment blocking cross-linking of FcR is carried out using a therapeutically active amount of FcR antibodies or fragments of monoclonal antibodies directed to FcR, preferably the FcR cross-linking is obtained by administering a therapeutically effective amount of at least one immunoglobulin, more preferably the FcR cross-linking is obtained by administering a therapeutically effective amount of IgG or complex bound IgG, and/or the FcR cross-linking is obtained by administering a therapeutically effective amount of IgA or complex bound IgA.

According to a further preferred embodiment a therapeutically effective amount of Fc part of at least one immunoglobulin is administered, preferably a therapeutically effective amount of Fc part of IgG or is complex bound IgG is administered, and/or a therapeutically effective amount of Fc part of IgA or complex bound IgA is administered.

According to a further preferred embodiment any cross-linking of FcγR I, FcγR II and/or FcγR III is carried out.

According to a further preferred embodiment FcR is down-regulated using an inhibitor of its expression.

According to another, further preferred embodiment blocking of FcγR is carried out by administering a therapeutically effective amount of anti-FcγR I antibodies.

According to another preferred embodiment at least one FcR-blocking substance minimising production of interleukin-1 receptor antagonist is administered in an amount necessary to block the activity of interleukin-1.

A further aspect of the invention includes a method for analysing the amount and/or certain pattern of dysregulatory mechanism substances, including their mRNA, including any inducing factor, inducing the production of immunoregulatory substances, including one or more cytokines, including IL-1β, IL-1Ra, IL-6, IL-10, IL-17, TNF-α, and others, whereby the amount of such dysregulatory mechanism substances is determined in a tissue sample, whereby the prognosis of a subject suffering from cancer can be determined and/or the therapeutic efficacy of any anti-cancer treatment can be predicted and monitored.

According to a preferred embodiment tissue is whole blood, serum, plasma, lymphatic fluid, saliva, urine, faeces, ascites, pleural effusion, pus, as well as any tissue, including inflammatory cells.

According to another preferred embodiment any compound having the ability of inhibiting the activation or activity of enzymes generating fragments of intra-tumoural tissue are determined.

According to another preferred embodiment any fragment or new epitopes generated by the activity of intratumoral enzymes is determined in any tissue from a cancer patient.

According to another preferred embodiment the activity of any compound having the ability of inhibiting the activation or activity of enzymes generating fragments is monitored by determining these fragments or new epitopes exposed by the enzymatic activity in any tissue from a cancer patient.

According to another preferred embodiment the inhibiting compound is a matrix metalloproteinase inhibitor.

According to another preferred embodiment any compound blocking production or biological activity of a factor inducing pathological production of any dys-regulatory mechanism of immunoregulatory substances, including one or more cytokines, including IL-1β, IL-1Ra, IL-6, IL-10, IL-17, TNF-α, and others, production, is determined.

According to another preferred embodiment the amount of any inducing factor or mRNA thereof inducing the production of immunoregulatory substances, including one or more cytokines including IL-1β, IL-1Ra, IL-6, IL-10, IL-17, TNF-α and others, found in tissue, is determined by determining the production of immunoregulatory substances, including cytokines, including, including IL-1Ra, IL-6, IL-1β and/or TNF-α and others produced by PBMC after exposure to these factors.

According to another preferred embodiment samples are obtained in a way, including tubes and syringes, not binding or inactivating immunoregulatory substances, including inducing factors.

According to another preferred embodiment the amount of any inducing factor inducing the production of immunoregulatory substances, including one or more cytokines including IL-1β, IL-1Ra, IL-6, IL-10, IL-17, TNF-α, and others, is determined directly.

According to another preferred embodiment the amount/occurrence of any cell bound factor inducing the production of immunoregulatory substances, including IL-1β, IL-1Ra, IL-6, IL-10, IL-17, TNF-α, and others, is determined.

According to another preferred embodiment the amount of any urine present inducing factor inducing the production of immunoregulatory substances, including IL-1β, IL-1Ra, IL-6, IL-10, IL-17, TNF-α, and others, is determined by using an urine dip stick containing binding substance/s binding said inducing factor and/or colour developing reagents to said inducing factor.

According to another preferred embodiment the amount of cell bound immune complexes, CBIC, is determined.

According to another preferred embodiment peripheral blood mononuclear cells PBMC, being positive for any immunoglobulin staining are determined.

According to another preferred embodiment PBMC being positive for IgG staining are determined.

According to another preferred embodiment PBMC being positive for IgA staining are determined.

According to another preferred embodiment FcR positive to any immunoglobulin staining is determined, such positive for IgG staining and/or IgA staining.

According to another preferred embodiment the production of $O_2^-$ is determined.

According to another preferred embodiment down-regulation of the chain of TCR is determined.

According to another, further preferred embodiment fine needle biopsy TIMC (tumour infiltrating mononuclear cell) being positive to immunoglobulins are determined.

According to another preferred embodiment fine needle biopsy TIMC being positive to IgG are determined.

According to a further preferred embodiment fine needle biopsy TIMC being positive to IgA are determined.

According to another preferred embodiment IL-1Ra is determined.

According to another preferred embodiment down-regulation of CD28 on CD4+ and/or CD8+ lymphocytes is determined.

According to another preferred embodiment down-regulation of CD80 and/or CD86 is determined.

According to another preferred embodiment determination of any other modulation of other immunoregulatory substances is made.

According to another preferred embodiment the content of IL-1β, IL-1Ra, IL-6, IL-10, IL-17, and/or TNF-α, is determined by using an assay, to determine the amount of an inducing factor inducing IL-1β, IL-1Ra, IL-6, IL-10, IL-17, TNF-α, and others, activity.

According to another preferred embodiment the assay utilises any tissue and the determinations are made using any immuno-cyto-histochemical method, any immunoassay including, ELISA, Elispot, RIA and others any blotting technique, including Western blotting, Southern blotting and others, any bioassay, any tissue culture technique, RT-PCR, flow cytometry, cytometric bead array, DNA microarray and/or proteomics.

According to another preferred embodiment dys-regulatory mechanism substances in tissue from cancer patients, which substances suppress the immune mediated systemic protection resulting in establishment of micrometastases, are identified.

According to another preferred embodiment patients suffering from potential risk are candidates for adjuvant treatment.

According to another preferred embodiment the invention encompasses specific staining methods for IgG in PBMC or biopsies, whereby a first method for determining IgG/IC complexes using a staining, is characterized in that peripheral blood mononuclear cells are separated by centrifugation and spun onto microscope slides; the cells are pre-hydrated using Hank's balanced solution and Hepes solution and human serum albumin, are fixed in phosphate-buffered paraformaldehyde supplemented with glucose, are incubated with biotinylated protein G, followed by incubation with alkaline phosphatase-labelled streptavidin, are incubated in alkaline phosphatase substrate in Tris buffer with dimethylformamide, levamisole and Fast-Red TR salt, are counterstained in Mayer's haematoxylin and mounted in Glycergel; or alternatively, after fixation and a washing in Hank's balance solution containing goat serum, the cells are blocked in goat serum and are incubated with mouse anti-human IgG Monoclonal antibody, are incubated with Envision, are then incubated with the alkaline phosphatase substrate, are then counterstained in Mayer's haematoxylin and are mounted in Glycergel;
and a second method for determining IgG/IC complexes using a staining, is characterized in that a tissue sample is fixed using phosphate-buffered paraformaldehyde in the presence of glucose, is treated with Hank's balanced solution and Hepes solution, incubated with primary antibody, mouse IgG1 anti-human CD3, followed by incubation with goat-anti-mouse immunoglobulin, followed by incubation with PAP mouse monoclonal antibody; using 3,3-Diaminobenzidine as a substrate resulting in a brown colour, whereby the presence of IgG is then identified using biotinylated protein G by incubation; followed by incubation with alkaline phosphatase-labelled streptavidin followed by incubation with alkaline phosphatase substrate, dimethylformamide, levamisole, and Fast-Red salt, the cells are then counterstained in Mayer's haematoxylin and mounted in Glycergel producing a bright red staining for IgG, whereby double-stained cells appeared as red-brown A further aspect of the invention includes a kit for quantitative and/or qualitative analysis of amount of and/or certain pattern of dys-regulatory factor and/or factors inducing the production and/or activation of immunoregulatory substances, whereby prognosis of cancer can be determined and the therapeutic efficacy of any anti-cancer treatment can be predicted and monitored, comprising an indicator for the presence of said dys-regulatory factor/s including inducing factor/s.

According to another preferred embodiment the kit comprises an indicator for the presence of any factor inducing immunoregulatory substances, including cytokines, including IL-1β, IL-1Ra, IL-6, IL-10, IL-17, and/or TNF-α, and others, activity.

According to another preferred embodiment the kit comprises a nutrient for peripheral blood mononuclear cells and a determinant for inducing factor for inducing immunoregulatory substances including inducing factors of IL-1β, IL-1Ra, IL-6, IL-10, IL-17, TNF-α, and others.

According to another preferred embodiment it comprises a urine dip stick comprising binding substance/s and/or colour developing reagents.

According to another preferred embodiment the kit comprises determinants for enzymatic degradation products of tumour substances/extra cellular matrix, ECM.

According to another preferred embodiment a matrix metalloproteinase inhibitor is monitored.

According to another preferred embodiment the kit comprises a determinant for dys-regulatory substances in tissue from cancer patients, which substances suppress the immune mediated systemic protection resulting in the establishment of micrometastases.

According to another preferred embodiment the amount of cell bound immune complexes, CBIC, is determined.

A still further aspect of the invention includes use of at least one regulatory mechanism controlling factor of at least one immunoregulatory substance, including inducing factor of the production or biological activity of immunoregulatory substances including cytokines, including IL-1β, IL-1Ra, IL-6, IL-10, IL-17, TNF-α, and others, for the production of a pharmaceutical preparation to be used for therapeutic control and for minimisation of pathological production of immunosuppressive immunoregulatory substances, including IL-1β, IL-1Ra, IL-6, IL-10, IL-17, and/or TNF-α, and others or to stimulate production of immunosupportive immunoregulatory substances in a patient suffering from a cancer and to enhance the efficacy and/or possibility of therapeutic treatment of cancer or modulation of dys-regulatory factors to enhance performance status.

According to another preferred embodiment a FcR modulating agent is used in the manufacture of a pharmaceutical preparation for controlling immunoregulatory substances, including one or more cytokines, including IL-1β, IL-1Ra, IL-6, IL-10, IL-17, and/or TNF-α, and others, production in a patient suffering from cancer by therapeutically modulating FcR activity.

According to another preferred embodiment a FcR modulating agent is used in the manufacture of a pharmaceutical preparation for controlling immunoregulatory substances, including one or more cytokines, including IL-1β, IL-1Ra, IL-6, IL-10, IL-17, TNF-α, and others, production in a patient suffering from cancer is modulated by therapeutically blocking FcR/FcγR activity.

According to another preferred embodiment a FcR modulating agent is used in the manufacture of a pharmaceutical preparation for controlling immunoregulatory substances, including one or more cytokines, including IL-1β, IL-1Ra, IL-6, IL-10, IL-17, TNF-α, and others, production in a patient suffering from cancer is modulated by cross-linking FcR/FcγR activity.

According to another preferred embodiment at least one immunoglobulin, FcR antibodies or fragments of antibodies or synthetic constructs including peptides directed to FcR is used in the manufacture of a pharmaceutical preparation for blocking or cross-linking FcR cross-linking.

According to another preferred embodiment an agent modulating FcγR I, FcγR II and/or FcγR III used to stimulate IL-2 stimulation of clonal expansion of lymphocytes is used in the manufacture of a pharmaceutical preparation.

According to another preferred embodiment FcR antibodies or fragments of FcR antibodies directed to FcR is used in the manufacture of a pharmaceutical preparation for blocking cross-linking of FcR.

According to another preferred embodiment anti-FcγR I, FcγR II and/or FcγR III antibodies is used in the manufacture of a pharmaceutical preparation for blocking of FcγR.

According to another preferred embodiment a compound being able to down-regulate the expression of FcR is used in the manufacture of a pharmaceutical preparation for down-regulating FcR.

According to another preferred embodiment at least one FcR-blocking substance minimising production of interleukin-1 receptor antagonist is used in the manufacture of a pharmaceutical preparation for blocking the activity of interleukin-1.

According to another preferred embodiment at least one FcR-modulating soluble receptor, fragment, peptide or synthetic construct directed to the Fc-part of immunoglobulins is used in the manufacture of a pharmaceutical preparation.

According to another preferred embodiment at least one FcR-modulating enzyme inhibitor is used in the manufacture of a pharmaceutical preparation.

According to another preferred embodiment at least one FcR-inhibiting matrix metalloproteinase inhibitor is used in the manufacture of a pharmaceutical preparation.

According to another preferred embodiment any compound blocking production or biological activity of any factor inducing pathological production of one or more cytokines is used in the manufacture of a pharmaceutical preparation for blocking a factor inducing pathological production of such cytokines.

According to another preferred embodiment any factor inducing IL-6 production is used in the manufacture of a pharmaceutical preparation for blocking a factor inducing pathological production of such cytokine.

According to another preferred embodiment any factor inducing IL-1β production is used in the manufacture of a pharmaceutical preparation for blocking a factor inducing pathological production of such cytokine.

According to another preferred embodiment any factor inducing IL-10 production is used in the manufacture of a pharmaceutical preparation for blocking a factor inducing pathological production of such cytokine.

According to another preferred embodiment any factor inducing IL-17 production is used in the manufacture of a pharmaceutical preparation for blocking a factor inducing pathological production of such cytokine.

According to another preferred embodiment any factor inducing TNF-α production is used in the manufacture of a pharmaceutical preparation for blocking a factor inducing pathological production of such cytokine.

According to another preferred embodiment any factor inducing IL-1Ra production is used in the manufacture of a pharmaceutical preparation for blocking a factor inducing pathological production of such cytokine.

According to another preferred embodiment a compound having the ability of inhibiting the activation and/or activity of enzymes generating immunomodulatory fragments is used in the manufacture of a pharmaceutical preparation for inhibiting the activation or activity of enzymes generating immunomodulatory fragments.

According to another preferred embodiment antibodies directed to enzymes generating immuno-modulatory fragments are used in the manufacture of a pharmaceutical preparation.

According to another preferred embodiment at least one monoclonal antibody, anti-integrin antibody, peptide and/or synthetic construct thereof is used in the manufacture of a pharmaceutical preparation.

A further aspect of the invention includes a pharmaceutical composition comprising a regulatory mechanism controlling factor of an inducing factor of the production or biological activity of immunoregulatory substances including one or more cytokines, for the production of a pharmaceutical preparation to be used for therapeutically control and minimise pathological production of immunosuppressive immunoregulatory substances including one or more cytokine, or to stimulate production of an immunosupportive immunoregulatory substance in a patient suffering from a cancer to enhance the efficacy and/or possibility of therapeutic treatment of cancer, optionally in combination with therapeutically inert additive to enhance performance status.

According to another preferred embodiment a FcR modulating agent is present in a pharmaceutical preparation for controlling immunoregulatory substances, including one or more cytokine production in a patient suffering from cancer by therapeutically modulating FcR activity.

According to another preferred embodiment a FcR modulating agent is used in the manufacture of a pharmaceutical preparation for controlling immunoregulatory substances, including one or more cytokines, including IL-1β, IL-1Ra, IL-6, IL-10, IL-17, TNF-α, and others, production in a patient suffering from cancer is modulated by therapeutically blocking FcR/FcγR activity.

According to another preferred embodiment at least one immunoglobulin, FcR antibodies or fragments of antibodies or synthetic constructs including peptides directed to FcR is used in the manufacture of a pharmaceutical preparation for blocking or cross-linking FcR activity.

According to another preferred embodiment an agent modulating FcγR I, FcγR II and/or FcγR III is present to stimulate IL-2 stimulation of clonal expansion of lymphocytes.

According to another preferred embodiment anti-FcγR I antibodies is present in a pharmaceutical preparation for blocking of FcγR.

According to another preferred embodiment a compound being able to down-regulate the expression of FcR is present in the pharmaceutical preparation for down-regulating FcR.

According to another preferred embodiment at least one FcR-blocking substance minimising production of interleukin-1 receptor antagonist is present in the pharmaceutical preparation for blocking the activity of interleukin-1.

According to another preferred embodiment at least one FcR-modulating soluble receptor is used.

According to another preferred embodiment at least one FcR-modulating enzyme inhibitor is used.

According to another preferred embodiment at least one FcR-inhibiting matrix metalloproteinase inhibitor is used.

According to another preferred embodiment a compound having the ability of inhibiting the activation of enzymes generating immunomodulatory fragments is present in the pharmaceutical preparation for inhibiting the activation of enzymes generating immunomodulatory fragments.

According to another preferred embodiment any factor inducing IL-6 production is used.

According to another preferred embodiment any factor inducing IL-1β production is used.

According to another preferred embodiment any factor inducing IL-10 production is used.

According to another preferred embodiment any factor inducing IL-17 production is used.

According to another preferred embodiment any factor inducing TNF-α production is used.

According to another preferred embodiment any factor inducing IL-1Ra production is used in the manufacture of a pharmaceutical preparation for According to another preferred embodiment a compound blocking a factor inducing pathological production of immunoregulatory substances, including one or more cytokine production is present in the pharmaceutical preparation for blocking a factor inducing pathological production of such immunoregulatory substances.

According to another preferred embodiment antibodies directed to enzymes generating immuno-modulatory fragments are present.

According to another preferred embodiment at least one monoclonal antibody, anti-integrin antibody, peptide and/or synthetic construct thereof, is used.

Immunoregulatory Mechanisms of Relevance for the Present Invention

Published data and the experimental results originally presented below are compatible with dys-regulation of the immune system in cancer patients described herein. Flowchart 1 shows a summary of the immunoregulatory mechanisms described in this invention. Connections between FcR mediated and dysregulatory factor mediated mechanisms are shown with Roman numericals.

There are two main categories of receptors through which IC can modulate the immune system, receptors for the Fc-part of immunoglobulins and complement receptors. IC can activate complement and receptors for various complement factors are expressed on different types of cells of the immune system. However, large ICs are more complement activating than small ones, which are more immunosuppressive. Thus, binding of complement factors activated by ICs is not a major pathway for induction of immunosuppression.

It has been demonstrated beyond any doubt that Fc□R binding (Geissmann et al., 2001; Wolf et al., 1996) and cross-linking of FcγR plays a major role in normal immune regulation. (Gessner et al., 1998; Deo et al., 1997; Lin et al., 2001; Ravetch and Bollag, 2001). These receptors can be either stimulatory or inhibitory and their cross-linking modulates the production of a large number of cytokines by peripheral blood mononuclear cells (PBMC).

Immune complexes, ICs, can influence the activity of various types of cells of the immune system. The effect is highly dependent on the type of cell, which is involved and the characteristics of the immune complexes. In particular the size and whether the immune cells are exposed to soluble or solid phase IC seems to be of importance. Immunocomplexes can be either immunostimulatory or inhibitory depending on their sizes and interaction with different FcRs on immune cells. Large ICs have been demonstrated to be stimulatory whereby is small complexes in antigen excess have been demonstrated to be inhibitory to mitogen induced proliferation (e.g. Gupta and Morton, 1981). It has been demonstrated that there is a correlation between the tumour burden and the immunosuppressive activity of immune complexes.

Serum blocking factors (SBRs) play a major role in immunosuppression in cancer. They have been shown to inhibit both cytotoxic and proliferative activity of lymphocytes from cancer patients (Baldwin, 1976; Bansal et al., 1976; Hellström and Hellström, 1974). SBRs were demonstrated to be immunocomplexes (ICs), as their inhibitory activity was lost after dissociation at low pH, but reappeared after reconstitution at neutral pH (Sjögren et al., 1971). Tumour associated antigens can frequently be bound in IC (Kirkwood and Vlock, 1984; Vlock and Kirkwood, 1985). Removal of ICs from cancer patient sera, using protein A, also reduced the inhibitory effect of these sera.

Data on the prognostic significance of circulating immunocomplexes (CICs) in cancer are somewhat conflicting. In some reports a good correlation to the tumour stage and prognosis has been demonstrated, whereby in others no such correlation was discovered. Based on the results herein this is hardly surprising. The methods used to determine CIC were quite unspecific and were developed to measure only circulating IC. ICs are bound to a large number of cell receptors and the modulatory function of the ICs is mediated via these receptors. It is therefore highly reasonable that ICs are bound to these receptors to and that there will be no circulating IC until the receptors are saturated. Thus, cell bound IC will have a profound influence on the function of receptor bearing cells even in the absence of CICs.

Th1 helper cells are considered to support the development of cytotoxic activity against the tumour. In malignant tumours, however, a predominance of Th2 over Th1 helper cells has been demonstrated repeatedly. Cross-linking of FcγRs is of importance also for this diversion of the immune system, as cross-linking induces production of PEG2 (e.g. Berger et al. 1996), which favours a Th2 situation with production of IL-4, IL-10, etc. IL-4 then inhibits the immune reactivity to the tumour partly by down-regulating monokine production in general, but also by stimulating the production of IL-1Ra. Further, IL-4 stimulates the expression of the inhibitory FcγR II, CD32b, and inhibits expression of the stimulatory receptor CD32a (Pricop et al., 2001). Thus blockade of the FcγR mediated triggering of the Th2 predominance in malignant tumours would certainly improve the immune reactivity to the tumour.

Cross-linking of FcγR by IC can result in activation or inhibition. The latter can be mediated in several ways:
  expression of B7 on monocytes, necessary for co-stimulation in activation of T-cells, is down-regulated;
  increased production of pro-inflammatory monokines, IL-1β, IL-6, TNF-α by monocytes;
  production by monocytes of various substances inhibiting the immune reactivity, e.g., $PGE_2$, TGF-β, sTNF-αR, and IL-1Ra;
  oxidative burst of $O_2^-$-radicals, resulting in down-regulation of the ζ-chain of the T-cell receptor;
  down-regulation of IL-12;
  production of interleukin-1 receptor antagonist (IL-1Ra), which blocks the activity of interleukin-1, necessary for immunostimulation, and expression of endothelial adhesion molecules, necessary for recruitment of inflammatory/immune effector cells to the tumours; modulation of endothelial cell function.

Despite that these facts have been known for a very long period of time, it has so far not been suggested that modulation of FcRs/FcγRs is a very attractive therapeutic principle for treatment of the immune system in cancer patients in order that FcR/FcγR mediated immunosuppression is relieved, and the therapeutic efficacy can be significantly improved.

In the present invention, interleukin-2 (IL-2) stimulated proliferation of PBMC and IL-1Ra production and was chosen as relevant markers for FcγR mediated immunostimulation/suppression.

It is shown below, that solid phase IgG (mimicking large ICs) together with IL-2 results in a significantly increased proliferative response to PBMCs from healthy individuals, as well as cancer patients compared to cultures where solid phase binding was blocked by pre-incubation with human serum albumin (HSA). This effect is most clearly shown when the culture plates were pre-coated with HSA/IgG allowing a high degree of cross-linking of FcγR. The proliferative response to IL-2 could be normalised in cancer patients (compared to controls) using this technique. A stimulatory effect of solid phase IgG was also seen when IgG from serum in the culture medium is allowed to bind to the surface of culture wells. This effect is very clear in cultures of PBMCs from healthy individuals but in about 50% of the cancer patients this stimulation is lost. This stimulatory effect in healthy individuals can be inhibited by adding serum from cancer patients to the culture medium. The mechanism for increased proliferative response to IL-2 in the, presence of FcγR cross-linking is reasonably due to an increased production of supportive cytokines.

In this model blockade of FcγR I (CD64), II (CD32), and III (CD16) with F(ab')$_2$ fragments of monoclonal antibodies directed to these receptors showed that the enhanced proliferative response was inhibited mainly by anti-FcγR I antibodies. These F(ab')$_2$ fragments thus block the receptors in a way similar to that of small immunocomplexes, ICs.

An immunoregulatory role of CD64 has been demonstrated by (Sutterwala et al., 1998; Szabo et al., 1990 and 1991). The mechanism for the inhibitory effect of anti-CD64 F(ab')$_2$ fragment as described below in cultures on solid phase IgG is presumably due to a difference in affinity of the F(ab')$_2$ fragment and the Fc-part of IgG. A higher affinity of the antibody to the receptor will allow blockade of the receptor despite the competition with solid phase IgG. However, if the immunosuppression of PBMC from cancer patients (low proliferative response to IL-2) is due to FcγR blockade by IC, this can actually be overcome by culturing patient PBMC together with IL-2 on solid phase IgG, that is cross-linking of a few FcγR, will be substituted for by a larger number of FcγRs resulting in stimulation.

Based on these considerations one inhibitory mechanism, blockade of FcγR I, can be overcome by providing more extensive cross-linking similar to what is achieved in cultures with solid phase IgG.

The immunomodulatory role of cross-linking of FcγR by solid phase IgG has furthermore been shown by analysing cytokine production in short term cultures of PBMCs with solid phase bound IgG, which in healthy individuals inhibited the production of IL-6. Similarly, in PBMC cultures from both cancer patients and healthy individuals (less frequently) the production of IL-6, IL-1β as well as TNF-α were frequently markedly increased when binding of serum IgG was blocked by pre-incubation of the culture wells with HSA. In accordance with these results the production of IL-1Ra, which is induced by IC or solid phase IgG, was reduced in cultures where solid phase binding of IgG was blocked by pre-incubation with HSA.

Interleukin-1 (IL-1) plays a fundamental role for the initiation of an immune response. However, in order to avoid an over-reactivity of the immune system, there are several ways, in which the immunostimulatory activity of IL-1 can be kept under control, e.g., soluble IL-1 receptors, and IL-1 receptor antagonist (IL-1Ra), a very potent inhibitor of IL-1 mediated activity (Arend et al., 1998; Dinarello, 1997). The inhibitory role of IL-1Ra has been clearly demonstrated in studies on autoimmune diseases and rejection after allogen organ transplantation.

The most potent inducer of IL-1Ra is IC. As demonstrated below the production of IL-1Ra is significantly increased by PBMCs isolated from cancer patients. Thus, cell bound immuno-complexes (CBICs), have been demonstrated to be involved in the dys-regulation of the immune system in cancer patients.

IL-1Ra obviously plays a central role in down-regulation of immune reactivity. As demonstrated here it is frequently expressed in large areas of malignant tumours. This finding is highly compatible with the occurrence of tissue bound IgG in the tumours as IC or solid phase IgG are the most potent inducers of this cytokine.

Thus two inhibitory mechanisms based on modulation of FcγR will be shown below, viz. blockade of FcγR, which inhibits IL-2 stimulation of clonal expansion of lymphocytes, and induction of the inhibitory cytokine IL-1Ra. In addition, a more extensive cross-linking of FcγR results in normalisation of the suppressed IL-2 induced proliferation in cancer patients.

As pointed out below a large number therapeutic strategies can be used to avoid this type of down-regulation (Bowles et al., 1997; Fridman et al., 1993). It is demonstrated herein that blocking FcγR II (CD32) by a monoclonal F(ab)-fragment significantly reduces the production of IL-1Ra. An alternative therapeutic option is to inhibit the intra-tumoural protease activity, which is known to enhance the efficacy of FcγR II interaction (Isashi et al., 1998; van derWinkel et al., 1989).

Thus, the inhibitory effect due to binding of IC to FcγR can be treated using various techniques, e.g. by blocking the inhibitory receptors (see below), by down-modulating the sensitivity of receptors by protease inhibitors or by overcoming the inhibitory effects using more competitive binders/ more extensive cross-linking of the receptors. These strategies will be the base for efficient, new therapeutic strategies to overcome immunosuppression in cancer patients.

An increased serum concentration of IL-6 is often found in cancer patients, especially in patients with advanced disease (Barton, 2001; Blay et al., 1992; Blay et al., 1997; Gadducci et al., 2001; Walther et al., 1998). The source of serum IL-6 is still somewhat unclear and it is generally assumed to be derived from the tumour. It is shown herein that this cytokine is produced in large amounts, in short term cultures, by PBMCs from cancer patients and to a much lesser extent, or not at all, by unstimulated PBMCs from healthy individuals. A high serum concentration of IL-6 is generally related to a paraneoplastic syndrome, poor response to immunotherapy and some types of chemotherapy, as well as a poor prognosis.

It is shown that large amounts of IL-6 is produced by PBMCs from about 50% of the cancer patients, as shown in malignant melanoma, renal cell carcinoma, and colorectal cancer. An increased production of IL-6 is also found in patients with only a minimal tumour burden, as about 50% of the patients with radically resected stage III melanoma have a significantly increased production of IL-6.

IL-6 is a pleiotropic cytokine, which acts as an autocrine growth factor in for example renal cell carcinoma and multiple myeloma. It promotes the inflammatory response, induces acute phase reactants as well as IL-1Ra and is involved in the detrimental chronic inflammatory reaction in patients with malignant tumours. It is thus a good marker for dysregulation of the immune system in cancer patients and the paraneoplastic syndrome.

Production of IL-6 can be induced in various ways, e.g., by IL-1β, and TNF-α, and under certain circumstances also by cross-linking of FcR/FcγR. The degree of cross-linking is of importance for the regulatory effect on the production of IL-6. As shown below, the degree of cross-linking achieved by solid phase binding of serum IgG (from a culture medium) inhibits production of IL-6, as pre-coating the culture wells with HSA (thereby blocking the binding of IgG) results in a significantly higher production of IL-6 in about 30% of cancer patients with various diagnoses. Similarly, IL-6 production was significantly inhibited in cultures of PBMCs from healthy individuals when the culture wells were coated with IgG instead of HSA alone.

The mechanism by which isolated PBMCs continue to produce IL-6 in vitro has so far been unresolved. It is shown herein that serum from cancer patients added to PBMCs from healthy individuals, who by themselves do not produce IL-6, induce the production of large amounts of IL-6. As FcγR cross-linking modulates the production of IL-6, sera known to induce this cytokine, were adsorbed by a surplus of protein-G Sepharose to remove all IgG. These adsorbed sera still induced the production of IL-6 even to a greater extent than before adsorption. These results are compatible with that described herein, that is, a reduced interaction of IgG with PBMCs increase IL-6 production. This IL-6 inducing factor has been further characterised by fractionated ultrafiltration, which demonstrates a factor having a molecular weight of less than 50 kD. This factor has also been identified in the urine from cancer patients. The source of this factor was studied and various tumours were minced and extracted with physiological buffers. An IL-6 inducing factor, IL-6IF, is identified in about 60% of the analysed tumours. Similarly, an IL-6 inducing activity has been found in culture conditioned media from squamous cell carcinoma cell lines from the oral cavity.

Thus this factor, IL-6IF, which has been found in serum and urine, seems to be produced intratumorally. It is neither IL-1β, TNF-α or interleukin-17, as these cytokines could not be found in fractions inducing IL-6.

The identification of IL-6IF in the urine opens interesting diagnostic possibilities. Based on the urine concentration of IL-6IF a simple diagnostic test can be developed which will give essential information about prognosis and the likelihood of therapeutic success, in particular for treatment where IL-6 is related to a poor response rate. This test will of course also be extremely valuable when it comes to treatment strategies dealing with the elimination of IL-6IF/treatment of the chronic inflammatory reaction in cancer patients.

Similar to the situation with IL-6 we have also found inducing activity for TNF-α IL-1β and IL-10 in serum and ultrafiltered urine. The number of inducing factors is for the moment unknown but TNF-α inducing activity was found in samples not inducing IL-6. Thus, reasonably several inducing factors are involved in dysregulation of the immune system in cancer.

The immunosuppressor factor in trauma patients (Easter et al., 1988; Hoyt et al., 1988) was also found to inhibit migration of inflammatory cells. This mechanism might be of importance in immunosuppression in cancer as in untreated patients, inflammatory cells recruited to the tumour generally are found in the stromal areas surrounding the tumour nodules presumably because of inhibition of their migration close to the tumour cells. As fibronectin is of importance for migration it can be envisioned that if the cell receptors normally binding to fibronectin or other ECM-substances in the migration process are blocked by fragments of these substances the cells will no longer be able to migrate. In this context the phenomenon of leukocyte adherence inhibition is of interest as PBMCs from cancer patients under certain conditions demonstrate a highly reduced ability to adhere to plastic or glass surfaces.

IL-6 has by others been shown to be an inducer of IL-1Ra. However, in the present work based on the available malignant melanoma and renal cell carcinoma materials no correlation between IL-6 and IL-1Ra has been found rather the contrary. FcγR cross-linking inhibits production of IL-6 as shown herein and stimulates IL-1Ra production.

The role of IL-6IF containing sera in the immunoregulation in cancer is demonstrated by its effect on the proliferative response to IL-2. The type of solid phase IgG binding is obviously of importance for the effect of IL-2. Coating the wells with purified IgG mixed with HSA gives a more powerful stimulatory signal than binding of serum IgG from the culture medium (uncoated cultures). There is thus a marked difference in the proliferative rate in uncoated cultures and HSA coated cultures with a higher proliferative activity in the presence of solid phase IgG. This difference can be inhibited by sera containing IL-6IF, either by interfering with stimulatory mechanisms or by modulating monocytes to increased production of inhibitors, such as $PGE_2$ or IL-1Ra. The inhibitory effect has not been shown in IgG coated cultures, probably because the more forceful effect on the proliferative response to IL-2 under the conditions used.

The importance of serum factors/soluble factors in dysregulation of the immune system in cancer is furthermore shown by the concomitant immunity phenomenon, which means that immune mediated anti-tumour reactivity can be suppressed in the primary tumour allowing local progression of this tumour while there is still a systemic protection against distant metastases (North, 1985). When, however, the tumour burden is increasing the systemic protection will break down. According to the concept described in this document there will at a certain tumour burden and/or a certain intra-tumoural enzymatic activity be a sufficient systemic concentration of suppressor substances to suppress the immune mediated systemic protection resulting in the establishment of micro-metastases. Thus, by analysing these dysregulatory substances in serum or urine from cancer patients, the patients at high risk of systemic micro-metastases can be identified and these patients are those who should be offered adjuvant treatment.

Matrixmetalloproteases (MMPs), frequently found in tumour tissue, can be induced by inflammatory cytokines and are of importance for degradation of extra cellular matrix proteins (ECMs). This activity is considered to be a prerequisite for metastatic spread, and neo-angiogenesis. Occurrence of MMPs has, in several studies been shown to correlate to a poor prognosis. Obviously, the proteolytic activity of MMPs will result in various types of degradation products, some of which are known to modulate angiogenesis and the activity of chemokines. The low molecular weight fraction, IL-6IF, described herein can be a proteolytic fragment. The presence of the factor in tumour extracts and in culture conditioned media from squamous cell carcinoma cell lines from the oral cavity suggests this origin. It has also been shown in a large number of studies by others that culture conditioned media contain immunomodulatory/immunosuppressive factors (e.g. Ménétrier-Caux et al., 1999; Heimdal et al., 2000; Heimdal et al., 2001). A similar factor with immunosuppressor activity, supposed to be derived from proteolytic degradation of serum fibronectin, has been described in trauma patients (Easter et al., 1988; Hoyt et al., 1988). Factors derived from enzymatic degradation of ECM can most likely be both stimulatory and inhibitory as various cytokine patterns have been induced by various fibronectin fragments (Beezhold and Personius, 1992; Lóopez-Moratlla et al., 1995; Takizawa et al., 1995) and also it was recently demonstrated that the expression of various MMPs in malignant melanoma was related to therapeutic response and prognosis (Nikkola et al., 2001).

The generally found immunosuppressive effect of malignant tumours can thus very well be due to the increased enzymatic/proteolytic activity of the tumours resulting in various immunomodulatory fragments/fragments of ECM or other tumour substances. In addition to this, the proteolytic activity can also explain the frequent occurrence of a large number of soluble factors of importance for immune reactivity in cancer patients (Salih et al., 2001; Sheu et al., 2001), e.g. sIL-2 receptor, sTNF-α receptors, sCD8, sCD4, sICAM-1, sMHC I, sFcR etc. Intra-tumoural enzymatic activity also seems to be of importance for activation of pro-TGF-8 to active TGF-8 (Huber et al., 1992). Based on these considerations intra-tumoural proteolytic activity seems to be a fundamental mechanism by which the malignant tumour manage to divert the tumour bearers defense to the disease.

The occurrence of proteolytic fragments of ECM in serum and urine from cancer patients (Katayama et al., 1993) also opens the possibility to identify various types of fragments and analyse their prognostic significance. Furthermore, the therapeutic efficacy of matrixmetalloprotease inhibitors (MMPIs) resulting in a reduction/inhibition of the production of fragments of certain importance can be determined by analysing the amount of these fragments in serum or urine. Determination of these fragments will thus be proper surrogate endpoints for MMPI therapy and have the potential to significantly increase the therapeutic activity of these drugs by allowing monitoring whereby efficacious dose schedules can be developed.

Dysregulation of the immune system by enzymatic/proteolytic fragments from various tumour substances (derived from tumour tissue or plasma proteins) has so far not been described. A large number of inhibitory as weld as stimulatory fragments can be produced as a result of the intra-tumoural enzymatic activity. This provides for a new understanding of immunosuppression in cancer patients and new therapeutic possibilities based on proper diagnostic tests.

All together the data of this invention demonstrate mechanisms whereby dysregulatory factors give rise to a pathological production of proteolytic enzymes and inflammatory cytokines, which also induce the production of proteolytic enzymes by tumour cells, the activity of these enzymes results in an enhanced release of dysregulatory factors, which then further enhance the production of inflammatory cytokines and proteolytic enzymes, thus creating an autocrine loop. The end result of this loop will then be proteolytic enzymes, which will promote angiogenesis and the metastasising potential and divert the immune reactivity to the tumour.

The dysregulatory inducing factors were further characterised by using 2D-gel electrophoresis and identified after fragmentation using masspectrometry and N-terminal sequence analysis (proteomics technique). The low molecular weight fraction (<30 kD) from urine was analysed by comparing samples from normal healthy controls with samples from patients; by comparing urine samples with and without IL-6 inducing activity; by comparing samples adsorbed and not adsorbed with a surplus of normal PBMCs (responding to IL-6IF). Several proteins/fragments of potential immunoregulatory activity were thereby identified as described below, e.g. fragments of β2-microglobulin, serum albumin and immunoglobulin.

As these fragments were identified based on their adsorption to PBMCs, demonstrating a high degree of binding, the occurrence of receptors for these protein fragments/peptides on normal PBMCs sensitive to IL-6IF can be postulated. As albumin and β2-microglobulin do not normally bind to these cells, it can be further postulated that fragmentation of these proteins results in conformational changes exposing new structures with a specific binding to receptors on PBMCs. As demonstrated herein this results in modulation of the immune system. Thus, the basis for a quite new mechanism of immunomodulation in diseases characterised by a high proteolytic activity, e.g. inflammation and cancer, has been discovered.

Based on identification of IgG and albumin fragments when 2-D gels were compared as described above, these proteins were incubated with MMPs under well-defined conditions. IL-6 inducing activity was found in the supernatants after incubation with MMPs in two different fragmentation buffers. Inducing activity was analysed in cultures with normal PBMCs. In particular incubation of albumin with MMP-1, -2, -3, -13 and incubation of IgG with MMP-2, -3, -7, -13 released IL-6 inducing/modulating activity. Degradation of IgG by MMPs has previously been described (Gearing et al., 2002) and it was suggested that IgG fragments possibly could have a modulatory activity on antibody dependent cellular cytotoxicity (ADCC), but the possibility that these fragments have an immunoregulatory activity in cancer has to our knowledge never been suggested.

In an other experiment, fragments of an extra cellular matrix substance, collagen, was found to have a strong inhibitory effect on IL-2 induced proliferation.

It has been described herein described that IL-6IF can be extracted from malignant tumours, e.g. malignant melanoma, renal cell carcinoma, colorectal cancer. These results were confirmed in a new series of experiments, where homogenised tumours were washed three times in PBS or RPMI in order to collect cytokine inducing factors already present in the tumours, so called "preformed inducing factors" (PIF).

The tumour sections/homogenates (after being thoroughly washed) were incubated for 24 hours at 37° C. together with MMP-2. IL-6 inducing activity could then be demonstrated in of supernatants from several tumours.

Potentially a large number of proteolytic enzymes can be involved in degradation of various tumour substances, therefore adding possible substrates to homogenised, washed tumour tissue might enhance the production of immunoregulatory factors/fragments. In order to further explore the nature of immunomodulating substances/fragments in tumours and based on the observation, mentioned above, that fragments of albumin, IgG and β2-microglobulin efficiently binds to normal PBMCs, we added albumin or IgG to thoroughly washed tumour sections/homogenates and incubated for 24 h at 37° C. It was then found that addition of IgG and in particular albumin markedly increased the production of IL-6IF as determined in PBMC cultures. Control experiments showed that the enhanced IL-6 inducing activity was not due to any protective activity of the added proteins. Thus it is herein demonstrated that immunomodulating IgG and albumin fragments are produced in the intra-tumoural milieu Based on our previous results it might seem amazing that incubation of PBMCs with IgG fragments results in an increased production of IL-6 as pre-coating of culture plates with IgG from serum or an albumin/IgG mixture inhibited IL-6 production. A reasonable explanation to this effect is that the IgG fragments produced by proteolytic degradation manage to block the inhibitory effect of natural IgG. This opens up further interesting possibilities to modulate FcR mediated immune regulation.

Further analyses of PIF-fractions by isoelectric focusing and preparative electrophoresis have identified two fractions with IL-6 inducing activity, with different pI. Preparative electrophoresis also identified two fractions, of different molecular weight, with activity.

Conclusions

Factors dys-regulating the immune system in cancer patients were found in tumour tissue, conditioned culture media from cancer cell lines, serum and urine.

Control of the intra-tumoural enzymatic/proteolytic activity is thus a fundamental mechanism to control the malignant tumour management of diverting the immune mediated defense system of the tumour bearer against the disease.

Thus both FcγR cross-linking and dysregulatory inducing factors (ECM enzymatic/proteolytic fragments) play a fundamental role in immunosuppression in cancer patients. Therapeutic control of these dys-regulatory mechanisms will thus improve quality of life, therapeutic response and increased over-all survival.

As IL-6 is only one product of the dys-regulated inflammatory reaction mentioned herein and often is correlated to production of other cytokines such as IL-1 and TNF-α; the strategy is to block the fundamental dys-regulatory mechanisms in order to down-regulate the detrimental chronic inflammatory reaction.

The present invention is thus not based on suppression of the activity of e.g., IL-1β, IL-1Ra, IL-6, IL-10, IL-17, and/or TNF-α, and others, but to prevent or minimise their production.

Definitions

In the present description the term "tissue" shall be understood to encompass whole blood, serum, plasma, Lymphatic fluid, saliva, urine, faeces, ascites, pleural effusion, pus, as well as any tissue, as such including inflammatory cells.

In the present description the term cancer means: Any new and abnormal growth, specifically a new growth of tissue in which the growth is uncontrolled and progressive.

Therapeutic Possibilities to Improve Immune Reactivity in Cancer by Modulation of FcRs By modulation of FcR either relief of immunosuppression or an enhanced immune activation can be achieved as demonstrated in the present document. Several substances can be used to block FcRs e.g. antibodies or fragments thereof (e.g. $F(ab')_2$ or Fab-fragments, of Mab directed to FcγR), peptides (e.g. from the Fc-part of IgG) or synthetic constructs. The interaction between receptor binding ligands and the receptor can also be achieved by blocking the binding site of the ligand by using, soluble FcRs (recombinant) or peptides or synthetic constructs with a specific high binding affinity. Finally, the signal transduction resulting from ligand binding to FcRs can be inhibited by signal transduction inhibitors. In addition to these modes of interfering with FcRs, their reactivity is influenced by proteolytic activity and can thus be modulated by protease inhibitors. In this context MMPIs can be of special interest.

Alternatively the ligands of FcRs, immunoglobulins or complexed immunoglobulins, can be eliminated and their immunosuppressive activity can thereby be avoided. Recombinant FcRs or synthetic constructs with this reactivity of proper affinity and size can be administered in order that CIC (especially small CICs) are bound and eliminated. To further enhance the elimination of CICs binders of these substances can be linked to small microspheres (less than 3-5 mm in diameter, possibly degradable) which are rapidly taken up by the reticulendothelial system/monocyte macrophage phagocyte system.

Another therapeutic possibility is to reduce the number of FcRs which can have a negative effect of the immune reactivity to the malignant tumour, e.g. by increasing their shedding or by down-regulation of their expression.

An alternative to block FcRs, which result in down-regulation of the immune reactivity, can, as has been demonstrated in this document, be to cross-link FcRs in order to overcome immunosuppression. Several possibilities can be used for this purpose, e.g. complexed immunoglobulins/monoclonal antibodies or fragments (Fc) thereof binding to the receptors or synthetic FcR-binding constructs, cross-linking FcR to a degree (number of FcRs of one or several types) achieving optimal immune activation.

Therapeutic Possibilities to Improve Immune Reactivity in Cancer by Controlling Dys-Regulatory Inducing Factors.

Inhibition of the fragment's biological activity (e.g. by monoclonal antibodies or fragments or synthetic constructs binding to and inhibiting the biologic activity of the fragments, synthetic constructs binding to the receptors mediating the biologic effect of the fragments, blockade of the receptors on immune cells, protein fragments/peptides interfering with the receptor interaction of the fragments and thereby inhibiting the biological activity of the fragments.); Elimination of the fragments from the body (e.g. by monoclonal antibodies (or fragments) or other "binders" binding to and eliminating the fragments); Signal transduction inhibitors, blocking the effect of receptor binding; Blocking the activity of the "dysregulated signal substances/cytokines.

If these factors are generated by enzymatic activity resulting in release of immunomodulatory fragments, the following therapeutic possibilities can be envisioned: Inhibition of the production and activation of the relevant enzymes (e.g. by anti-integrin antibodies or suitable peptides); Inhibition of these enzyme activities (e.g. by low molecular weight inhibitors, monoclonal antibodies or peptides);

Materials and Methods

Cytospin preparations for immunocytological demonstration of IgG Peripheral blood mononuclear cells (PBMC) were separated as described below and immediately spun down on pre-cleaned microscope slides in a Shandon Cytospin (Shandon Scientific Ltd, UK) at 1000 RPM for 7 min using 100 µl of the PBMC suspension at $5\times10^5$/ml. The slides were left to dry at room temperature over night, were then wrapped in parafilm and stored −70° C. until further processed. The cells were pre-hydrated in BSS-HSA (Hank's balanced salt solution (BSS, Gibco BRL, UK) supplemented with 0.01M. Hepes solution and 1% human serum albumin (HSA, Pharmacia & Upjohn, SE), for 15 minutes, fixed in phosphate-buffered 4% paraformaldehyde (PFA, Riedel-de Haen Ag, Germany) supplemented with 5.4 g./l. of glucose for 5 minutes and then washed three times in BSS-HSA, incubated with biotinylated protein G (Sigma Chemical Co, US) at 50 µg/ml for 30 minutes, washed in BSS-HSA followed by incubation with alkaline phosphatase-labelled streptavidin (Dakopatts AB, SE) at a ¹⁄₁₀₀ dilution in BSS-HSA for 30 minutes. After washes in Tris buffered saline (TBS) and incubation for 20 minutes in alkaline phosphatase substrate consisting of Naphtol AS-MX Phosphate (Sigma) in 0.1 M Tris buffer with Dimethylformamide, 1 M Levamisole (Sigma) and Fast-Red TR salt (Sigma), the sections were again washed in TBS. They were then counterstained in Mayer's haematoxylin for 1 minute and mounted in Glycergel (Dakopatts AB). All incubations were performed in a moist chamber and all antibody and protein-G solutions were prepared in BSS-HSA. Alternatively, after fixation and washing in BBS containing 2% goat serum, the cells were blocked in 10% goat serum for 20 minutes and incubated with mouse anti-human IgG monoclonal antibody (Nordic Immunology) at 1 or 10 µg/ml, washed in BSS containing 2% goat serum, incubated with Envision (Dakopatts AB, SE) for 30 minutes, washed in TBS and incubated with the alkaline phosphatase substrate for 20 minutes after which the sections were again washed in TBS. They were then counterstained in Mayer's haematoxylin for 1 minute and mounted in Glycergel (Dakopatts AB,SE). All incubations were performed in a moist chamber and all antibody solutions contained 2% normal goat serum.

Preparation of Tumour Biopsies and Immunological Staining of Tissue Sections for IgG Biopsies from the resected metastases were immediately snap frozen and stored at −70° C. until further processed. Frozen tissue sections, 6-7 µm thick, were fixed with 4% PFA for 5 minutes and then washed three times in BSS-HSA. For double-staining, sections were incubated with primary antibody, mouse IgG1 anti-human CD3 (Dakopatts AB), at 1 µg/ml for 30 minutes, washed in BSS-HSA followed by incubation with goat-anti-mouse immunoglobulin (Dakopatts AB, SE) at a 1/25 dilution in BSS-HSA. Monoclonal mouse IgG1 against an irrelevant antigen (Dakopatts AB, SE) was used as a negative control. The sections were then incubated with PAP mouse monoclonal antibody (Dakopatts AB, SE) at a 1/25 dilution in BSS-HSA for 30 minutes. 3,3'-Diaminobenzidine (DAB, Sigma) was used as a substrate, which resulted in a brown colour. The presence of IgG was then identified using 1 or 10 µg/ml biotinylated protein G (Sigma) which was incubated for 30 minutes, washed in BSS-HSA, followed by incubation with alkaline phosphatase-labelled streptavidin (Dakopatts AB, SE) at a 1/100 dilution in BSS-HSA for 30 minutes. After washes in TBS and incubation with alkaline phosphatase substrate for 20 minutes, the sections were again washed in TBS. They were then counterstained in Mayer's haematoxylin for 1 minute and mounted in Glycergel (Dakopatts AB, SE). All incubations were performed in a moist chamber and all antibody and protein-G solutions were prepared in BSS-HSA. The alkaline phosphatase staining resulted in a bright red staining for IgG. Double-stained cells appeared as red-brown.

Preparation of Tumour Biopsies and Immunological Staining of Tissue Sections for Interleukin-1 Receptor Antagonist (IL.1Ra).

Paraffin sections, 6-7 µm thick, were de-paraffinised by cooking in a pressure cooker in BSS with 0.01 M Hepes solution and 1% saponin (Sigma) (BSS-saponin) for 6 minutes. The sections were first blocked with 10% normal human AB-serum before staining and were then incubated with biotinylated goat IgG antibodies directed either to interleukin-1α or interleukin-1 receptor antagonist (both from R&D Systems, UK) at 10 µg/ml over night, washed in BSS-saponin, incubated with alkaline phosphatase-labelled streptavidin (DAKO, SE) at a 1/100 dilution in BSS-saponin containing 2% human AB-serum for 30 minutes. After washes in TBS and incubation with the alkaline phosphatase substrate for 20 minutes, the sections were again washed in TBS and were then counterstained in Mayer's haematoxylin for 1 minute and mounted in Glycergel (Dakopatts, Sweden). All incubations were performed in a moist chamber and all immunoglobulin solutions were prepared in BSS-saponin containing 2% human AB-serum. Staining for interleukin-1α was used as a negative control in this context.

Preparation of Peripheral Blood Mononuclear Cells (PBMC)

Venous blood was drawn from healthy volunteers or from cancer patients in glass vacuum tubes with acid dextrose citrate solution A as an anti-coagulant (Vacutainer, Becton & Dickinson, NJ). Erythrocytes were removed by sedimentation on 2% dextrane T500 solution (Amersham Pharmacia Biotech AB, SE) in 0.9% NaCl. Mononuclear cells were then isolated by Ficoll-paque Plus (Pharmacia AB, SE) density gradient centrifugation after which the cells were washed twice in RPMI1640 Dutch's modification (RPMI) (Gibco BRL, Scotland) with 2% human serum albumin (HSA) (Pharmacia & Upjohn, SE). Cell viability was assessed by exclusion of 0.05% Trypan Blue and was always above 95%. The cell suspension was stained with Turks solution and the number of lymphocytes and monocytes in the PBMC preparation were counted in a hemocytometer. PBMCs were suspended in RPMI with 2% HSA and the cell concentration were adjusted to $5 \times 10^5$ lymphocytes/ml.

PHA stimulated proliferation of PBMC with and without chlorambucil Venous blood was drawn at the indicated time points from RCC patients undergoing IL-2 (Proleukin, Chiron, NL) therapy. Mononuclear cells were isolated by Ficoll-Isopaque (Pharmacia, SE) density gradient centrifugation. $5 \times 10^4$ PBMC in a final volume of 200 µl were seeded into round-bottomed microtiter plates (Corning Inc. NY, US) in culture medium consisting of RPMI 1640 supplemented with 100 IU/ml Penicillin, 100 µg/ml Streptomycin (Flow laboratories) and 10% heat-inactivated, autologous fresh serum. Phytohemagglutinin (PHA, Sigma Chemical Co, MO, US), at a final concentration of 20 µg/ml, and Chlorambucil (CHL, Sigma), at a final concentration of 1 µg/ml, were then added. Cells were cultured for 3 days in a humidified 5% $CO_2$ atmosphere at 37° C. Proliferation was assayed by incorporation of 1.6 µCi/well of [3H]thymidine (Amersham Int, UK) during the last 18 hr. Mean values of dpm (disintegrations per minute) of triplicate cultures were used for the calculations.

Measurement of TNF-α in PHA Stimulated Cultures

PHA-stimulated cultures with or without chlorambucil (1 µg/ml) were set up in parallel as described above for mitogen-stimulated cultures. Supernatants were collected after 72 hours and cells were removed by centrifugation for 5 minutes at 4000 RPM. The SNs were frozen immediately and stored at −70° C. The amount of TNF-α in the SNs was evaluated with an ELISA kit from Immunotech S.A., FR, according to the manufacturer's instructions. The lower limit of detection in this assay was 10 pg/ml.

Pre-Coating of Culture Plates with HSA and HSA/IgG

Round-bottomed, 96-well tissue culture plates (Costar, Corning Inc. NY, US) were pre-coated with HSA only or HSA and pooled human IgG for intravenous injection (Gammagard, Baxter AS, DK). HSA was diluted in RPMI1640 without supplements to a concentration of 10 mg/ml. In some experiments, 1 mg/ml IgG was mixed into a solution of 9 mg/ml HSA in RPMI (HSA/IgG). 200 µl of HSA or HSA/IgG were then added to each well of the plate. The plates were incubated at 4° C. for 30 minutes after which the wells were washed twice with 200 µl of RPMI1640. The coated plates were used immediately.

IL-2 Induced Proliferation of PBMC in Uncoated and Coated Culture Plates

100 µl of RPMI1640 supplemented with 200 IU/ml penicillin, 200 µl/ml streptomycin, 4 mM L-glutamine (all from Sigma Chemical Co. MO, US) and 20% heat-inactivated human serum (autologous or from cancer patients) were added to uncoated, HSA or HSA/IgG coated tissue culture microtiter plates. PBMC, isolated from healthy individuals or patients with metastatic renal cell carcinoma, were diluted in RPMI/2%1-ISA at a concentration of $5\times10^5$/ml and 100 µl were added to the microtiter wells. Interleukin-2 (IL-2, Proleukin, Chiron, NL), at a final concentration of 120 IU/well, was added to some wells. Cells were cultured for 7 days in a humidified, 5% $CO_2$-atmosphere at 37° C.

Proliferation was assayed by incorporation of 1.6 µCi/well of [3H]-thymidine (Amersham Int., UK) during the last 18 hrs. Mean values of dpm (disintegrations per minute) of triplicates were used for the calculations.

Inhibition of IL-2 Induced Proliferation of PBMCs by Monoclonal Antibodies to FcγR.

Cultures for IL-2 induced proliferation were set up with PBMC from healthy individuals as described above with the exception that the PBMC were first pre-incubated with antibodies against human FcγR as follows: PBMC, at a concentration of $5\times10^5$/ml in RPMI/2% HSA, were incubated at room temperature for 30 minutes with 25 µg/ml of F(ab')$_2$ mouse anti-human CD16 (FcγR III), CD 32 (FcγR II), or CD 64 (FcγR I) (all purchased from Ancell Co. MN, US). 100 µl of the respective antibody-containing cell suspension was then added to the microtiter wells.

Generation of cell culture supernatants for monokine determination 100 µl of culture medium consisting of RPMI1640 supplemented with 200 IU/ml penicillin, 200 µg/ml streptomycin, 4 mM L-glutamine (Sigma Chemical, MO, US) and 20% fresh heat-inactivated autologous serum were added to un-coated or -pre-coated microtiter plates followed by 100 µl of PBMC suspension ($5\times10^4$ lymphocytes) in RPMI/2% HSA. In some experiments Lipopolysaccharide (LPS, Sigma Chemical Co, MO, US) was added at a concentration of 0.05 ng/ml. Cells were cultured in a humidified, 5% $CO_2$ atmosphere at 37° C. Supernatants (SNs) were harvested after 24 hrs and residual cells were removed by centrifugation in a refrigerated centrifuge (Beckman) at 2600×g for 5 minutes. SNs were frozen and stored at −70° C. until monokine concentrations were measured by ELISA.

Monokine ELISAs

Monokines were assessed by ELISA using the DuoSet ELISA development system for human IL-6, TNF-α or IL-1β (R&D Systems Europe, Ltd. UK) following the manufacturer's recommended procedures. Lower limit of detection was 3.1 µg/ml for IL-6, 15.6 µg/ml for TNF-α and 3.9 µg/ml for IL-1β. IL-10 was detected with a kit from Diaclone Research, FR. The lower limit of detection was 5 µg/ml. Human IL-1Ra was detected with a quantitative sandwich ELISA using a monoclonal mouse anti-human IL-1Ra as capture antibody and a biotinylated goat anti-human IL-1Ra as developing antibody (both from R&D Systems). Briefly, enhanced binding 96-well microtiter plates (Labsystems AB, SE) were coated overnight at room temperature with 10 µg/ml of capture antibody diluted in PBS. After washing in PBS with 0.05% Tween 20 (Sigma Chemical, MO, US) plates were blocked with a blocking buffer consisting of 1% bovine serum albumin (BSA, Sigma), 5% sucrose (Sigma) and 0.05% $NaN_3$ in PBS. PBMC culture SNs or recombinant human IL-1Ra standard (R&D Systems) were diluted in 0.1% BSA and 0.01% Tween 20 in PBS (dilution buffer) and incubated over night at room temperature. After washing, the biotinylated-developing antibody was added at 100 ng/ml in dilution buffer. This was incubated for 1 hr at room temperature. Plates were washed and alkaline phosphatase (ALP)-conjugated Extravedin (Sigma), at a dilution of 1:10000 in Tris buffered saline with 0.1% BSA was added. Following incubation for 1 hr at room temperature, plates were washed and the amount of bound IL-1Ra was measured by hydrolysis of paranitrophenyl phosphate (Sigma). Optical density was read at dual wavelengths, 405 nm and 570 nm, respectively, in a Multiscan EX microplate reader (Labsystems). The lower limit of detection in this assay was 39 pg IL-1Ra/ml Inhibition of IL-1Ra Production by PBMC with Antibodies Against FcγR II PBMCs, isolated from healthy volunteers were pre-incubated at $1\times10^6$/ml in RPMI1640+2% HSA with 5 or 50 µg/ml of azide-free, mouse anti-human CD32 Fab (Medarex Inc. NJ, US) for 1 hr at 37° C. under gentle agitation. The cells ($5\times10^5$/well) were immediately seeded onto uncoated or HSA/IgG coated tissue culture microtiter plates in RPMI1640 with 10% heat-inactivated, pooled human AB sera. Supernatants were harvested after 24 hrs, as described under "generations of cell culture supernatants", and the production of IL-1Ra was measured by ELISA.

Inhibition of IL-1Ra production by PBMC with Tosyl PBMC ($2\times10^6$/ml) from healthy volunteers were pre-incubated with various concentrations of Na-p-Tosyl-L-lysine chloromethyl ketone (Tosyl, Sigma) diluted in RPMI1640/ 2% HSA for 30 minutes at 37° C. after which the cell suspensions were washed three times in RPMI/2% HSA. 100 µl of culture medium consisting of RPMI1640 supplemented with 200 IU/ml penicillin, 200 µg/ml streptomycin, 4 mM L-glutamine (all from Sigma) and 20% fresh heat-inactivated autologous serum were added to the HSA or HSA/IgG pre-coated microtiter plates followed by 100 µl of the PBMC suspensions ($5\times10^4$ lymphocytes) in RPMI/2% HSA. Cells were cultured in a humidified, 5% $CO_2$ atmosphere at 37° C. Viability of cultured PBMCs were also assessed after 24 hrs by Trypan blue exclusion and found to be 100%. SNs were harvested after 24 hrs and residual cells removed by centrifugation in a refrigerated centrifuge at 2600×g for 5 minutes. SNs were frozen and stored at −70° C. until IL-1Ra concentration was determined by ELISA.

Preparation of Samples for Testing of Monokine-Inducing Activity

Below it will be described the handling of various samples that were co-cultured with PBMCs from healthy individuals in order to assess monokine-inducing activity. The samples included human serum and urine (collected from cancer patients and normal healthy individuals), extracts from tumour biopsies and conditioned media from human tumour cell lines. The numbers assigned to patient samples and control PBMcs in the result tables are only valid for that particular table.

Affinity Chromatography of Human Sera with Protein G-Coupled Sepharose

Heat-inactivated human serum was passed over a HiTrap protein G-Sepharose HP affinity column (Amersham Pharmacia Biotech AB, SE). to The non-binding fraction was eluted with RPMI1640, giving a final dilution effect of ⅕ (20%) of the original serum. 200 IU/ml penicillin, 200 µg/ml streptomycin, 4 mM L-glutamine (all from Sigma) were added. The eluate was then sterile filtered with a 0.45 µm Millex syringe filter (Millipore Co. MA, US) and used immediately for culture with control PBMC. 100 µl medium with 20% original serum or with 20% protein G non-binding serum from the same source was added to uncoated or HSA-coated microtiter plates together with 100 µl PBMC suspension ($5\times10^5$/ml). Cell-free SNs were harvested after overnight incubation and tested for monokine activity by ELISA, as described above.

Ultra Filtration

All ultra filtrations were carried out using Amicon Centriplus centrifugal filter devices (Millipore Co. MA, US) sterilised by autoclave. Filters with a 3000, 50000, or 100000 molecular weight cut-off were used. The Centriplus filters were washed with RPMI1640 prior to use. The Centriplus filters were spun on a refrigerated centrifuge with a swing-out rotor at 3000×g. Retentates were recovered by inverse centrifugation at 2000×g.

Serum Samples

Sera, collected from cancer patients or from normal healthy individuals, were heat-inactivated for 30 minutes at 56° C. and frozen at −70° C. After thawing, sera were diluted in RPMI1640 to a concentration of 20% and either used unfiltered or ultra-filtered, as described below, in co-culture experiments for monokine-induction with control PBMC. Ultra filtered serum fractions consisted of filtrates from 100000 mw cut-off filters, retentates or filtrates from 50000 mw cut-off filters or retentates from serum fractions that had been sequentially spun on a 50000 mw cut-off filter followed by concentration on a 3000 mw cut-off filter. Retentates were reconstituted in RPMI1640 with 200 IU/ml penicillin, 200 µg/ml streptomycin, 4 mM L-glutamine (Sigma) to their original volume. 100 µl of diluted sera (20%) or ultra filtered serum fractions were added to uncoated or HSA-coated microtiter plates together with 100 µl PBMC suspension ($5 \times 10^5$/ml). Cell-free SNs were harvested after over-night incubation and tested for monokine activity by ELISA, as described above.

Urine Samples

Approximately 15 ml of urine were collected from cancer patients with renal cell carcinoma or malignant melanoma or from normal healthy individuals. The samples were centrifuged for 10 minutes at 3000×g followed by filtration over a 0.45 µm Millex-HV syringe filter (Millipore). Next the samples were ultra filtered through a 50000 mw cut-off Centriplus filter and the filtrate concentrated on a 3000 mw cut-off filter. The volume of the retentate, collected from the 3000 mw filter was adjusted to 1 ml with RPMI1640. The sample was then again filtered on a 0.45 µm Millex-HV syringe filter and frozen at −70° C. Immediately before co-culture with normal PBMC, the samples were thawed and buffer exchange was performed to RPMI1640 with 200 IU/ml penicillin, 200 µg/ml streptomycin, 4 mM L-glutamine (Sigma) by gel filtration over a Sephadex-G25 (PD-10) desalting column (Pharmacia, SE).

Extracts from Tumour Biopsies

Human tumour biopsies from patients with renal cell carcinoma, malignant melanoma or colon carcinoma, were embedded in glycergel (Dakopatts AB, SE) and frozen at −70° C. For generation of tumour extracts, approximately 8 to 20, 50 µm cryostat sections were cut and transferred to 4 ml of cold RPM1640 with 200 IU/ml penicillin, and 200 µg/ml streptomycin (RPMI/PEST) (Gibco BRL) and kept on ice. The sections were centrifuged and resuspended in 0.5 ml fresh RPMI/PEST after which they were disaggregated in a Medimachine (Dako A/S, DK) using a sterile Medicon 500m unit. The disaggregated sample was suspended in 2 ml RPMI/PEST, vortexed and kept on ice for 0.5 to 2 hrs. The sample was centrifuged 10 minutes at 300×g and the supernatant was harvested. The supernatant was then filter sterilised through a 0.45 µm Millex-HV syringe filter (Millipore). For generation of extracts from fresh tumour biopsies, a newly excised biopsy (about 5 mm$^3$) was disaggregated in a Medimachine (Dako AS), using a sterile Medicon 50 µm unit and resuspended in a total volume of 5 ml TCN buffer (50 mM Tris, 50 mM NaCl, 10 mM $CaCl_2$ + 200 IU/ml penicillin and 200 µg/ml streptomycin). The cell suspension was incubated on ice for 1 hr. The sample contained $2.7 \times 10^6$ cells/ml with a viability of 15%. A cell-free supernatant was harvested after the cells had been pelleted for 10 minutes at 300×g. The supernatant was then filtered through a 0.45 µm Millex-HV syringe filter (Millipore). Supernatants, extracted from frozen or fresh biopsies were then ultra filtered as described above. Before co-culture with control PBMC, the TNC buffer was exchanged to RPMI1640 with 200 IU/ml penicillin, 200 µg/ml streptomycin, 4 mM L-glutamine (Sigma) by gel filtration over a Sephadex-G25 (PD-10) desalting column (Pharmacia). SNs, 100 µl, were added to uncoated microtiter plates together with 100 µl PBMC suspension ($5 \times 10^5$/ml). Cell-free SNs were harvested after over-night incubation and tested for monokine activity by ELISA, as described above.

Conditioned Media from Tumour Cell Lines

Established human, squamous cell carcinoma cell lines, UT-SCC-10 and UT-SCC-20A (a gift from Dr. R. Grenman, University of Turku, Finland) were cultured in 5 ml media consisting of Dulbecco's modified Eagle's medium (DMEM) supplemented with 1 mM L-glutamine, 18 mM Hepes, 0.9% non-essential amino acid solution, 100 IU/ml penicillin, 100 µg/ml streptomycin (all from Gibco) and 10% heat-inactivated human AB-serum (DMEM) in 25 cm$^3$ cell culture flasks (Costar) at 37° C. and 5% $CO_2$. The medium was decanted off and replaced every 2 to 3 days. When the cells had reached confluence they were trypsinated and reseeded in new flasks. The decanted medium was centrifuged at 1000×g to remove residual cells and debris and then ultra filtered on Centriplus filters with a 50000 mw cut-off. The filtrate was then concentrated on a 3000 mw filter. In some experiments the retentate from the 50000 mw cut-off filter was also saved. Retentates were resuspended in RPMI1640 to 2.5 ml. Before culture with PBMCs the medium was exchanged to RPMI1640 with 200 IU/ml penicillin, 200 µg/ml streptomycin, 4 mM L-glutamine (Sigma) by gel filtration over a Sephadex G-25 (PD-10) desalting column (Pharmacia). In some experiments parallel culture flasks containing only culture medium and no tumour cell lines were set up as a control. Supernatants from these flasks were treated exactly the same as supernatants from flasks containing cells. Filtrates and retentates were saved at 4° C. before co-culture with normal PBMC. SNs, 100 µl, were added to uncoated or HSA-coated microtiter plates together with 100 µl PBMC suspension ($5 \times 10^5$/ml). Cell-free SNs were harvested after over-night incubation and tested for monokine activity by ELISA, as described above.

Affinity Chromatography with Gelatine-Coupled Sepharose

Pre-swelled gelatine Sepharose 4B (Pharmacia Biotech AB, SE) was washed three times in PBS or RPMI1640. 0.3-0.5 ml Sepharose gel was incubated together with the 3-50 kD fractions of ultra filtered serum, diluted in 2-2.5 ml RPMI1640 for 30 minutes at room temperature. The gel was mixed gently by inversion approximately every 10 minutes. An equal portion of the ultra filtered serum sample was incubated in parallel without gelatine Sepharose, as a negative control. The gel was allowed to settle and the supernatant collected. Buffer exchange to RPMI1640 with 200 IU/ml penicillin, 200 µg/ml streptomycin, 4 mM L-glutamine (Sigma) was performed by gel filtration over a Sephadex-G25 (PD-10) desalting column (Pharmacia) followed by filtration on a 0.45 µm Millex-HV syringe filter (Millipore). SNs, 100 µl, were added to uncoated microtiter plates together with 100 µl of control PBMC suspension ($5 \times 10^5$/ml). Cell free SNs were harvested after over-night incubation and tested for monokine activity by ELISA as described above.

Sample Preparation for Proteomics

Urine samples (100-450 ml) from cancer patients or healthy controls were ultra centrifuged on Jumbosep centrifugal devices (Pall Life Science, MI, US) using a 30 K membrane insert or alternatively, with a Proflux M12 system using a 30 K Pellicon 2 mini filter (Millipore, MA, US) followed by concentration on Jumbosep with a 3K membrane insert. The urine fraction, 3-30 KD, was tested for monokine-inducing activity as previously described herein. Protein concentrations were determined by Bio-Rad protein assay (Bio-Rad Laboratories, CA, US). Samples were desalted over a Sephadex-G25 (PD-10) column (Amersham Biosciences, SE), lyophilised and dissolved in rehydration buffer (8M urea, 4% CHAPS, 10 mM DTT, 0.5% v/v IPG buffer and a trace of orange G). Samples were centrifuged to remove undissolved material.

2-DE Gel Electrophoresis

2-DE was performed in a horizontal 2-DE set-up (Multiphore/IPGphore, Pharmacia Biotech, SE) as described (Lindahl M. et. al 1998) based on isoelectric focusing (IEF) in the first dimension and molecular mass in the second dimension. Briefly, samples (230 µg, 350 µg, 600 µg) were applied to IPG gels, pH 4-7, (Amersham Pharmacia Biotech, SE) and focused overnight for 48000Vh. SDS-PAGE was then carried out with 16% T/1% C polyacrylamide casted slab gels. Molecular weight standards were included in each run. Separated proteins were detected by Coomassie blue staining or SYPRO Ruby staining. The protein patterns in the gels were analyzed as digitised images using a CCD (Charged-Coupled Device) camera (1340×1040 pixels) in combination with a computerized imaging 12-bit system, PDQuest Version 6.1.0, in the case of fluorescent stained gels using UV scanning illumination mode (Fluor-S Multi-imager, Bio-Rad). The amount of protein in a spot was assessed as background-corrected optical density, integrated over all pixels in the spot and expressed as integrated optical density (IOD).

Mass Spectrometry

Tryptic digests of excised protein spots were performed using MALDI_TOF MS (Voyager-DE PRO, Applied Biosystems, CA, US) as previously described (Ghafouri B. et al. 2002)

Electrotransfer and N-Terminal Sequence Analysis

Selected protein spots were electro transferred to PVDF membranes and subjected to N-terminal sequence analysis by Edman degradation in a Procise cLC or a Procise HT sequencer (PE-Applied Biosystems) at the Protein Analysis Center, Karolinska Institute, Stockholm, Sweden.

Proteomics on PBMC-adsorbed urine fractions from cancer patients PBMC were prepared from buffy coat peripheral blood from normal controls as described above. Monokine production by the PBMCs in response to urine fractions from cancer patients was verified as described above. Remaining PBMC were frozen at −70° C. until use. For adsorption of urine fractions, the PBMCs were thawed and washed carefully in cold phosphate buffered saline (PBS). Approximately $50 \times 10^6$ PBMC were added to 2.7 or 2.6 ml, respectively, of ultra centrifuged (3-30 KD) urine fractions pooled from two patients with renal cell carcinoma or from one patient with malignant melanoma. Unabsorbed urine fractions, used as controls, received the equivalent volume of PBS without PBMC. The urine fractions were incubated for 1½ hour at 4° C. The PBMC were then removed by centrifugation. The adsorbed urine fractions were tested for monokine-inducing activity in fresh, normal PBMC as described above. Remaining urine fractions were stored at −70° C. until determination of protein concentration and analysis with 2-D gel electrophoresis, mass spectrometry and N-terminal sequencing as described above.

Fragmentation of IgG and Serum Albumin Using Matrix Metalloproteinases (MMPs)

MMP-1, -2, -13 (R&D Systems) and MMP-3 and -7 (Chemicon, UK) were activated according to instructions of the manufacturer. 1-50 ng/ml of the indicated MMPs were then incubated with 1 mg/ml of either human serum albumin (HSA, Octapharma, SE) or pooled human IgG for intravenous injection (IvIg, Gammagard, Baxter, DK) as substrate in RPMI or in 50 mM Tris-HCl, pH 7.5 (containing 0.15 M NaCl, 10 mM $CaCl_2$ and 0.05% Brij35). The mixtures were incubated for 5-20 hours at 37° C. Parallel incubations of MMP or the substrates alone, in respective buffer, were set up as controls. The mixtures were buffer exchanged to RPMI as described previously and filtered through a 0.45 µm Millex-HV syringe filter (Millipore, MA, US). Storing of mixtures, when needed, was performed at −70° C. until analysing by gel-electrophoresis and testing for monokine inducing activity in fresh, normal PBMC as described above.

IL-2 Induced Proliferation of PBMC in the Presence of Collagen/Collagen Fragments Purified collagen from human skin (Sigma) at a concentration of 100 µg/ml was incubated in 100 mM Tris-HCl, pH 7.6, containing 0.15 M NaCl, 10 mM $CaCl_2$ and 0.05% Brij35 over night at 37° C. The buffer was then exchanged to RPMI1640 by gel filtration through a Sephadex-G25 (PD-10) column (Amersham Biosciences) and filtered through a 0.45 µm Millex-HV syringe filter (Millipore) and frozen at −70° C. until use. The collagen was tested for effect on IL-2 stimulated proliferation of PBMC from healthy donors in the presence of autologous serum as described. Final concentration of collagen in the proliferation assay was 26 ug/ml.

Homogenisation of Tumour Biopsies

Frozen, human tumour biopsies, embedded in Tissue-Tek OCT Compound (Sakura, NL) or cryostat sections from patients with renal cell carcinoma, malignant melanoma or colon carcinoma were transferred to 3-10 ml of cold RPMI or PBS with 2001 U/ml penicillin and 200 µg/ml streptomycin (RPMI/PEST, PBS/PEST) (Gibco BRL) and kept on ice. The tissue was washed three times by centrifugation and resuspension in 3-10 ml cold RPMI/PEST or PBS/PEST. The pelleted, washed tissue was cut into pieces of approximately the same size and each piece was homogenised using a Mikro-Dismembrator U (B. Braun Biotech International, GE). The tissue was transferred to a PTFE shaking flask together with 1 ml RPMI/PEST or PBS/PEST and a tungsten carbide grinding ball and homogenised during 15-20 seconds with a shaking frequency of 1500-2000 RPM. The homogenised tissue suspension was transferred to a test tube and kept on ice.

Extraction of Preformed Immunomodulation Factors (PIF) from Homogenised Tumour Tissue Human tumour biopsies or cryostat sections were homogenised as described above. The homogenous tissue suspension was washed three times by centrifugation in a final volume of 1.5 ml, 10 ml or 23 ml cold PBS/PEST or RPMI/PEST, as appropriate. The supernatants, containing PIF, was collected, pooled and kept on ice. PIF was then filtered through a 0.45 µm Millex-HV syringe filter (Millipore) and stored at −70° C. Before testing for monokine inducing activity in fresh, normal PBMC as described above, PIF was buffer exchanged to RPMI as described previously and filtered through a 0.45 µm Millex-HV syringe filter (Millipore).

Homogenised, Washed Tumour Tissue Incubated with Matrix metalloproteinase-2

The collection, washing and homogenisation of tumour cryo sections (3×300 µm) were carried out as described above. The pelleted tumour tissue was suspended in 0.5 ml cold RPMI/PEST. MMP-2 (R&D Systems, UK), activated according to instructions from the manufacturer, was added at a final concentration of 5 ng/ml. The tumour tissue suspension was incubated with MMP-2 for 20 h at 37° C. and the supernatant collected after centrifugation. Parallel incubation of tumour tissue with no addition of MMP-2 was set up as a control. The mixtures were buffer exchanged to RPMI by gel filtration through a Sephadex-G25 (PD-10) column (Amersham Biosciences, SE) and filtered through a 0.45 μm Millex-HV syringe filter (Millipore, MA, US). Finally, the mixtures were analysed by gel-electrophoresis and tested for monokine inducing activity in fresh normal PBMC as described above.

Homogenised Tumour Tissue and PIF Incubated with Serum Albumin or IgG

The pelleted homogenised tumour tissue formed during preparation of PIF (se above) was kept on ice and stored at −70° C. PIF were prepared as described above. In one experiment, the homogenised sections were washed once more to collect a fourth supernatant, used as a control reflecting the IL-6 inducing activity in tumour sections before incubation. The fourth supernatant was divided into two parts, to one of which was added 20 mg/ml of HSA and directly frozen at −70° C. The mixtures of homogenised tumour tissue with 20 mg/ml HSA or with 10 mg/ml pooled human IgG for intravenous injection (IvIg), as well as the mixtures of PIF with 20 mg/ml HSA or with 10 mg/ml IvIg, all in RPMI/PEST, were incubated for 18-21.5 h at 37° C. Parallel incubations of tumour tissue and PIF with no addition of HSA or IvIg, as well as RPMI/PEST with addition of HSA or IvIg, were set up as controls. The mixtures were centrifuged and supernatants collected. The supernatants were buffer exchanged to RPMI as described previously and filtered through a 0.45 μm Millex-HV syringe filter (Millipore, MA, US) and stored at −70° C. until testing for monokine inducing activity in fresh, normal PBMC as described above.

Statistical Analysis

Comparisons of the means of different patient groups or different test occasions were performed using an unpaired t-test. Time to progression and survival was analyzed using the Kaplan-Meier method and Logrank test.

Comparisons between the proliferative response to PHA in different groups or at different test occasions were done on logarithmated mean values of dpm of triplicates using unpaired t-test. For the determination of the effect of addition of CHL on the proliferative response of PHA-stimulated PBMCs, a modulation index (MI) was calculated according to the following formula:

MI=log(dpm PHA+drug/dpm PHA).

Results on Immunoregulatory Mechanisms of Relevance for the Present Invention

Demonstration of Intratumoral IL-1Ra

As described above IL-1Ra is a potent inhibitor of immune stimulation/reactivity as it blocks the activity of IL-1. It is therefore of considerable importance that it is frequently expressed by tumour cells and tumour infiltrating mononuclear cells. Based on the results presented in the above, it is highly reasonable to assume that tissue bound IgG is the inducer of this cytokine. Thus either tissue bound antibodies or intra-tumorally precipitated ICs can play a major role in intra-tumoural down-regulation of the immune response. FIG. 1 shows melanoma biopsies stained for the expression of IL1Ra. Different patterns are hereby found, viz. A) tumour cells are generally stained with some positive infiltrating mononuclear cells, and B) large numbers of infiltrating cells staining for IL-1Ra, tumour cells only faintly positive.

Production of IL-1Ra in Cultures of PBMC

Production of IL-1Ra can be induced by some cytokines (Tilg et al., 1994), but FcγR cross-linking by solid phase IgG or ICs seems to be the most efficient inducer of this substance. It has been shown that in cultures where binding of IgG to the surface of the culture well is allowed (uncoated wells) the production of IL-1Ra is significantly enhanced (p<0.0001) compared to cultures where binding of IgG has been reduced by pre-coating with HSA. This immunomodulatory effect has been studied in healthy individuals, patients with malignant melanoma and renal cell carcinoma (FIG. 2). If purified human IgG is added to the HSA in coated wells (HSA/IgG), IL-1Ra production by control PBMC is restored. Based on these results it is obvious that solid phase IgG will play a major role in immune regulation.

In cultures where the wells have been pre-coated with HSA (FIG. 3A) a significant difference in IL-1Ra production was found between PBMCs from normal healthy individuals (K; n=46) and melanoma (MM1; n=43) and renal cell carcinoma patients (RCC 1; n=37) with metastatic disease (p=0.017 and p<0.008, respectively). In melanoma patients with radically resected stage III disease (MM 0; n=29) there was only a slight increase in IL-1Ra production. These results provides evidence for an immunomodulating role of cell bound IgG/ICs and that sera from cancer patients contain factors which are bound to PBMCs and are more potent in inducing IL-1Ra than serum factors from normal healthy individuals. It is reasonable to believe that this serum factor is comprised of complexed IgG. In cultures where PBMCs are exposed to solid phase serum IgG (FIG. 3B, uncoated wells) the production is significantly increased as described above and differences between healthy individuals and cancer patients are masked.

The occurrence of tissue bound IgG exposing the Fc-parts, in tumour tissue inducing production of IL-1Ra as described herein is thus highly relevant to the down-regulation of the anti-tumour immune reactivity.

Inhibition of IL-1Ra Production by Anti-CD32 Fragments.

Based on the results described above blockade of the receptor(-s) involved in the induction of IL-1Ra production is a therapeutic strategy. It is demonstrated that pre-incubation of PBMCs from normal, healthy individuals and cancer patients with an anti-CD32 Fab fragment before these cells were set up in cultures on either uncoated or HSA/IgG coated microtitre plates significantly inhibits the production of this cytokine.

TABLE 1

Effect of antibodies to FcγR II, anti-CD32 Fab, on IL-1Ra production by normal PBMC

| | | Anti-hu CD32 Fab effect on cultured PBMC on uncoated culture plates | | | Anti-hu CD32 Fab effect on cultured PBMC on HSA/IgG precoated culture plates | | |
|---|---|---|---|---|---|---|---|
| | None | Anti-hu CD32, 5 μg/ml | Anti-hu CD32, 50 μg/ml | None | Anti-hu CD32 5 μg/ml | Anti-hu CD32 50 μg/ml |
| Ctrl 1 [1)] | N.D. [4)] | N.D. | N.D. | 6275 | N.D. | 2210 |
| Ctrl 2 | 2985 [3)] | N.D. | 725 | 6620 | N.D. | 1530 |

TABLE 1-continued

Effect of antibodies to FcγR II, anti-CD32 Fab, on IL-1Ra production by normal PBMC

| | Anti-hu CD32 Fab effect on cultured PBMC on uncoated culture plates | | | Anti-hu CD32 Fab effect on cultured PBMC on HSA/IgG precoated culture plates | | |
|---|---|---|---|---|---|---|
| | None | Anti-hu CD32, 5 µg/ml | Anti-hu CD32, 50 µg/ml | None | Anti-hu CD32 5 µg/ml | Anti-hu CD32 50 µg/ml |
| Ctrl 3 | 4905 | 2380 | 560 | 3075 | 925 | 570 |
| Ctrl 4 | 6014 | N.D. | 1926 | 4969 | N.D. | 1782 |
| Ctrl 5 | N.D. | N.D. | N.D. | >10 000 | N.D. | 5824 |
| Ctrl 6 | N.D. | N.D. | N.D. | >10 000 | N.D. | >10 000 |
| Pat. 1 [2] | 4330 | 3095 | 2200 | 4195 | 1520 | 630 |
| Pat. 2 | 1180 | 700 | 685 | 1170 | 735 | 910 |
| Pat. 3 | 2870 | 1415 | 870 | 1350 | 340 | 180 |
| Pat. 4 | >10 000 | N.D. | 3260 | N.D. | N.D. | N.D. |

[1] Control PBMC from healthy donors
[2] PBMC from cancer patients
[3] IL-1Ra, pg/ml
[4] Not done
Note:
All PBMCs were pre-incubated with anti-human CD32 Fab 1.o hr, 37° C. before culturing.

Thus various strategies, which interfere with the cross-linking of the IL-1Ra inducing Fc receptor, are the base of therapeutic strategies, which will relieve immunosuppression and thereby improve the prospect for successful immunostimulating treatment.

Modulation of FcγR Activity by Protease Inhibitors

It has been demonstrated that proteolytic activity increases the reactivity of FcγRII (Isashi et al., 1998; van der Winkel et al., 1989). The proteolytic activity is enhanced in malignant tumours; thus protease inhibitors will reduce the reactivity of CD32. Herein it is demonstrated that culturing PBMCs in the presence of non-toxic concentrations of a protease inhibitor, Tosyl, resulted in a significantly reduced production of the immune inhibitory cytokine IL1Ra. Thus inhibition of intratumoural proteolytic activity offer an excellent therapeutic strategy for treating cancer. FIG. 4 shows inhibition of IL1Ra production by Tosyl. The effect of Tosyl on IL-1Ra production by is PBMC from healthy individuals (n=9) in 10% autologous sera cultured in microtiter plates pre-coated with A) HSA, and B) HSA/IgG.

Immunostimulation by FcγR Cross-Linking

It is demonstrated herein that PBMC cultured on HSA/IgG coated microtitre plates have a dramatically enhanced proliferative response to IL-2 in both normal healthy individuals and cancer patients compared to cultures in HSA coated wells. A similar effect is found when cultures, where IgG from serum in the culture medium is allowed to bind to the microtitre plates (uncoated cultures) and HSA coated cultures are compared. FIG. 5 shows IL-2 induced proliferation by PBMC from normal healthy individuals (first three bars) and PBMC from RCC patients (last three bars) cultured in 10% autologous sera on uncoated and pre-coated microtiter plates. Significant (p<0.011) difference in proliferation between PBMC from healthy individuals and RCC patients on uncoated plates.

As the same effect on IL-2 induced proliferations are seen in HSA/IgG coated cultures and uncoated cultures; this effect is due to the same mechanism. Solid phase IgG results in a broad cross-linking, which can elicit stimulation of the immune response in normal healthy individuals by eliciting a cytokine cascade including TNF-α and IL-1, which sensitises the response to IL-2 (increased numbers of receptors). This model reflects the situation when opsonised antigens or large ICs elicits an immune response. In HSA coated wells this stimulatory cross-linking can not take place, which results in a significantly lower response to IL-2. Alternatively, the difference in IL-2 induced proliferative response can be due to an immunomodulatory effect by the cross-linking per se and not a stimulatory cytokine cascade. Inhibitory signals in monocytes/macrophages might be overcome by broad cross-linking of FcγR.

In cancer patients stimulation by FcγR cross-linking (uncoated cultures) does not properly support the proliferative response to IL-2, as demonstrated above. The type of cytokines produced can be inhibitory and does not support an optimal response to IL-2. Preliminary data suggests that serum factor(-s) is of importance for the reduced response of PBMCs from cancer patients in uncoated cultures (FIG. 6).

Effect of FcγR Blockade on IL-2 Stimulated Proliferation

The stimulatory effect in HSA/IgG coated cultures is to various degree inhibited by F(ab')$_2$ Mabs directed to FcγRs, in particular to FcγR I (CD64). This can reflect the effect of small inhibitory ICs.

TABLE 2

Inhibition of IL-2 induced proliferation of PBMC with F(ab')2 monoclonal antibodies against Fc receptors.

| Anti-FcRec Mab | Coat HSA | Uncoated | Coat HSA/IgG |
|---|---|---|---|
| | Experiment 1 | | |
| None | 30 361 [1] | 65 030 | 146 337 |
| Anti-CD16 | 62 072 | 84 173 | 109 417 |
| Anti-CD32 | 35 106 | 82 628 | 126 363 |
| Anti-CD64 | 30 526 | 3 219 | 25 533 |
| | Experiment 2 | | |
| None | 16 315 [1] | 97 446 | 102 863 |
| Anti-CD16 | 10 315 | 39 023 | 97 572 |
| Anti-CD32 | 26 976 | 56 226 | 93 153 |
| Anti-CD64 | 19 634 | 35 620 | 45 858 |

[1] 3H-Thymidine uptake in counts per minute (cpm) on day 7. Mean of triplicate wells.

Background in wells without IL-2 did not exceed 750 cpm.

Flow cytometry was performed to verify binding of the F(ab')$_2$ monoclonal antibodies to PBMC. The inhibitory anti-CD64 antibodies bound to a higher percentage of monocytes that anti-CD16, but fewer to monocytes than anti-CD32 antibodies, in both experiments. Furthermore, the mean fluorescent intensity of both anti-CD16 and anti-CD32 binding was higher than anti-CD64 in both experiments. Thus, increased binding of the anti-CD64 Flab)$_2$ antibody, compared to anti-CD16 and anti-CD32 does not explain the inhibitory effect.

Effect of FcγR Cross-Linking on the Production of IL-6 in Cultures of PBMC

These results follow under the discussion of modulation of IL-6 production.

The culture model described above provides for excellent opportunities of studying immunosuppressive regulatory mechanisms in cancer patients.

Cell Bound IgG/ICs in Tumor Tissue and on PBMCs from Cancer Patients

As IC in cancer patients cause dys-regulation of the immune system, it is important, using suitable diagnostic tools, to identify patients with this kind of dys-regulation in order that patients, who are most likely to respond to therapeutic strategies based on elimination of FcγR inhibitory signals, can be selected. In this context determination of cell-bound ICs (CBIC) is the important invention as these might very well have full activity even in the absence of CIC (circulating immuno complex).

CBIC can be directly demonstrated by means of
IgG$^+$ PBMC (peripheral blood mononuclear cells)
IgG$^+$ TIMC (tumour infiltrating mononuclear cells, demonstrated in surgical or fine needle biopsies, FNA)

CBIC can also be demonstrated by means of functional parameters such as
production of O$_2$
down-regulation of the ζ-chain of TCR
down-regulation of CD80 and/or CD86
induction of IL-1Ra, demonstrated in biopsies and FNA
induction of other monokines,
whereby a number of these parameters can be demonstrated immunohistochemically.

Immune complexes (ICs) can be determined in different ways.

Standard methods for determining circulating ICs (CIC) are by indirect non-functional parameters as complement binding and activation, PEG-precipitation, phagocytosis, platelet aggregation.

Determination of CIC, to obtain prognostic information or to diagnose possible occurrence of ICs modulating the immune system, is likely to be irrelevant, as IC has to be bound to cellular receptors to have any immunomodulatory effect. Thus CBIC will have full immunomodulatory effect long before the amount of ICs is enough to saturate these receptors and ICs appear in the circulation. In the present case direct methods has been used to demonstrate the presence of cell/tissue bound IgG or ICs.

Two methods based on the binding of either a monoclonal antibody or protein G to the Fc part of IgG were used to demonstrate the occurrence of tissue bound IgG or IC. The Mab was directed to the Fc part of all subclasses of human IgG and protein G was genetically modified, binding only to the Fc part of IgG. Thus CBIC can be demonstrated using flow cytometry, or CBIC on blood cells has been demonstrated using immunocytochemistry (IHC) on cytospin preparations. Further CBIC has been demonstrated in tumour tissue (tumour cells, endothelium, tumour infiltrating inflammatory cells) using IHC.

If the immunohistochemical distribution pattern of stained IgG/IC exclusively coincides with the pattern of the low affinity receptors for IgG (CD16 and CD32) the identified substance is considered being IC. Otherwise it is not possible to discriminate between IgG and IC as the monoclonal antibody and protein G might be able to bind to monomeric IgG as well. However, if IgG is bound to the tissue directly or in IC might be of minor importance as it will anyhow be recognised as "solid phase" IgG.

Immunocytochemistry of Tumour Tissue

Several quite different staining patterns have been found in biopsies from untreated and treated melanoma metastases. In the majority of untreated and treated metastases with a poor infiltration of inflammatory cells and with no or only minor tumour regressive changes IgG was found in perivascular areas of the intra-tumoural micro-vessels. In these patients—tumours—the endothelial cells of larger vessels were stained indicating a systemic distribution of IC as endothelial only express CD32 and the bound IgG has to be in the form of complexes. FIG. 7 shows tumour biopsies stained for the presence of tissue bound IgG/IC (red) and T-lymphocytes (brown) using a double staining technique with recombinant protein G (not binding to albumin). Different staining patterns are shown, viz. A) staining of vascular areas/endothelial cells and some lymphocytes for IgG. Some lymphocytes are not stained for IgG/IC. Low numbers of tumour infiltrating mononuclear cells, B) a diffuse staining of the tumour tissue for IgG/IC, whereby the majority of the lymphocytes are not stained for IgG/IC, C) staining tumour infiltrating macrophages and some lymphocytes for IgG/IC, but tumour cells are generally negative, D) extensive staining of vascular areas for IgG/IC with very low numbers of infiltrating mononuclear cells.

These results show that tissue bound IgG exposing Fc parts, are inversely correlated to the presence of tumour infiltrating mononuclear cells and hence plays a major role in the down-regulation of the immune response to the tumour.

Immunocytochemistry of PBMC

Based on the results described above the occurrence of IC binding circulating blood cells was studied in cytospin slides stained using the two methods described. Preliminary results show that a very low frequency of positive monocytes was found in the majority of healthy individuals in contrast to patients with cancer. As monocytes from healthy individuals were generally negative the stained IgG represents IC indicated by the staining of platelets. (FIG. 8).

Chronic Inflammatory Reaction in Cancer Using IL-6 as a Marker

Chronic inflammatory reaction is often found in cancer patients. Interleukin-6 is a proinflammatory cytokine of importance for the initiation of immune reactivity (Barton, 1996; Barton, 2001). However, in cancer patients, its occurrence has a number of detrimental effects. Inflammatory cells, vascular endothelium and several types of tumour cells produce it. It has activity as autocrine growth factor in at least some malignancies, e.g., myeloma and renal carcinoma. It can interfere with the cytotoxic activity of cisplatinum (Borsellino et al., 1995; Mitzutani et al., 1995). It participates in the induction of acute phase reactants, e.g., fibrinogen and CRP. In this context it can be involved in a positive regulatory loop as the production of fibrin split products have been found to be inducers of IL-6. This is one of the cytokines, which seems to be involved in the paraneoplastic syndrome of cancer patients and high serum levels of this cytokine are often associated with poor response to immunotherapy. Besides, these cytokines are not produced in healthy individuals. In cancer patients, however, PBMCs (as shown above) are triggered to produce considerable amounts of IL-6 in vivo and continue to do so also in vitro. Except for cytokines, such as IL-18, IL-17 and TNF-α, a cross-linking of FcγR is a mechanism by which monocytes are triggered to produce IL-6. Thus, CBIC is of importance for the dys-regulation of the immune system in cancer.

Various cytokines, IL-1β, IL-6, TNF-α, PGE$_2$, TGF-8 are often increased in cancer patients. (Mocellin et al., 2001) Several of these IL-18, IL-6, and TNF-α are supposed to be involved in the paraneoplastic syndrome characterized by low-grade fever, anorexia, weight-loss, and fatigue.

An increased systemic concentration of IL-6 has been reported to correlate with a poor prognosis and poor response to chemotherapy (Borsellino et al., 1995; Mitzutani et al., 1995). Furthermore, it is well documented that patients with high IL-6 serum levels (increased CRP) can not be successfully treated with immunotherapy. (Blay et al. 1992; Deehan et al., 1994; Lissoni et al., 1999; Tartour et al., 1996).

PGE$_2$ is well known to be a potent inhibitor of immune reactivity. Thus patients with high serum levels of PGE$_2$ before treatment or having an increased production of PGE$_2$ during the early treatment period will not respond to immunotherapy. (Deehan et al., 1994)

An increased production of $O_2^-$ radicals by monocytes has been demonstrated to down-regulate the ζ-chain of the T-cell receptor resulting in a non-functional state of these cells. (Kono et al., 1996; Otsuji et al., 1996)

Therapeutic control of the dys-regulatory mechanisms of IL-6 production will thus improve quality of life, therapeutic response to immuno- and chemotherapy, and increase overall survival.

As IL-6 is only one product of the dys-regulated inflammatory reaction mentioned, and often correlates to production of the other cytokines such as IL-1β and TNF-α, the strategy is to find the fundamental dys-regulatory mechanisms and block them in order to completely down-regulate the inflammatory reaction.

IL-6 Production in Cancer Patients, Correlation to Prognosis

The present analysis includes IL-6 production from PBMCs from three types of cancer patients. As shown in Table 3, 30 patients with radically resected stage III melanoma (MM0), 43 patients with previously untreated metastatic melanoma (MM1), 36 with previously untreated metastatic renal cell carcinoma (RCC1) and 46 patients with primary colorectal cancer (CRC) were studied. The cytokine production is, compared to that of healthy individuals (K), significantly increased in all categories. It is obvious that IL-6 production is not restricted to patients with advanced disease as IL-6 is produced also by PBMCs from patients with primary colorectal cancers and radically resected stage III melanoma (MM 0), whereby in the latter group no metastatic lesions could be demonstrated by clinical or radiological investigations. A correlation between IL-6 production by PBMCs and other clinical parameters was demonstrated for colorectal cancer and renal cell carcinoma.

The serum concentration of IL-6 was determined in melanoma, colon and renal cell carcinoma patients and was generally below the detection limit of the ELISA-technique used. In only a few cases measurable amounts of IL-6 were found but these were quite negligible compared to those found in cultures.

TABLE 3

Production of IL-6 by PBMCs from healthy individuals and various types of cancer patients.

| Group | No of patients | Mean value pgIL-6/ml | +SE | t-test compared with controls |
|---|---|---|---|---|
| K | 49 | 214 | 85 | — |
| MM 0 | 30 | 2444 | 978 | p > 0.0001 |
| MM 1 | 43 | 3838 | 1279 | p > 0.0001 |
| RCC 1 | 36 | 4003 | 935 | p > 0.0001 |
| K | 12 | 379 | 133 | — |
| CRC | 46 | 5973 | 1362 | p = 0.042 |

Colorectal Cancer

As shown in FIG. 9, the IL-6 production increases with more advanced primary tumour, the difference between T2N0 and T3-4N0 achieved statistical significance after stimulation with bacterial lipopolysaccharide (LPS) (p=0.05). Also the lymph node status had an impact on the production of this cytokine with higher IL-6 production by PBMCs from patients with lymph node metastases (p=0.02). FIG. 9 shows the production of IL-6 by PBMCs from different subsets of colorectal cancer patients, viz. A), without LPS stimulation and B) with LPS stimulation.

In renal cell carcinoma IL-6 production is of prognostic significance as evident from FIG. 10. Patients that produced <2500 pg/ml IL-6 in short term cultures (n=18) showed significantly longer survival than patients that produced >2500 pg/ml (n=23).

Effect of FcγR Cross-Linking on IL-6 Production by PBMCs In Vitro

The culture conditions have a marked impact on the production of IL-6. If IgG from serum in the culture medium was allowed to bind to the surface of the culture wells, the IL-6 production was significantly lower, compared to cultures, wherein the wells were pre-coated by HSA, in about one third of the patients with malignant melanoma and colorectal cancer (both malignancies analysed together, p=0.001).

The inhibitory effect of FcγR cross-linking was further demonstrated in PBMC cultures from healthy individuals wherein the culture wells were either pre-coated with HSA/IgG or HSA alone. Also in this situation, solid phase IgG significantly reduced the production of IL-6 by PBMCs from some individuals (FIG. 11). FcγR cross-linking induced by solid phase IgG thus inhibits production of IL-6 in some patients.

The occurrence of this phenomenon in cultures with PBMCs from healthy individuals, as well, is not surprising, as this evidently is one of the normally occurring immunoregulatory mechanisms, the magnitude of which is increased in cancer patients. The difference between patients with and without this type of inhibition is evidently due to triggering of the monocytes or due to the influence of other factors. One explanation may be that a high concentration of a serum factor can induce IL-6 production despite the inhibitory action of FcγR cross-linking. At low concentrations of this factor, the inhibitory action of FcγR cross-linking will take over.

The evidence given shows the interaction of the two immunoregulatory mechanisms described herein based on the analysis of the results of the different experiments carried out.

Occurrence and characterisation of a serum factor inducing IL-6 production by PBMCs Production of IL-6 by PBMCs from in particular cancer patients in vitro, means that either are the producing cells triggered in vivo and maintain this status when placed in culture or there is a serum factor which continuously stimulates production of IL-6. In order to discriminate between these two alternatives, sera from cancer patients, with a high IL-6 production in autologous PBMC cultures, were used in the medium of five cultures with PBMCs from healthy individuals. A high IL-6 production was induced in all these cultures demonstrating occurrence of an IL-6 inducing serum factor.

TABLE 4

IL-6 inducing activity in sera from cancer patients cultured with PBMCs from healthy individuals with blood group 0.

| Sera | IL-6, pg/ml |
|---|---|
| Patient 1 | 13129 |
| Patient 2 | 2440 |
| Patient 3 | 5313 |

TABLE 4-continued

IL-6 inducing activity in sera from cancer patients cultured with PBMCs from healthy individuals with blood group 0.

| Sera | IL-6, pg/ml |
|---|---|
| Patient 4 | 4951 |
| Patient 5 | 25276 |
| Control 1[1)] | 31.2 |
| Control 2 | 31.2 |
| Control 3 | 31.2 |
| Patient 6[2)] | 115 |
| Patient 7[2)] | 31.2 |

[1)] Control from healthy individuals
[2)] Sera from patients who did not produce IL-6 in vitro
None of the control PBMC made detectable amounts IL-6 when cultured with autologous, normal sera.

Effect of ProteinG-Sepharose Affinity Chromatography of Sera on IL-6 Inducing Activity As cancer patients have an increased incidence of CIC and as it has been shown that cross-linking of FcγR can induce IL-6 production by monocytes, the IgG fraction was removed from these sera using affinity chromatography with proteinG-Sepharose. When sera treated in this way were tested in cultures with PBMCs from the same healthy individuals, the IL-6 production was not only maintained but also even increased.

TABLE 5

Effect of ProteinG-Sepharose affinity chromatography of sera on IL-6 inducing activity

| | Autologous sera | | Patient sera 1 (CC[1]) | | Patient sera 2 (CC) | | Patient sera 3 (MM[2]) | |
|---|---|---|---|---|---|---|---|---|
| | — | Prot G | — | Prot G | — | Prot G | — | Prot G |
| Control PBMC 1 | <31.2[3] | N.D.[4] | 5313 | 8599 | 4951 | 12648 | | |
| Control PBMC 2 | <31.2 | N.D. | 9551 | 15243 | 13099 | 18618 | | |
| Control PBMC 3 | <31.2 | <31.2 | | | | | 25276 | 30316 |
| Control PBMC 4 | <31.2 | <31.2 | | | | | 11342 | 12806 |

[1] CC = colon carcinoma
[2] MM = malignant melanoma
[3] pg/ml of IL-6
[4] N.D. = not done
Patient sera 3 did not contain detectable, endogenous IL-6. Patient sera 1 and 2 were not tested for endogenous IL-6.

Thus, CIC are not involved in inducing IL-6 production, but either CIC or IgG obviously modulate the production as it increased when IgG was removed from the culture medium. This is compatible with the results above where FcγR cross-linking by solid phase IgG inhibited IL-6 production. When IgG is removed from the culture medium, the inhibitory effect is relieved. Affinity chromatography with proteinG-Sepharose had no effect on control sera not inducing IL-6 production. Determination of IgG after affinity chromatography did not find detectable amounts of IgG (<0.01 mg/ml).

Characterisation of IL-6 inducing factor (IL-6IF) by ultrafiltration In order to confirm that CIC are not the inducer of IL-6 production by PBMCs in cancer patients and also to further characterise the IL-6 inducing factor, sera from cancer patients and healthy individuals were diluted (1:5) and ultrafiltered with a filter cut-off at 100, 50 and 3 kD. In some analyses only a factor with a molecular weight of less than 50 kD was identified, whereas in others IL-6IF was at least to some extent also found in the other fractions, but this activity could always be demonstrated in the less than 50 kD fraction. IL-6 inducing activity was generally not found in the fraction with a molecular weight of less than 3 kD. These results show that IL-6IF has a low molecular weight and thus IgG or CIC can not be involved. The occurrence of this factor in some experiments, also in fractions having a molecular weight >50 kD, indicates either that the IL-6 inducing, activity can depend on molecules of different sizes or that a small factor is bound to other serum proteins. The former case is compatible with the assumption that this factor is a proteolytic fragment of some large molecule, and that the activity is present in fragments of different sizes. If the IL-6IF were a small fragment it is certainly likely that it is bound to other serum proteins as it would otherwise immediately be excreted in the urine.

TABLE 6

Activity of ultrafiltered serum fractions

Activity of ultrafiltered serum fractions from cancer patients that previously had a stimulating effect on autologous cells and control serum from healthy individuals

| | unfiltered | <50 kD [1)] | <3 kD |
|---|---|---|---|
| Control sera 1 [2)] | <31.2 [3)] | 461 | 101 |
| Control sera 2 | <31.2 | 394 | 40 |
| Control sera 3 | <31.2 | 74 | 42 |
| Patient sera 1 [4)] | <31.2 | 1264 | 43 |
| Patient sera 2 | <31.2 | 1404 | <31.2 |
| Patient sera 3 | 34 | 212 | <31.2 |

TABLE 6-continued

Activity of ultrafiltered serum fractions

Activity of ultrafiltered serum fractions from cancer patients that previously had a stimulating effect on autologous cells and control serum from healthy individuals

| | unfiltered | <50 kD [1)] | <3 kD |
|---|---|---|---|
| Patient sera 4 | 13 129 | 9480 | N.D. [5)] |
| Patient sera 5 | 2440 | 986 | N.D. |

[1)] Size of ultrafiltered proteins
[2)] Control serum from healthy individuals
[3)] IL-6, pg/ml
[4)] Serum from cancer patients with malignant melanoma
[5)] N.D. = not done
(Note:
All serum fractions were cultured with PBMC from healthy individuals with blood group 0. None of the serum fractions had IL-6 activity when cultured without PBMC)

The fractions obtained during ultrafiltration of sera described above were also analysed using PAGE electrophoresis of reduced proteins. In the fractions with the highest IL-6 activity a band having a molecular weight of about 20 kD was identified. This was either very weak or not present in all fractions of control sera or patient sera with no IL-6 inducing activity.

Affinity Chromatography of Serum Using Gelatine-Sepharose

To further characterise the IL-6IF and also to demonstrate a possible similarity to the "immunosuppressive factor" described by others (Easter et al., 1988; Hoyt et al., 1988) its binding to gelatine-Sepharose was studied. Despite a surplus of the binding gel, IL-6 inducing activity was not reduced when serum, prepared in this way was tested in cultures with control cells.

IL-6 Inducing Activity in Urine

As IL-6IF was found to have a molecular weight of less than 50 kD, it is assumed that this factor will at least, to some extent be excreted in the urine. Thus the less than 50 kD fraction was prepared and concentrated using the 3 kD filter. When these fractions from cancer patients were tested for IL-6 production in cultures with PBMCs from healthy individuals an IL-6 inducing activity was found.

TABLE 7

IL-6 inducing activity in ultrafiltered fractions (3 to 50 kD) from urine of cancer patients and healthy individuals

| Urine from | Control PBMC 1 | Control PBMC 2 | Control PBMC 3 | Control PBMC 4 |
|---|---|---|---|---|
| Patient 1 (RCC [1]) | 1053 [2] | | | |
| Patient 2 (RCC) | | >2000 | | |
| Patient 3 (RCC) | | 1716 | | |
| Patient 4 (RCC) | | >2000 | | |
| Patient 5 (MM [3]) | | >2000 | | |
| Control 1 | | | 698 | 291 |
| Control 2 | | | — | 497 |

[1] RCC = Renal cell carcinoma
[2] IL-6, pg/ml
[3] MM = malignant melanoma
None of the control PBMCs produced detectable amounts (<31.2 pg/ml) of IL-6 when cultured without urine fractions.

The identification of IL-6IF, or any other inducing factor of an immunoregulatory substance, in the urine opens interesting diagnostic and therapeutic possibilities. When concentration of IL-6IF of urine is related to the serum concentration a simple diagnostic test is made which provides essential information about prognosis and the likelihood of therapeutic success. The diagnosis will also be of value to determine treatment strategies dealing with the elimination of IL-6IF-treatment of the chronic inflammatory reaction in cancer patients.

IL-6 Inducing Activity in Tumour Extracts

The origin of IL-6IF is so far unknown. However, it is related to the presence of a malignant tumour. The observation that IL-6IF has a low molecular weight is compatible with its being an enzymatic fragment of some large molecule. It is assumed that this factor is produced in the tumour or by substances released from the tumour. In order to verify this, tumours were minced using a stainless steel mesh and extracted in physiological buffer during various times. In fact, 5 out of 7 analysed tumours produced the factor when the extracts were tested in cultures of PBMCs from healthy individuals. These findings are in agreement with the increased enzymatic activity of tumours as well as the poor prognosis of patients with a high expression of several proteolytic enzymes.

TABLE 8

IL-6 inducing activity in extracts from frozen tumour biopsies and fresh tumour

| Tumour extracts | IL-6 produced by control PBMC |
|---|---|
| CC 1 | 564[1] |
| MM1 | 313 |
| RCC1 | <31.2 |
| RCC 2 | <31.2 |
| RCC 3 | 1078 |
| RCC 4 | 1025 |
| RCC 5[2] | 1554 |

[1] pg/ml
[2] Fresh biopsy
None of the tumour extracts contained detectable endogenous IL-6 activity
None of the control PBMCs produced detectable amounts of IL-6 when cultured in autologous sera without tumour extracts.
All control PBMCs produced >1200 pg/ml of IL-6 when cultured in the presence of Lipopolysaccharide (LPS).

IL-6 Inducing Activity in Conditioned Culture Media from Tumour Cell Lines

Immunomodulating factors have been identified in large numbers at studies of either tumour extracts or conditioned culture media from tumour cell lines. It has now turned out that IL-6IF is produced by squamous cell carcinomas from the oral cavity. Conditioned media were collected and tested using PBMCs from healthy individuals as described. An IL-6 inducing activity was demonstrated and this will facilitate studying therapeutic possibilities such as reduction of IL-6IF by inhibiting different types of tumour related enzymes, such as MMPIs.

TABLE 9

IL-6 inducing activity in ultrafiltered (3 to 50 kD) condition media from a squamous cell carcinoma (SCC) cell line grown in media with fetal calf serum (FCS) or pooled human AB-sera from two different batches AB7, and AB8, respectively.

| Conditioned media | Control PBMC 1 | Control PBMC 2 | Control PBMC 3 | Control PBMC 4 | Control PBMC 5 | Control PBMC 6 | No PBMC (endogenous activity) |
|---|---|---|---|---|---|---|---|
| UT-SCC-10 in FCS | 1559 [1] | 925 | | | | | <31.2 |
| Media FCS, no cells | 221 | <31.2 | | | | | <31.2 |
| UT-SCC-10 in AB7 | | | >2000 | 1753 | | | 287 |
| Media AB7, no cells | | | 939 | 718 | | | <31.2 |
| UT-SCC-10 in AB 8 | | | | | 3043 | 6821 | <31.2 |

TABLE 9-continued

IL-6 inducing activity in ultrafiltered (3 to 50 kD) condition media from a squamous cell carcinoma (SCC) cell line grown in media with fetal calf serum (FCS) or pooled human AB-sera from two different batches AB7, and AB8, respectively.

| Conditioned media | Control PBMC 1 | Control PBMC 2 | Control PBMC 3 | Control PBMC 4 | Control PBMC 5 | Control PBMC 6 | No PBMC (endogenous activity) |
|---|---|---|---|---|---|---|---|
| Media AB8, no cells | | | | | <31.2 | 2975 | <31.2 |

[1] IL-6, pg/ml

Similar to the situation with IL-6 we have also found inducing activity for TNF-□ and IL-1β (Table 10) and IL-10 in serum and ultrafiltered urine. IL-10 was found in four sera/serum fractions and one urine fraction also inducing IL-6. In addition, one serum and one urine fraction inducing IL-6 did not induce IL-10.

TABLE 10

TNF-α and IL-1β inducing activity in IL-6 inducing serum and ultrafiltered urine from cancer patients

| Source | Control PBMC | IL-6 pg/ml | TNF-α pg/ml | IL-1β00 pg/ml |
|---|---|---|---|---|
| Patient serum 1 | None | <31.3 | N.D. | N.D. |
| Patient serum 1 | PBMC 1 | 13129 | 1774 | 414 |
| Patient serum 2 | None | <31.2 | 86 | 8 |
| Patient serum 2 | PBMC 2 | 153 | 153 | 14 |
| Patient serum 2 | PBMC 3 | 2440 | 762 | 136 |
| Patient urine 1 | None | <31.2 | <31.2 | <7.8 |
| Patient urine 1 | PBMC 4 | >2000 | 123 | 147 |
| Patient urine 1 | PBMC 5 | >2000 | 199 | 128 |
| Patient urine 2 | None | <31.2 | <31.2 | <7.8 |
| Patient urine 2 | PBMC 4 | >2000 | 166 | >500 |
| Patient urine 2 | PBMC 5 | >2000 | 582 | >500 |

N.D. = not done
None of the control PBMCs made detectable levels of IL-6, TNF-α or IL-1β, when cultured in autologous serum.

Possibility to Predict Therapeutic Response to Drug Therapy of Cancer Based on Induction of Cytokines.

We have previously shown that an immune status that correlates to response to immunotherapy can be identified by analysing the effect of immunomodulating drugs on PHA stimulated PBMCs from renal cell carcinoma patients. An increased proliferation in cultures where cimetidine is added identifies responders to interferon-alpha and a reduced proliferative response to chlorambucil identifies responders to interleukin-2 (FIG. 12). Now we demonstrated that there is a correlation between the effect of chlorambucil on the proliferative response to PHA and on the production of TNF-α in this type of cultures (FIG. 13). Thus, in non-responders TNF-α production is more stimulated than in responders. This opens up the possibility to analyse the pattern of inducing factors for these two subsets of patients and thereby identify responders to immunotherapy.

Characterisation of Dysregulating Factors

Analysis of Cytokine Inducing Factors in Urine

As described above factors inducing IL-1β, IL-6, IL-10 and TNF-α have been identified in the 3-30 kD fraction in tumour extracts, conditioned culture media from cancer cell lines, and cancer patient sera and urine. These urine factors were further characterised by using 2D-gel electrophoresis and identified after fragmentation using masspectrometry and N-terminal sequence analysis.

Comparison Between Healthy Controls and Cancer Patients

Comparisons were made between a pool of 11 healthy controls (control pool) and four individual controls and 1. a pool of one breast and one pancreas cancer patient, 2. a pool of two renal cell carcinoma patients and 3. three individual melanoma patients.

Proteins or fragments of proteins found in the urine fraction from different types of cancer patients but not in healthy controls are shown in Table 11. Some proteins/fragments were found in the urine of several different cancer patients, e.g. albumin/albumin fragments, CD59, plasma retinol binding protein and prostaglandin D2 synthase

TABLE 11

Proteins/protein fragments found in urine fractions from cancer patients, but not in the pool of healthy controls

| Proteins | Breast/pancreas cancer | Renal cell carcinoma | Malignant melanoma |
|---|---|---|---|
| Albumin fragments | | | X |
| Albumin fragments | | | X |
| Albumin fragments | | | X |
| Albumin fragments | | | X |
| Albumin fragments | | | X |
| Albumin fragments | X | | |
| Albumin fragments | X | | |
| Albumin fragments | X | | |
| Albumin fragments | X | | |
| Albumin fragments | X | | |
| Albumin fragments | X | | |
| Albumin fragments | X | | |
| Albumin fragments | X | | |
| Alpha-amylase, pancreatic chain 1 | X | | |
| Beta microsemino protein | | | X |
| CD59 | X | X | X |
| Extracellular superoxide dismutase | | | X |
| Heparan sulphate proteoglycan (Perlecan) | X | | |
| Immunoglobulin gamma 1 chain, C region | X | | |
| Immunoglobulin kappa light chain, C region | X | | |
| Immunoglobulin kappa light chain, C region | X | | |
| Immunoglobulin kappa light chain, C region | X | | |
| Immunoglobulin kappa light chain, C region | X | | |
| Immunoglobulin kappa light chain, C region | X | | |
| Inter-alpha-trypsin-inhibitor, fragment of chain 2 | X | | |
| Lithostathine 1 alpha | | | X |

TABLE 11-continued

Proteins/protein fragments found in urine fractions from cancer patients, but not in the pool of healthy controls

| Proteins | Breast/pancreas cancer | Renal cell carcinoma | Malignant melanoma |
|---|---|---|---|
| Plasma retinol binding protein | | X | X |
| Prostaglandin D2 synthase | X | X | X |
| Secreted LY-6/uPar related protein/Anti-neoplastic urinary protein | X | | |
| Splice isoform 2 of tropomysin alpha 3 chain | | | X |
| Zinc-alpha-2-glycoprotein, fragment of chain 3 | X | | |

Comparison Between Urine Fractions with and without IL-6 Inducing Activity

In order to further characterise and identify the cytokine inducing factors, comparisons were made between urine samples from melanoma patients with and without IL-6IF activity. As shown in Table 12 several fractions were present in considerably higher amount in urine with IL-6 inducing activity.

TABLE 12

Comparison between melanoma patients with and without IL-6 inducing activity.
Proteins over represented in urine fraction from patient with IL-6 inducing activity

| Protein spot on 2D gel | Protein/protein fragment analysed by masspectometry | Alternative protein/s according to masspectormetry analysis |
|---|---|---|
| 1 | Beta-microsemino protein | |
| 2 | CD59 | |
| 3 | CD59 | |
| 4 | CD59 | |
| 5 | Colipase | Inhibin beta |
| 6 | Extracellular superoxide dismutase | |
| 7 | Heparan sulphate proteoglycan (Perlecan) | |
| 8 | Immunoglobulin kappa light chain | |
| 9 | Immunoglobulin superfamily member 8 | LIR-D1 precursor |
| 10 | IL-13 receptor alpha-1 chain | Urokinase plasmin activator surface |
| 11 | Inter-alpha-trypsin inhibitor, chain 2 | Endoplasmic reticulum protein ERP29 |
| 12 | Lithostathine 1 alpha | |
| 13 | Lithostathine 1 alpha | |

Analyses of urine fractions before and after adsorption with PBMCs Identification of inducing factors was next done in two experiments by adsorbing urine, containing IL-6IF, with purified PBMCs from healthy controls. The cells chosen for adsorption were shown to be stimulated to produce IL-6 by these urine fractions. The IL-6 inducing activity was significantly reduced by the adsorption procedure (Table 13).

TABLE 13

IL-6 and TNF-alpha inducing activity in adsorbed and unabsorbed urine fractions

Urine fraction pooled from two renal cell carcinoma patients

| Urine fraction added to control PBMCs | IL-6 | | | TNF-alpha | | |
|---|---|---|---|---|---|---|
| | Control PBMC 1 | Control PBMC 2 | Control PBMC 3 | Control PBMC 1 | Control PBMC 2 | Control PBMC 3 |
| None | <31.2 [1] | 392 | <31.2 | <31.2 | 225 | 67 |
| Unadsorbed | 778 | 942 | 1433 | 74 | 207 | 179 |
| Adsorbed | 311 | 1031 | 620 | <31.2 | 59 | 49 |

Urine fraction from a patient with malignant melanoma

| Urine fraction added to control PBMCs | IL-6 | | | TNF-alpha | | |
|---|---|---|---|---|---|---|
| | Control PBMC 4 | Control PBMC 5 | Control PBMC 6 | Control PBMC 4 | Control PBMC 5 | Control PBMC 6 |
| None | 167 | <31.2 | <31.2 | 94 | 121 | <31.2 |
| Unadsorbed | >2000 | >2000 | 55 | 348 | 531 | 38 |
| Adsorbed | 1187 | 1365 | <31.2 | 78 | 203 | <31.2 |

[1] pg/ml
The urine fractions did not contain endogenous IL-6 or TNF-alpha.

In agreement with this, several proteins disappeared or were found in significantly reduced amounts in the adsorbed fractions as shown in 2D-gel electrophoresis (FIGS. 14 and 15). Reduction in the amount of the proteins was recorded visually and confirmed using densitometry. Adsorbed proteins were identified using masspectrometry. In addition the amino acid sequence of nine proteins/fragments was determined using the Edman sequencing technique. The identified proteins are shown in Table 14 and 15. Amazingly, the majority of these fractions were found to be fragments of normally occurring proteins, such as IgG, β2-microglobulin and serum albumin.

TABLE 14

Proteins/protein fragments adsorbed from an IL-6-inducing urine fraction pooled from two patients with renal cell carcinoma by purified normal PBMC.

| Spot | Protein | Sequenced | Fragment starting with position |
|---|---|---|---|
| 1 | Albumin fragment | No | NA |
| 2 | Albumin fragment | No | NA |
| 3 | Albumin fragment | No | NA |
| 4 | Albumin precursor | Yes | 253 |
| 5 | Albumin precursor | Yes | 253 |
| 6 | Albumin precursor | Yes | 253 |
| 7 | Albumin precursor | Yes | 517 |
| 8 | Albumin precursor | Yes | 101 |
| 9 | Alpha-1-microglobulin | Yes | 21 |
| 10 | Alpha-1-microglobulin | Yes | 21 |
| 11 | Beta-2-microglobulin | Yes | 22 |
| 12 | Beta-2-microglobulin | Yes | 47 |
| 13 | IgG kappa light chain | No | NA |
| 14 | IgG kappa light chain | No | NA |
| 15 | IgG kappa light chain | No | NA |
| 16 | Zinc-alpha-2-glycoprotein | No | NA |

NA = Not applicable

TABLE 15

Proteins/protein fragments adsorbed from an IL-6-inducing urine fraction from a patient with malignant melanoma by purified normal PBMC.

| Spot | Protein | Alternative protein/s according to mass spectometry analysis |
|---|---|---|
| 1 | Colipase chain 1 | Inhibin beta B chain |
| 2 | CD59 | |
| 3 | Extracellular superoxide dismutase | |
| 4 | IL-13 Receptor alpha chain 1 | Urokinase plasminogen activator |
| 5 | Similar to cytokeratin 8 | IgG heavychain v region, Cell division protein kinase, GMP reductase 2, Vacuolar protein sorting 26 |
| 8 | Tumor endothelial marker 1 precursor | |

As these fragments were identified based on their adsorption to PBMCs, demonstrating a high degree of binding, the occurrence of receptors for these protein fragments/peptides on normal PBMCs sensitive to IL-6IF can be postulated. As albumin and β2-microglobulin do not normally bind to these cells, it can be further postulated that fragmentation of these proteins results in conformational changes exposing new structures with a specific binding to receptors on PBMCs. As demonstrated herein this results in modulation of the immune system. Thus, the basis for a quite new mechanism of immunomodulation in diseases characterised by a high proteolytic activity, e.g. inflammation and cancer, has been discovered.

In conclusion, a large number of fragments, which were not consistently present in urine from healthy control persons, were found in urine from cancer patients. A difference in low molecular weight urine fragments was found between two patients, the urine of whom was either IL-6 inducing or not. This might reflect a significant difference in tumour related proteolytic activity in these two patients. Furthermore, several of these fragments could be adsorbed by PBMCs and different fragments were adsorbed in the two experiments presented herein, again indicating a difference in tumour related proteolytic activity between different patients. As a large number of fragments are generated the further characterisation of dysregulatory inducing factors was done using preparative proteomics, allowing determination of functional activity during preparation, that is after isoelectric focusing and preparative gel-electrophoresis.

Fragmentation of IgG and Serum Albumin Using Matrix Metalloproteinases (MMP)

Based on the results described above on the binding of IgG and albumin fragments to PBMCs, IgG or serum albumin was incubated with MMPs under well-defined conditions. Two different buffer systems were used in these experiments (FIG. 16). The supernatants were analysed using gel-electrophoresis and their cytokine inducing activity was analysed in cultures with normal PBMCs. As demonstrated in FIG. 16 several MMPs released fragments of IgG and serum albumin, which induced or modulated IL-6 inducing production. In particular, MMP-1, -2, -3, -13 released active fragments from albumin and MMP-2, -3, -7 and -13 from IgG.

Immunomodulating Activity of Extracellular Matrix Substance (ECM) Fragments

In another experiment, fragments of an extra cellular matrix substance, collagen, was added to IL-2 stimulated cultures of PBMCs from healthy donors. Commercially available collagen contained a large number of fragments and these fragments were found to have a strongly inhibitory effect on IL-2 induced proliferation (FIG. 17).

Extraction of Cytokine Inducing Factors from Tumour Tissue

We have, in this document, described that IL-6IF can be extracted from malignant tumours, e.g. malignant melanoma, renal cell carcinoma, colorectal cancer. These results were confirmed in a new series of experiments, where homogenised tumours were washed three times in PBS or RPMI in order to collect cytokine inducing factors already present in the tumours, so called "preformed inducing factors" (PIF).

The occurrence of cytokine inducing factors in these washings was determined in short term cultures with normal PBMCs. As shown in Table 16, a high IL-6 inducing activity was repeatedly found in the PIF-fractions. These fractions were then further analysed using isoelectric focusing and preparative electrophoresis.

TABLE 16

Induction of IL-6 production in PBMCs from healthy blood donors by factor/s extracted from homogenised tumours by RPMI, so called preformed inducing factors, PIF. Two PIF fractions were tested on PBMCs from 9 and 14 controls, respectively. As can be seen, these fractions efficiently induce production of IL-6 whereas cultures with the buffer, RPMI, alone showed no or only a very low inducing activity.

| PIF preparation | Control PBMCs | IL-6 production (pg/mL) | | |
|---|---|---|---|---|
| | | RPMI | RPMI + LPS | RPMI + PIF |
| 1 | 1 | <6.25 | >400 | >400 |
| 1 | 2 | <6.25 | >400 | >400 |
| 1 | 3 | <6.25 | >400 | >400 |
| 1 | 4 | <6.25 | >400 | >400 |
| 1 | 5 | <6.25 | >400 | >400 |
| 1 | 6 | <6.25 | >400 | >400 |
| 1 | 7 | <6.25 | >400 | >400 |
| 1 | 8 | <6.25 | >400 | >400 |
| 1 | 9 | <6.25 | >400 | >400 |
| 2 | 10 | <6.25 | >400 | >400 |
| 2 | 11 | 14 | >400 | >400 |
| 2 | 12 | 35 | >400 | >400 |
| 2 | 13 | 13 | >400 | >400 |
| 2 | 14 | <6.25 | >400 | >400 |
| 2 | 15 | <6.25 | >400 | >400 |
| 2 | 16 | <6.25 | >400 | >400 |
| 2 | 17 | <6.25 | >400 | >400 |
| 2 | 18 | 20 | >400 | >400 |
| 2 | 19 | 217 | >400 | >400 |
| 2 | 20 | 38 | >400 | >400 |
| 2 | 21 | 21 | >400 | >400 |
| 2 | 22 | 14 | >400 | >400 |
| 2 | 23 | 109 | >400 | >400 |

Release of Cytokine Inducing Factors by Incubation of Homogenised, Washed Tumour Tissue with MMPs In order to reduce the amount of preformed cytokine inducing factors (PIFs) present in the tumours, tissue sections/homogenates were thoroughly washed before addition of proteolytic enzymes, such as MMPs. The tumour sections/homogenates were then incubated for 20 hours at 37° C. IL-6 inducing activity of the supernatants was then analysed in cultures of normal PBMCs. As shown in FIG. 18, addition of MMP-2 modulated the release of IL-6 inducing activity. In gel electrophoresis of these supernatants, the albumin band was found to be better preserved in incubations, to which MMP-2 was added. This is reasonably due to an effect of MMP-2 on the degradation of enzymes degrading albumin. It can thus be concluded that MMPs can degrade tumour tissue substances into fragments with cytokine inducing activity. The effect of MMP-2 on the preservation of albumin in these incubations also demonstrates that proteolytic enzymes are involved in the regulation of the intra-tumoural proteolytic activity. A complex interaction of proteolytic enzymes is thus demonstrated and this results in generation and/or modulation of the production of dysregulatory inducing factors.

Increased Production of Cytokine Inducing Factors by Addition of IgG or Serum Albumin to Washed Tumour Homogenates/Tissue Sections.

In order to further explore the nature of immunomodulating substances/fragments in tumours and based on the observation, mentioned above, that fragments of albumin, IgG and β2-microglobulin efficiently binds to normal PBMCs, we added albumin or IgG to thoroughly washed tumour sections/homogenates and incubated for 18-22 h at 37° C. It was then found that addition of IgG and in particular albumin markedly increased the production of cytokine inducing factors as determined in PBMC cultures (FIG. 19). In order to rule out that the effect of adding albumin to these incubations was due to a protective action, such as reducing loss because of proteolytic degradation or binding to plastic surfaces, albumin was added to fresh PIF-fractions and incubated at 37° C. for 18 h. Compared to parallel incubations with no addition of albumin, the IL-6 inducing activity was lower when albumin was added, which shows that the markedly increased IL-6 inducing activity after adding albumin to washed homogenates is not due to any protective activity of albumin but rather that albumin acts as a substrate for intra-tumoural proteolytic enzymes. Thus it is demonstrated that immuno-modulating IgG and albumin fragments are produced in the intra-tumoural milieu.

Based on our previous results it might seem somewhat amazing that incubation of PBMCs with IgG fragments results in an increased production of IL-6 as pre-coating of culture plates with IgG from serum or an albumin/IgG mixture inhibited IL-6 production. A reasonable explanation to this apparent discrepancy in effect is that the IgG fragments manage to block the inhibitory effect natural IgG. Thus resulting in an enhanced pathological production of IL-6. This opens up interesting possibilities to modulate FcR mediated immune regulation.

Analysis and Characterisation of Immunomodulating Factors in Tumour Extracts Using "Preparative Proteomics"

Further analysis of PIF-fractions by isoelectric focusing and preparative electrophoresis has identified two fractions with IL-6 inducing activity, with different pI. Preparative electrophoresis also identified two fractions, of different molecular weight, with activity.

| ABBREVIATIONS | |
|---|---|
| ALP; | Alkaline phosphatase |
| APC; | Antigen presenting cell |
| BSA; | Bovine serum albumin |
| BSS; | Hank's balanced salt solution |
| CBIC; | Cell bound immune complex |
| CIC, | Circulating immune complex |
| ConA; | Concanavalin A |
| CRC; | Colorectal carcinoma |
| CRP; | C-reactive protein |
| CTL; | Cytotoxic T-lymphocyte |
| DAB; | 3,3'-Diaminobenzidine |
| ECM; | Extracellular matrix |
| ELISA; | Enzyme linked immunosorbent assay |
| ESR; | Erythrocyte sedimentation rate |
| FcR; | Fc receptor |
| GAH; | Goat anti-human IgG antibody |
| HSA; | Human serum albumin |
| IC; | Immune complex |
| IHC; | Immunohistochemistry |
| ICAM-1; | Intracellular adhesion molecule-1 |
| IL-1β; | Interleukin-1β |
| IL-4; | Interleukin-4 |
| IL-6; | Interleukin-6 |
| IL-10; | Interleukin-10 |
| IL-12; | Interleukin-12 |
| IL-17; | Interleukin-17 |
| IL-1Ra; | Interleukin-1 receptor antagonist |
| IL-6IF; | Interleukin-6 inducing factor |
| LPS; | Lipopolysaccharide |
| MHC 1; | Major histocompatibility complex 1 |
| MM; | Malignant melanoma |
| MMP; | Metalloprotease |
| NK-cell; | Natural killer cell |
| PAP; | Peroxidase anti-peroxidase |
| PBMC; | Peripheral blood mononuclear cell |
| PBS; | Phosphate buffered saline |
| PFA; | Paraformaldehyde |
| PGE2; | Prostaglandin $E_2$ |
| PHA; | Phytohemagglutinin A |

-continued

ABBREVIATIONS

| | |
|---|---|
| RCC; | Renal cell carcinoma |
| RIA; | Radioimmuno assay |
| RtPCR; | Reverse transcriptase polymerase chain reaction |
| SBR; | Serum blocking factors |
| TAA; | Tumour associated antigen |
| TAM; | Tumour infiltrating macrophage |
| TBS; | Tris buffered saline |
| TGF-β; | Transforming growth factor beta |
| Th1; | T helper 1 |
| Th2; | T helper 2 |
| TIL; | Tumour infiltrating lymphocyte |
| TIMC; | Tumour infiltrating mononuclear cell |
| TNFα; | Tumour necrosis factor α |

References

Arend W P, Malyak M, Guthridge C J, Gabay C. 1998. Interleukin-1 receptor antagonist: Role in biology. Annu Rev Immunol 16:27-55.

Baldwin R W, Robins R A. 1976. Factors interfering with immunological rejection of tumours. Br Med Bull 32:118-123.

Bansal S C, Bansal B R, Boland J P. 1976. Blocking and unblocking serum factors in neoplasia. Curr topics Microbiol Immunol 75: 45-76.

Barton B E. 1996. The biological effects of interleukin 6. Med Res Rev 16:87-109.

Barton B E. 2001. IL-6-like cytokines and cancer cachexia: consequences of chronic inflammation. Immunol Res 23:41-58.

Beezhold D H. Personius C. 1992. Fibronectin fragments stimulate tumour necrosis factor secretion by human monocytes. J Leuk Biol 51:59-64.

Berger 5, Ballo H, Stutte H J. 1996. Immune complex-induced interleukin-6, interleukin-10 and prostaglandin secretion by human monocytes: a network of pro- and anti-inflammatory cytokines dependent on the antigen:antibody ratio. Eur J Immunol 26:1297-1301.

Blay J Y, Negrier S, Combaret V, Attali S, Goillot E, Merrouche Y, Mercatello A, Ravault A, Tourani J M, Moskovtchenko J F, et al. 1992. Serum level of interleukin 6 as a prognosis factor in metastatic renal cell carcinoma. Cancer Res 52:3317-22.

Blay J Y, Rossi J F, Wijdenes J, Menetrier-Caux C, Schemann S, Negrier S, Philip T, Favrot M. 1997. Role of interleukin-6 in the paraneoplastic inflammatory syndrome associated with renal-cell carcinoma. Int J Cancer 72:424-30.

Borsellino N, Belldegrun A, Bonavida B. 1995. Endogenous interleukin 6 is a resistance factor for cis-diamminedichloroplatinum and etoposide-mediated cytotoxicity of human prostate carcinoma cell lines. Cancer Res 55:4633-9.

Bowles Goldsmith E, Erickson B W, Thompson N L. 1997. Synthetic peptides from mouse Fc receptor (MoFcγRII) that alter the binding of IgG to MoFcγRII. Biochemistry 36: 952-9.

Deehan D J, Heys S D, Simpson W G, Broom J, Franks C, Eremin O. 1994. In vivo cytokine production and recombinant interleukin 2 immunotherapy: an insight into the possible mechanisms underlying clinical responses. Br J Cancer 69: 1130-5.

Deo Y M, Graziano R F, Repp R, van de Winkel J G J. 1997. Clinical significance of IgG Fc receptors and FcγR-directed immunotherapies. Immunol Today 18:127-135.

Dinarello C A. 1997. Induction of Interleukin-1 and Interleukin-1 receptor antagonist. Semin Oncol 24: S9-81-S9-93.

Easter D W, Hoyt D B, Ozkan A N. 1988. Immunosuppression by a Peptide from the Gelatin Binding Domain of Human Fibronectin. J Surg Res 45:370-375.

Fridman W H, Teillaud J-L, Bouchard C, Teillaud C, Astier A, Tartour E, Galon J, Mathiot C, Sautes. 1993. Soluble Fcγ receptors. J Leuk Biol 54:504-512.

Gearing A J H, Thorpe S J, Miller K, Mangan M, Varley P G, Dudgeon T, Ward G, Turner C, Thorpe R. 2002. Selective cleavage of human IgG by the matrix metalloproteinases, matrilysin and stromelysin. Immunol Lett 81:41-48.

Gadducci A, Cosio S, Fanucchi A, Genazzani A R. 2001. Malnutrition and cachexia in ovarian cancer patients: pathophysiology and management. Anticancer Res 21:2941-7.

Geissmann F, Launay P, Pasquier B, Lepelletier Y, Leborgne M, Lehuen A, Brousse N, Monteiro R C. 2001. A subset of human dendritic cells expresses IgA Fc receptor (CD89), which mediates internalization and activation upon cross-linking by IgA complexes. J Immunol 166:346-52.

Gessner J E, Heiken H, Tamm A, Schmidt R E. 1998. The IgG Fc receptor family. Ann Hematol 76:231-48.

Ghafouri B. Stahlbom B, tagesson C, Lindahl M. 2002. Newly identified proteins in human nasallavage fluid from non-smokers and smokers using two-dimensional gel electrophoresis and peptide mass fingerprinting. Proteomics 2:112-120.

Goldin A, Nicolin A Bonmassar E. 1980. Chemoteraphy immunogenicity. Recent Results Cancer Res 75:185-94.

Gupta R K, Morton D L. 1981. Possible clinical significance of circulating immune complexes in melanoma patients. In Saunders, Serrou, Rosenfeld and Denney eds. Fundamental mechanisms in human cancer immunology. Elsevier North Holland Inc. 305-320.

Heimdal J H, Aarstad H J, Olofsson J. 2000. Monocytes secrete Interleukin-6 when co-cultured in vitro with benign or malignant autologous fragment spheroids from squamous cell carcinoma patients. Scand J Immunol 51: 271-278.

Heimdal J H, Aarstad H J, Olsnes C, Olofsson J. 2001. Human autologous monocytes and monocyte-derived macrophages in co-culture with carcinoma F-spheroids secrete IL-6 by a non-CD14-dependent pathway. Scand J Immunol 53: 162-170.

Hellström K E, Hellström I. 1974. Lymphocyte-mediated cytotoxicity and blocking serum activity to tumour antigens. In Dixon F J and Kunkel H G. Eds. Advances in Immunology. Academic Press. 209-277.

Hoyt D, Ozkan N, Ninnemann J, Hansbrough J, Pinney E, Wormsley S. 1988. Trauma peptide induction of lymphocyte changes predictive of sepsis. J Surg Res 45: 342-8.

Huber D, Philipp J, Fontana A. 1992. Protease inhibitors interfere with the transforming growth factor-beta-dependent but not the transforming growth factor-beta-independent pathway of tumour cell-mediates immunosuppression. J Immunol 148:277-84.

Isashi Y, Yamashita T, Nagasawa S, Tanaka K, Murakami M, Uede T. 1998. The mechanism by which proteolysis enhances the ligand-binding activity of guinea pig type II Fc receptor for IgG (FcγRIIB). J Biochem 123: 959-67.

Katayama M, Kamihagi K, Nakagawa K, Akiyama T, Sano Y, Ouchi R, Nagata S, Hino F, Kato I. 1993. Increased fragmentation of urinary fibronectin in cancer patients detected by immunoenzymometric assay using domain-specific monoclonal antibodies. Clinica Chimica Acta 217: 115-128.

Kirkwood J, Vlock D. 1984. Augmentation of autologous antibody to human melanoma following acid dissociation and ultrafiltration of serum. Cancer Res 44: 4177-4182.

Kono K, Salazar-Onfray F, Petersson M, Hansson J, Masucci G, Wasserman K, Nakazawa T, Anderson P, Kiessling R. 1996. Hydrogen peroxide secreted by tumor-derived macrophages down-modulates signal-transducing zeta molecules and inhibits tumor-specific T cell- and natural killer cell-mediated cytotoxicity. Eur J Immunol. 26(6):1308-13.

Lin S-Y, Kinet J-P. 2001. Giving inhibitory receptors a boost. Science 291:445-86.

Lindahl M, Stahlbom B, Svartz J, Tagesson C. 1998. Protein patterns of human nasal and bronchoalveolar lavage fluids analyzed with two-dimensional gel electrophoresis. Electrophoresis 19:3222-9.

Lissoni P, Brivio F, Viviani S, Fumagalli L. 1999. Which immunological parameters are clinically essential to monitor IL-2 cancer immunotherapy? J Biol Regul Homeost Agents 13:110-4.

López-Moratalla N, del Mar Calonge M, López-Zabalza M, Pérez-Mediavilla A, Subirá M, Santiago E. 1995. Activation of human lymphomononuclear cells by peptides derived from extracellular matrix proteins. Biochimica et Biophysica Acta 1265: 181-8.

Ménétrier-Caux C, Bain C, Favrot M C, Duc A, Blay J Y. 1999. Renal cell carcinoma induces interleukin 10 and prostaglandin $E_2$ production by monocytes. Br J Cancer 79: 119-130.

Milas L. 2001. Cyclooxygenase-2 (COX-2) enzyme inhibitors as potential enhancers of tumour radioresponse. Semin Radiat Oncol 11:290-9

Mizutani Y, Bonavida B, Koishihara Y, Akamatsu K, Ohsugi Y, Yoshida O. 1995. Sensitization of human renal cell carcinoma cells to cis-diamminedichloroplatinum (II) by anti-interleukin 6 monoclonal antibody or anti-interleukin 6 receptor monoclonal antibody. Cancer Res 55:590-6.

Mocellin S, Wang E, Marincola F M. 2001. Cytokines and immune response in the tumour microenvironment. J Immunother 24:392-407.

Nikkola J, Vihinen P, Vlaykova T, Hahka-Kemppinen M, Kahari V M, Pyrhonen S. 2001. High collagenase-1 expression correlates with a favourable chemoimmunotherapy response in human metastatic melanoma. Melanoma Res 11:157-66.

North R. 1985. Down-regulation of the antitumor immune response. Advances in Cancer Research 45:1-43.

Otsuji M, Kimura Y, Aoe T, Okamoto Y, Saito T. 1996. Oxidative stress by tumour-derived macrophages suppresses the expression of CD3 zeta chain of T-cell receptor complex and antigen-specific T-cell responses. Proc Natl Acad Sci USA 93:13119-24.

Pawelec G, Heinzel S, Kiessling R, Muller L, Ouyang Q, Zeuthen J. 2000. Escape mechanisms in tumour immunity: a year 2000 update. Crit. Rev Oncog 11:97-133.

Pricop L, Redecha P, Teillaud J-L, Frey J, Fridman W, Sautes-Fridman C, Salmon J. 2001. Differential modulation of stimulatory and inhibitory Fcγ receptors on human moncytes by Th1 and Th2 cytokines. J Immunol 166: 531-7.

Ravetch J V, Bolland S. 2001. IgG Fc receptors. Annu Rev Immunol 19:275-90.

Salih H R, Schmetzer H M, Burke C, Starling G C, Dunn R, Pelka-Fleischer R, Nuessle V, Kiener P A. 2001. Soluble cd137 (4-1bb) ligand is released following leukocyte activation and is found in sera of patients with hematological malignancies. J Immunol 167:4059-66.

Sheu B C, Hsu S M, Ho H N, Lien H C, Huang S C, Lin R H. 2001. A novel role of metalloproteinase in cancer-mediated immunosuppression. Cancer Res 61:237-242.

Sjögren H O, Hellström I, Bansal S C, Hellström K E. 1971. Suggestive evidence that the "blocking antibodies" of tumour-bearing individuals may be antigen-antibody complexes. Proc Nat Acad Sci USA. 68:1372-5.

Sulitzeanu D. 1993. Immunosuppressive factors in human cancer. Adv Cancer Res 60:247-267.

Sutterwala F S, Noel G J, Salgame P, Mosser D M. 1998. Reversal of proinflammatory responses by ligating the macrophage Fcgamma receptor type I. J Exp Med 188: 217-22.

Szabo G, Miller-Graziano C, Wu J H, Takayama T, Kodys K. 1990. Differential tumour necrosis factor production by human monocyte subsets. J Leuk Biol 47:206-216.

Szabo G, Kodys K, Miller-Graziano C. 1991. Elevated monocyte interleukin-6 (IL-6) production in immunosuppressed trauma patients. I. Role of FcγRI cross-linking stimulation. J Clin Immunol 11:326-335.

Takizawa T, Nishinarita S, Kitamura N, Hayakawa J, Kang H, Tomita Y, Mitamura K, Yamagami K, Horie T. 1995. Interaction of the cell-binding is domain of fibronectin with VLA-5 integrin induces monokine production in cultured human monocytes. Clin Exp Immunol 101:376-382.

Tartour E, Blay J Y, Dorval T, Escudier B, Mosseri V, Douillard J Y, Deneux L, Gorin I, Negrier S, Mathiot C, Pouillart P, Fridman W H. 1996. Predictors of clinical response to interleukin-2-based immunotherapy in melanoma patients: a French multiinstitutional study. J Clin Oncol 14:1697-703.

Tilg H, Trehu E, Atkins M B, Dinarello C A, Mier J W. 1994. Interleukin-6 (IL-6) as an anti-inflammatory cytokine: induction of circulating IL-1 receptor antagonist and soluble tumour necrosis factor receptor p55. Blood 83:113-8.

Walther M M, Johnson B, Culley D, Shah R, Weber J, Venzon D, Yang J C, Linehan W M, Rosenberg S A. 1998. Serum interleukin-6 levels in metastatic renal cell carcinoma before treatment with interleukin-2 correlates with paraneoplastic syndromes but not patient survival. J Urol 159: 718-22.

van de Winkel J G J, van Ommen R, Huizing a T W J, de Raad MAHV M, Tuijnman W B, Groenen P J T A, Capel P J A, Koene R A P, Tax W J M. 1989. Proteolysis induces increased binding affinity of the monocyte type II FcR for human IgG. J Immunol 143:571-578.

Vlock D R, Kirkwood J M. 1985. Serial studies of autologous antibody reactivity to melanoma. J Clin Invest. 76: 849-854.

Wolf H M, Hauber I, Guile H, Samstag A, Fischer M B, Ahmad R U, Eibl M M. 1996. Anti-inflammatory properties of human serum IgA: induction of IL-1 receptor antagonist and FcαR (CD89)-mediated down-regulation of tumour necrosis factor-alpha (TNF-α) and IL-6 in human monocytes. Clin Exp Immunol 105:537-43.

Vose B M, Vanky F, Klein E. 1977. Human tumour-lymphocyte interaction in vitro. V. Comparison of the reactivity of tumour-infiltrating blood and lymph-node lymphocytes with autologous tumour cells. Int J Cancer 20:895-902.

FIGURE LEGENDS

FIG. 1 shows melanoma biopsies stained for the expression of IL1Ra. Different patterns are hereby found, viz. A) tumour cells are generally stained with some positive infiltrating mononuclear cells, and B) large numbers of infiltrating cells staining IL-1Ra, tumour cells only faintly positive.

FIG. 3 shows comparison of IL-1Ra production by PBMCs from healthy individuals and melanoma and renal cell carcinoma patients, cultured in A) HSA pre coated wells or B) uncoated wells.

Figure 1:
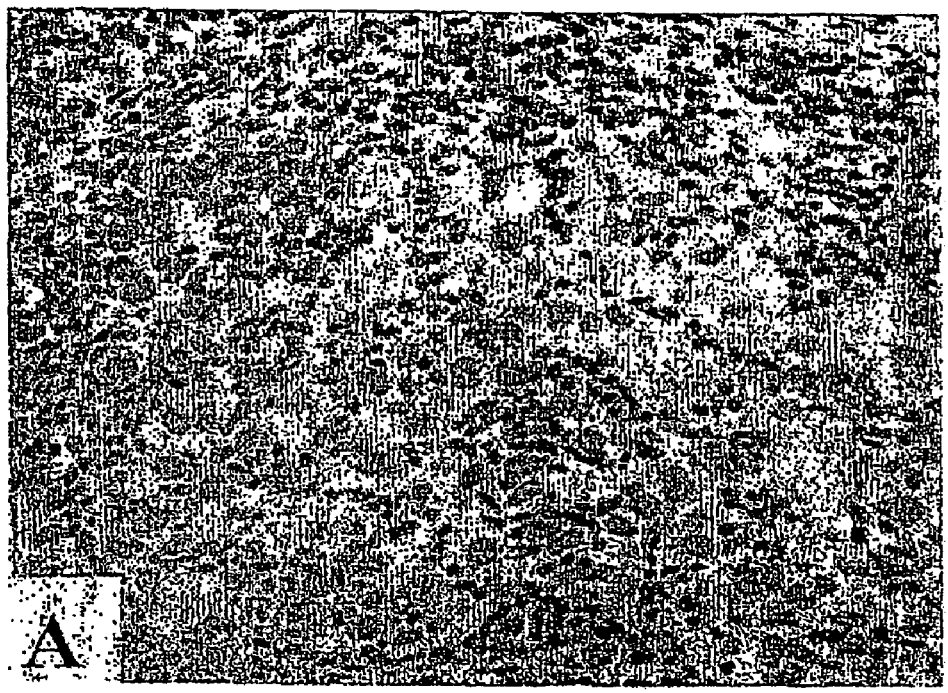
Figure 1:
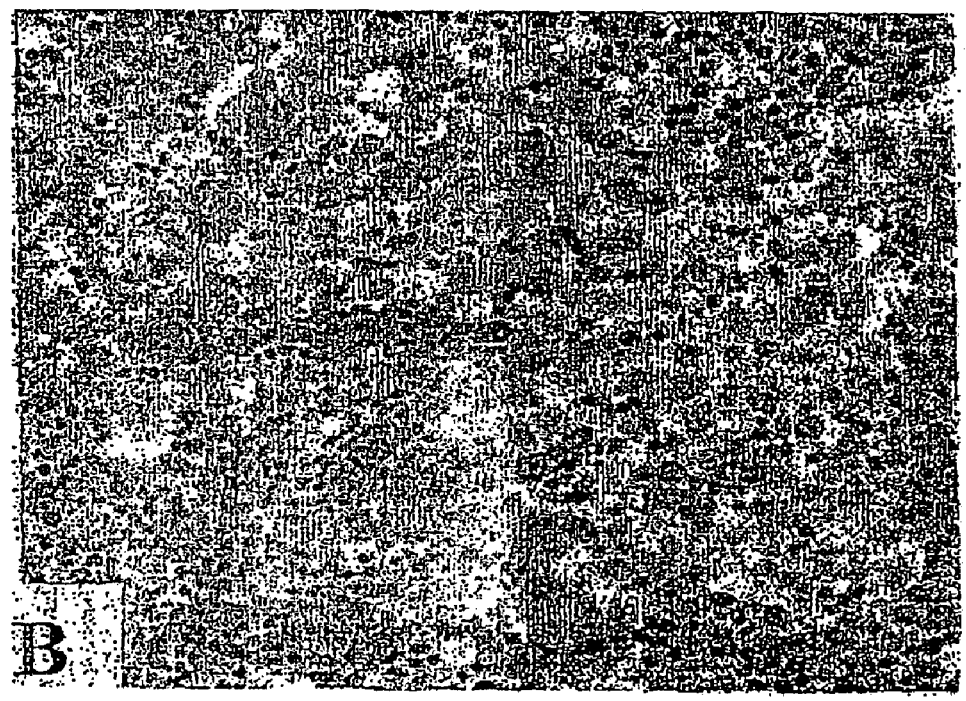
Figure 2:
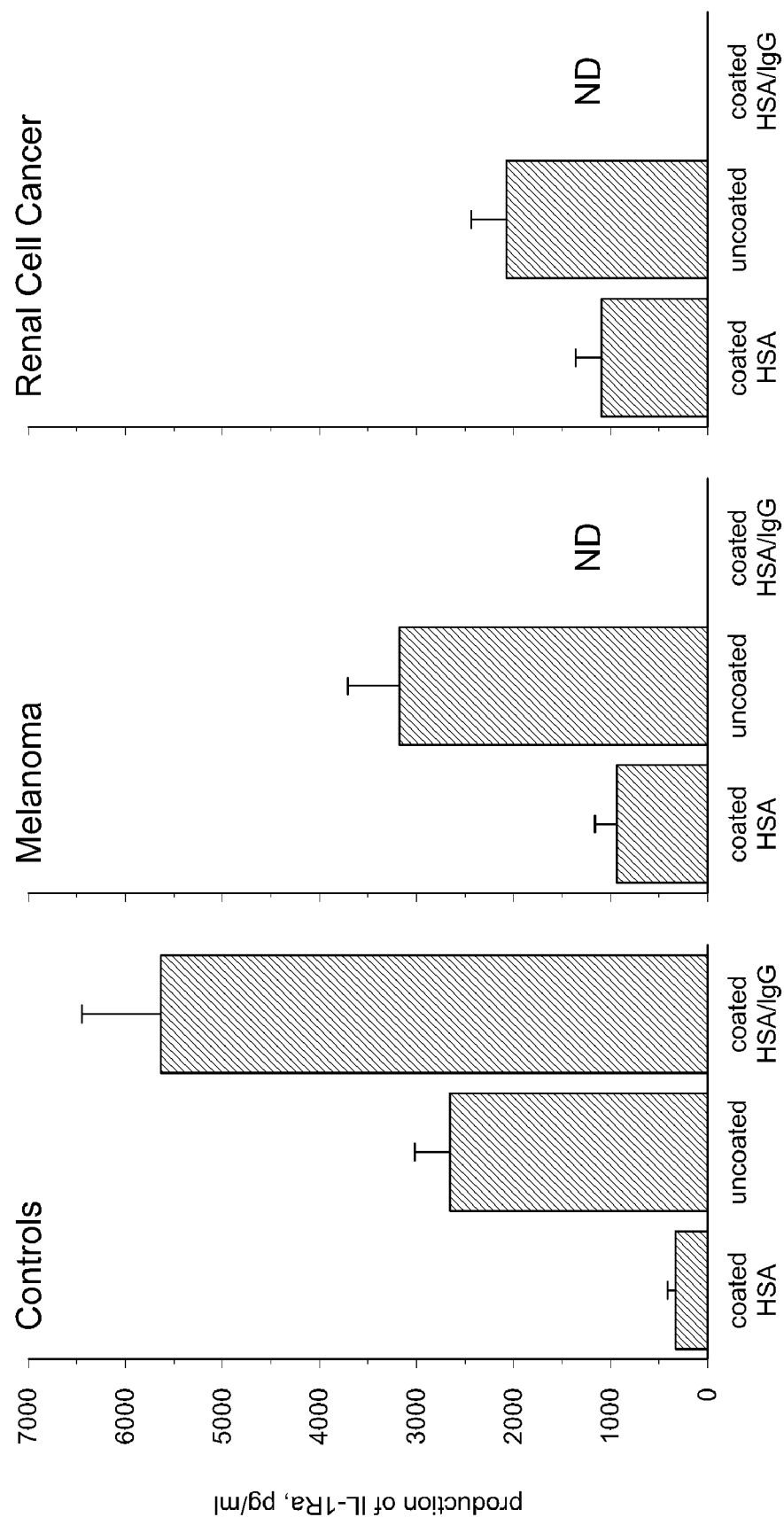
FIG. 2 shows production of IL-1Ra in short term cultures of PBMC from healthy controls and cancer patients. The effect of pre-coating of the culture wells is shown.
Figure 4A:
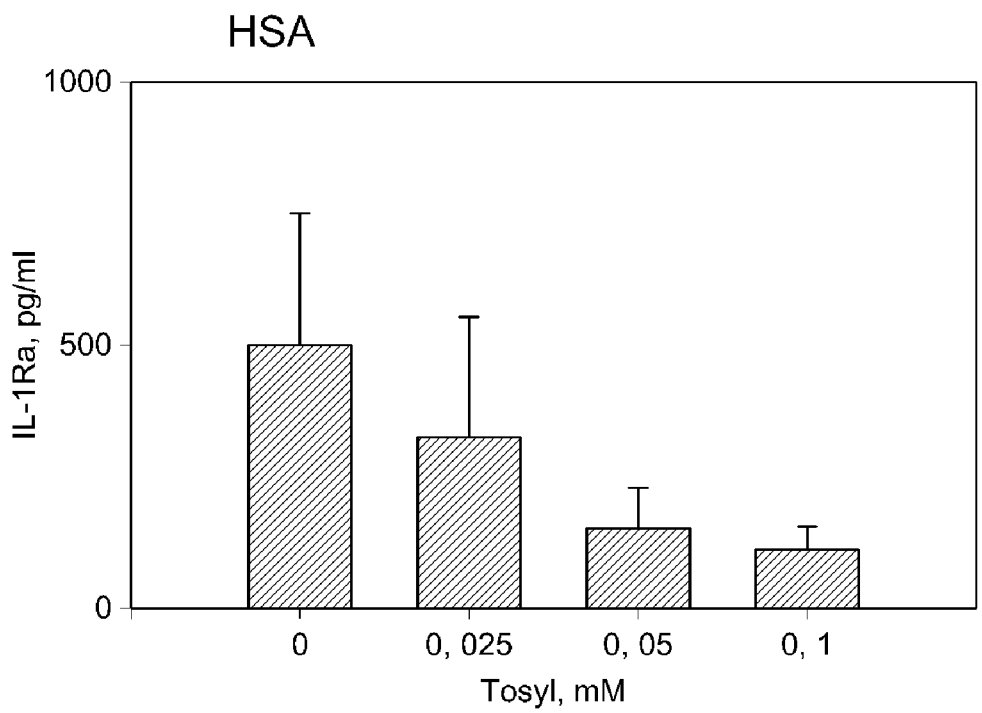
FIG. 4 shows inhibition of IL1Ra production by Tosyl. The effect of Tosyl on IL-1Ra production (mean+/−S.E.) by PBMC from 9 healthy individuals in 10% autologous sera cultured in microtiter plates pre-coated with A) HSA, and B) HSA/IgG.
Figure 4B:
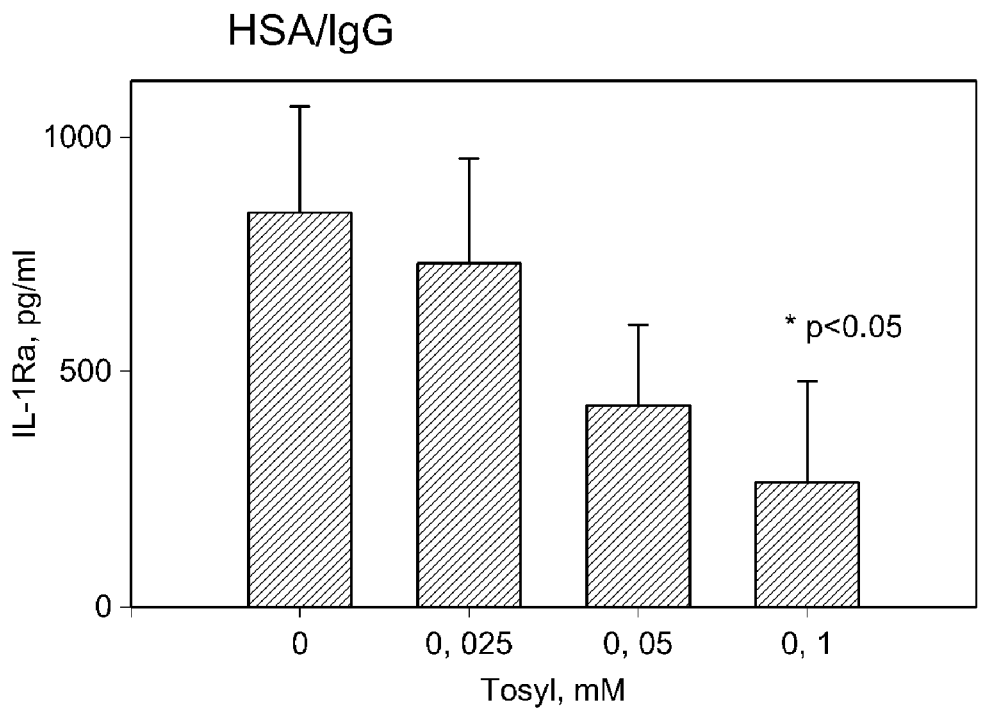
Figure 5:
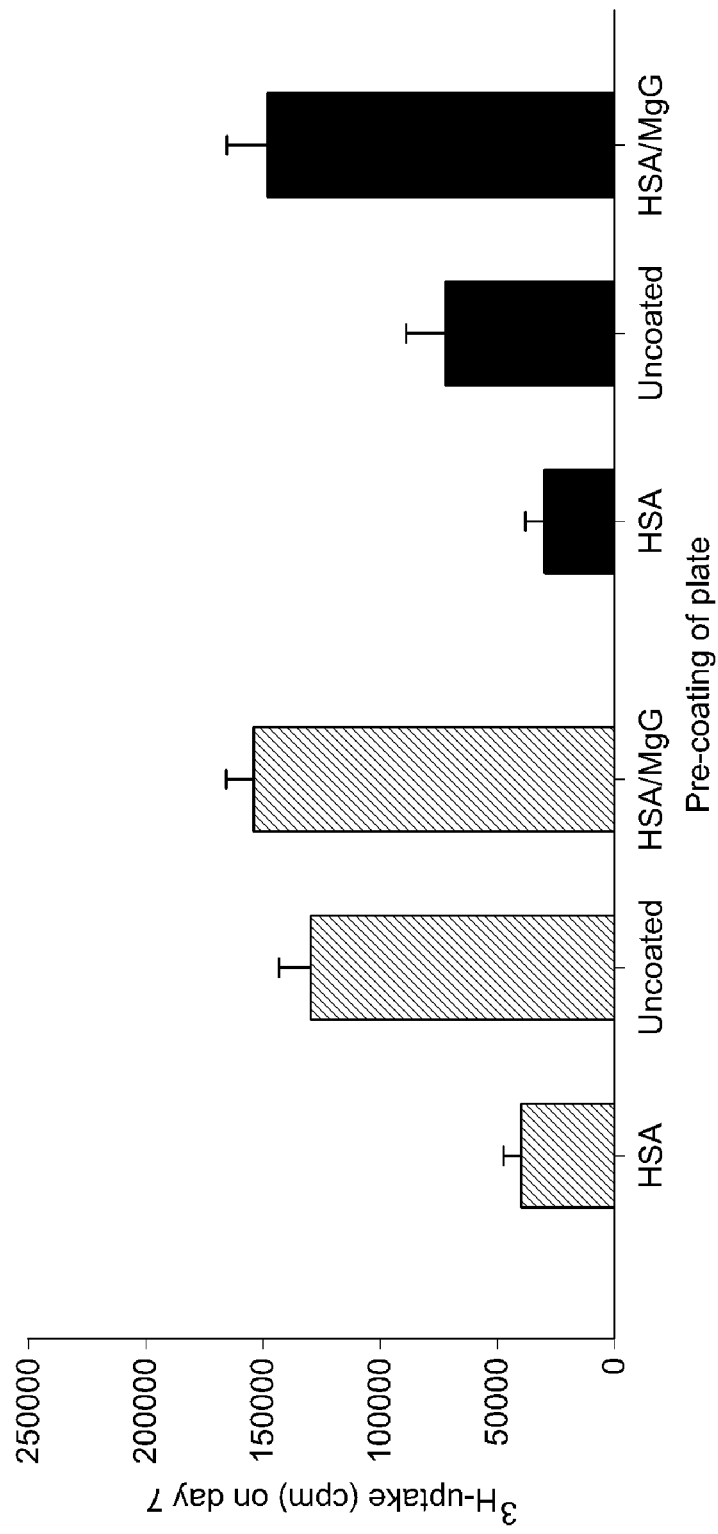

FIG. 5 shows IL-2 induced proliferation in healthy individuals and RCC patients. IL-2 induced proliferation (mean+/−S.D.) by PBMC from normal healthy individuals (grey bars, 21-29 individuals) and PBMC from RCC patients (black bars, 12-18 individuals) cultured in 10% autologous sera on uncoated and pre-coated microtiter plates. Significant (p=0.011) difference in proliferation between PBMC from healthy individuals and RCC patients on uncoated plates, but not on HSA coated or on HSA/IgG coated plates. Significant (p=0.0045) difference in proliferation between PBMC from RCC patients cultured on uncoated and HSA/IgG coated plates.

Figure 6:
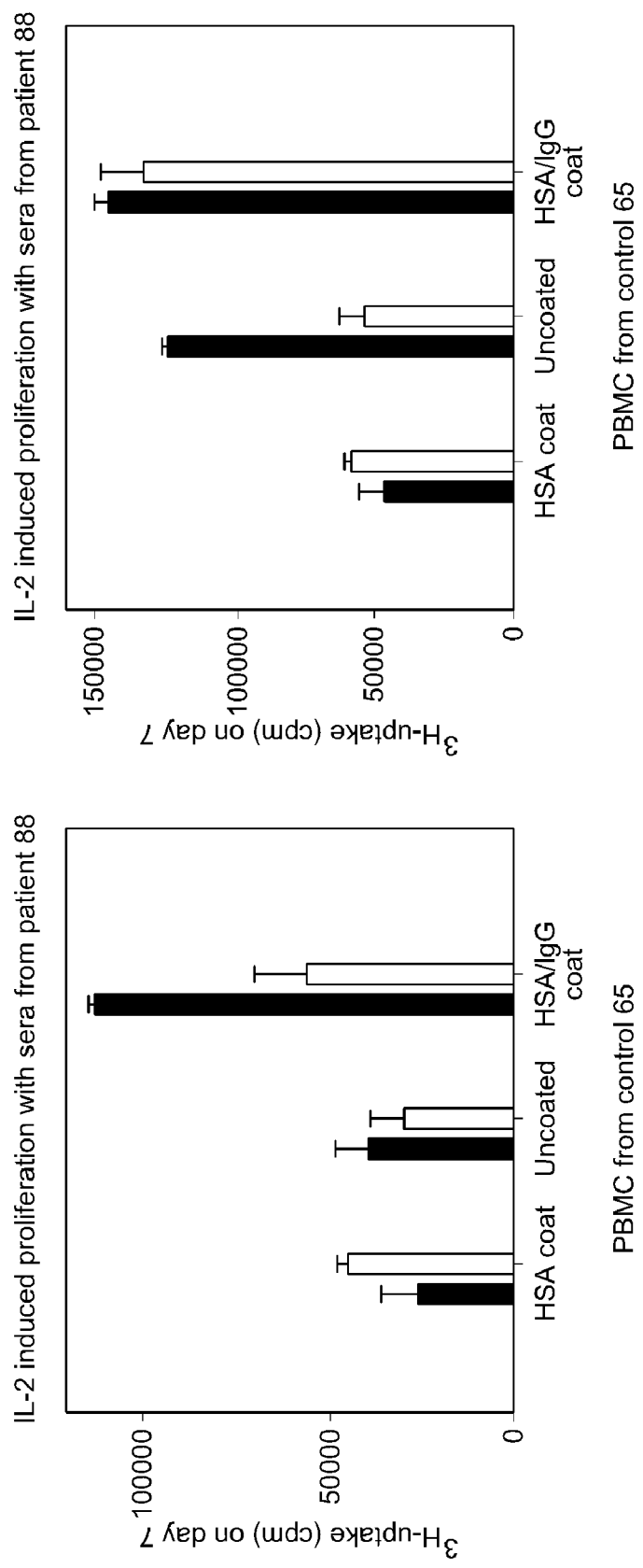
Figure 6B:
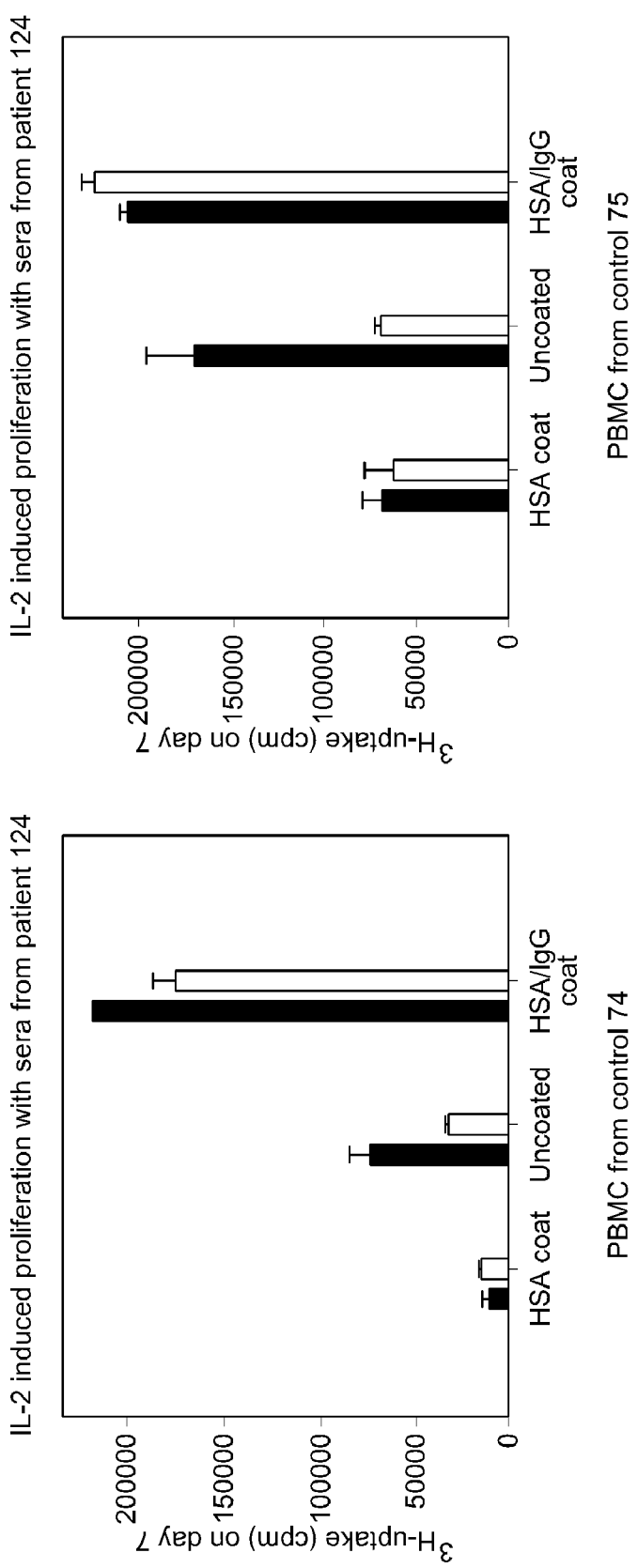
Figure 6C:
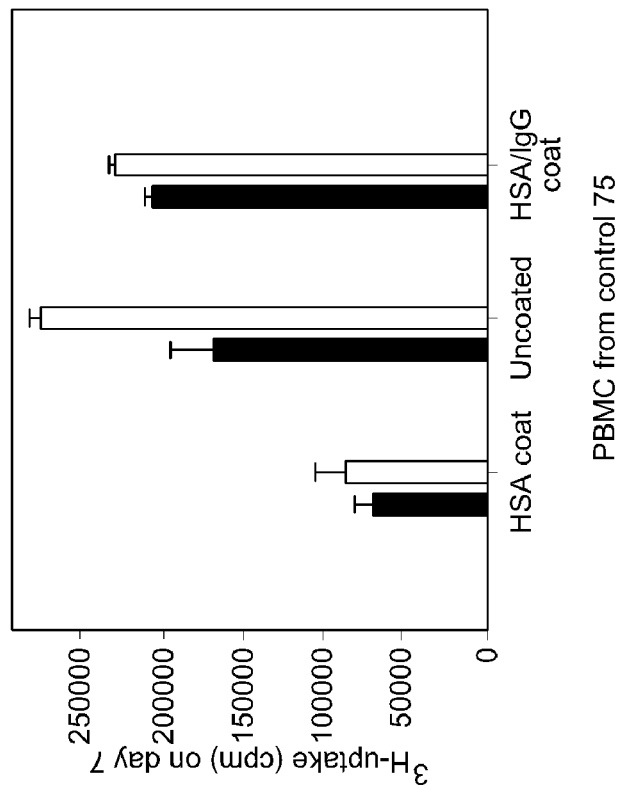
Figure 6C:
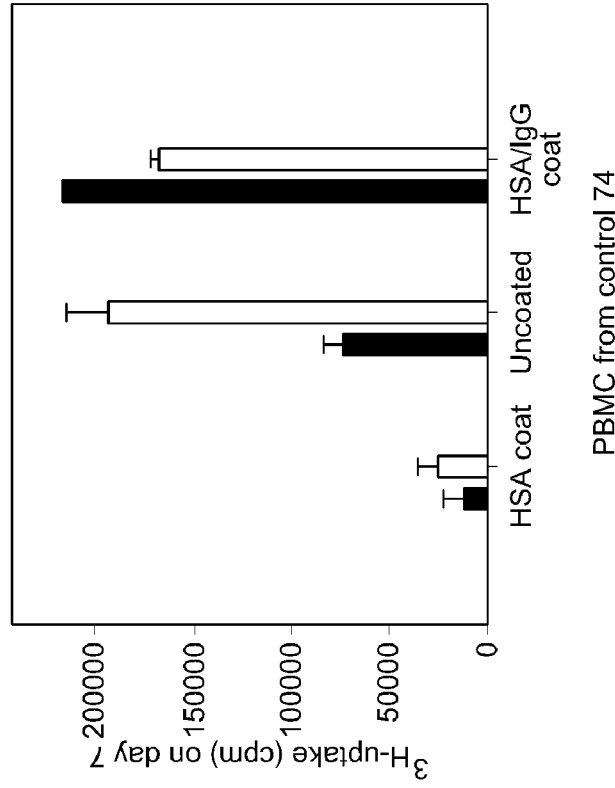

FIG. 6 shows normal PBMC cultured in autologous sera (black bars) or sera from cancer patients (open bars) in the presence of IL-2. Proliferation was measured by 3H-uptake on day 7. Patients 88 and 124 had previously been shown to induce high levels of IL-6 production, whereas patient 112 did not.

Figure 7:
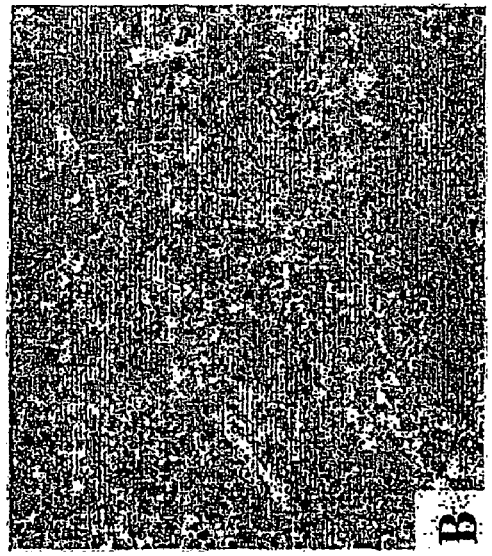
Figure 7:
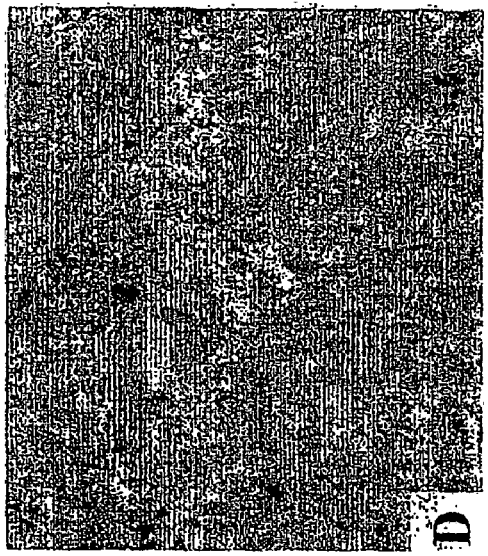
Figure 7:
Figure 7:

FIG. 7 shows tumour biopsies stained for the presence of tissue bound IgG/IC and T-lymphocytes using a double staining technique with recombinant protein G (not binding to albumin). Different staining patterns are shown, viz. A) staining of vascular areas/endothelial cells and some lymphocytes for IgG. Some lymphocytes are not stained for IgG/IC. Low numbers of tumour infiltrating mononuclear cells, B) a diffuse staining of the tumour tissue for IgG/IC, whereby the majority of the lymphocytes are not stained for IgG/IC, C) staining tumour infiltrating macrophages and some lymphocytes for IgG/IC, but tumour cells are generally negative, D) extensive staining of vascular areas for IgG/IC with very low numbers of infiltrating mononuclear cells.

Figure 8:
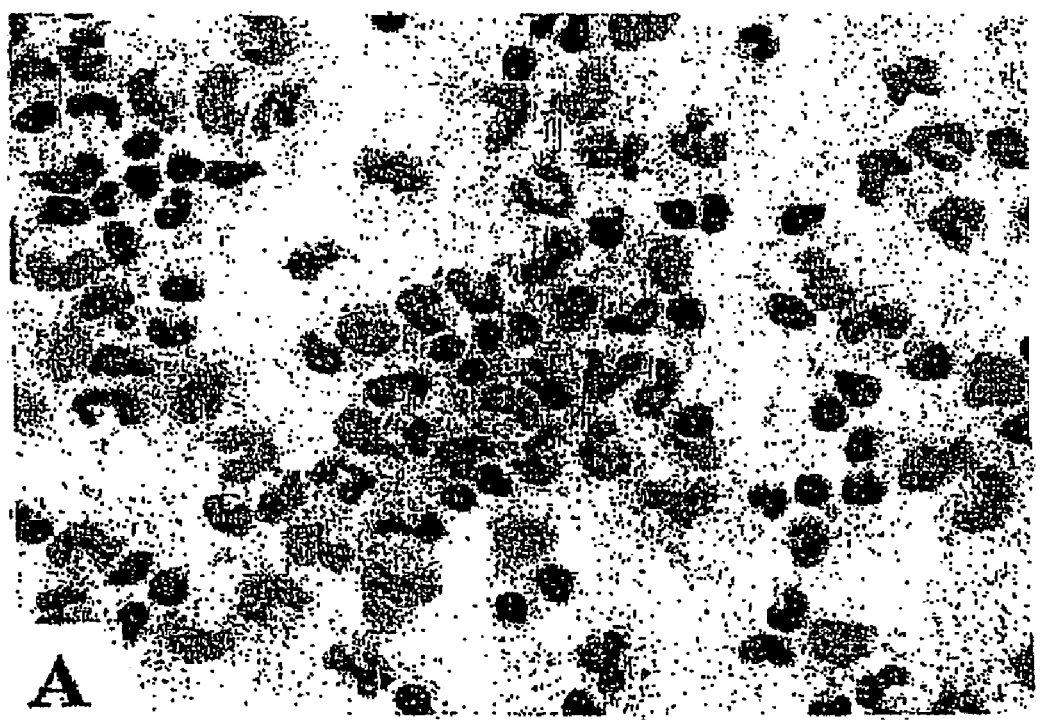
Figure 8:
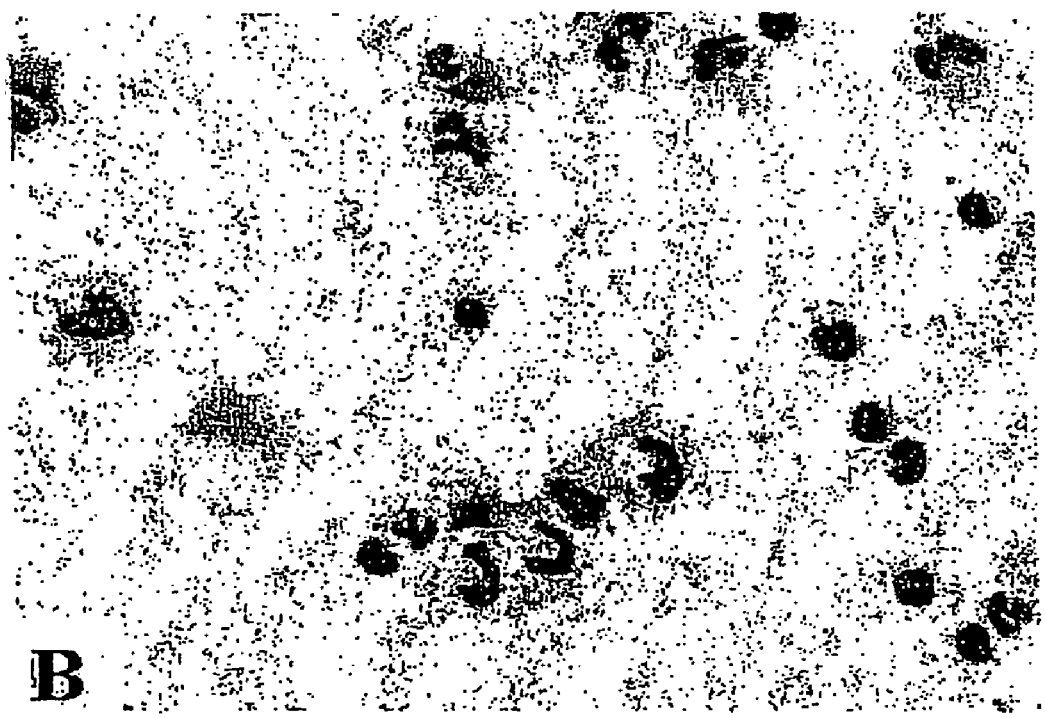

FIG. 8 shows cytospins of PBMC from two patients with malignant melanoma stained for the presence of IgG/IC, using recombinant is protein-G (A) or monoclonal directed against the Fc-part of IgG.

Figure 9:
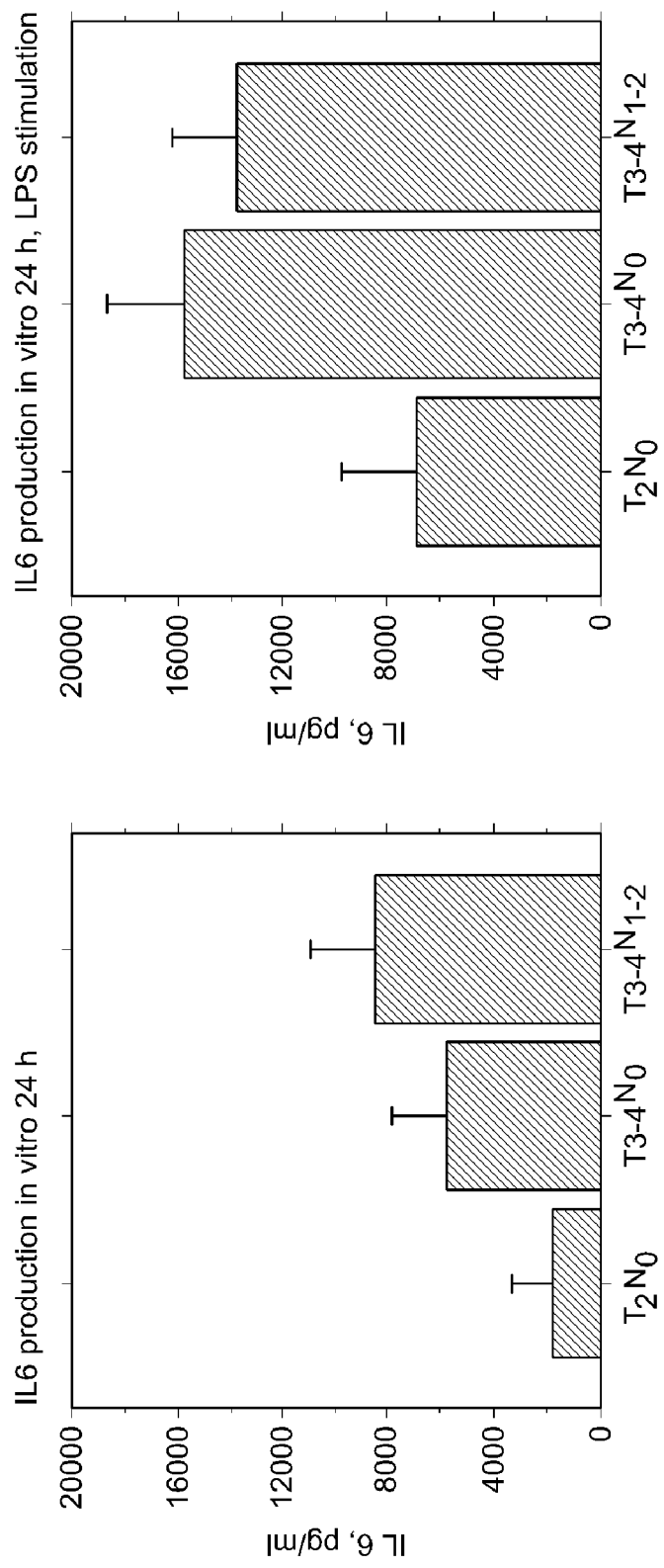

FIG. 9 shows IL-6 production by PBMCs from different subsets of colorectal cancer patients. A) without LPS stimulation and B) with LPS-stimulation.

Figure 10:
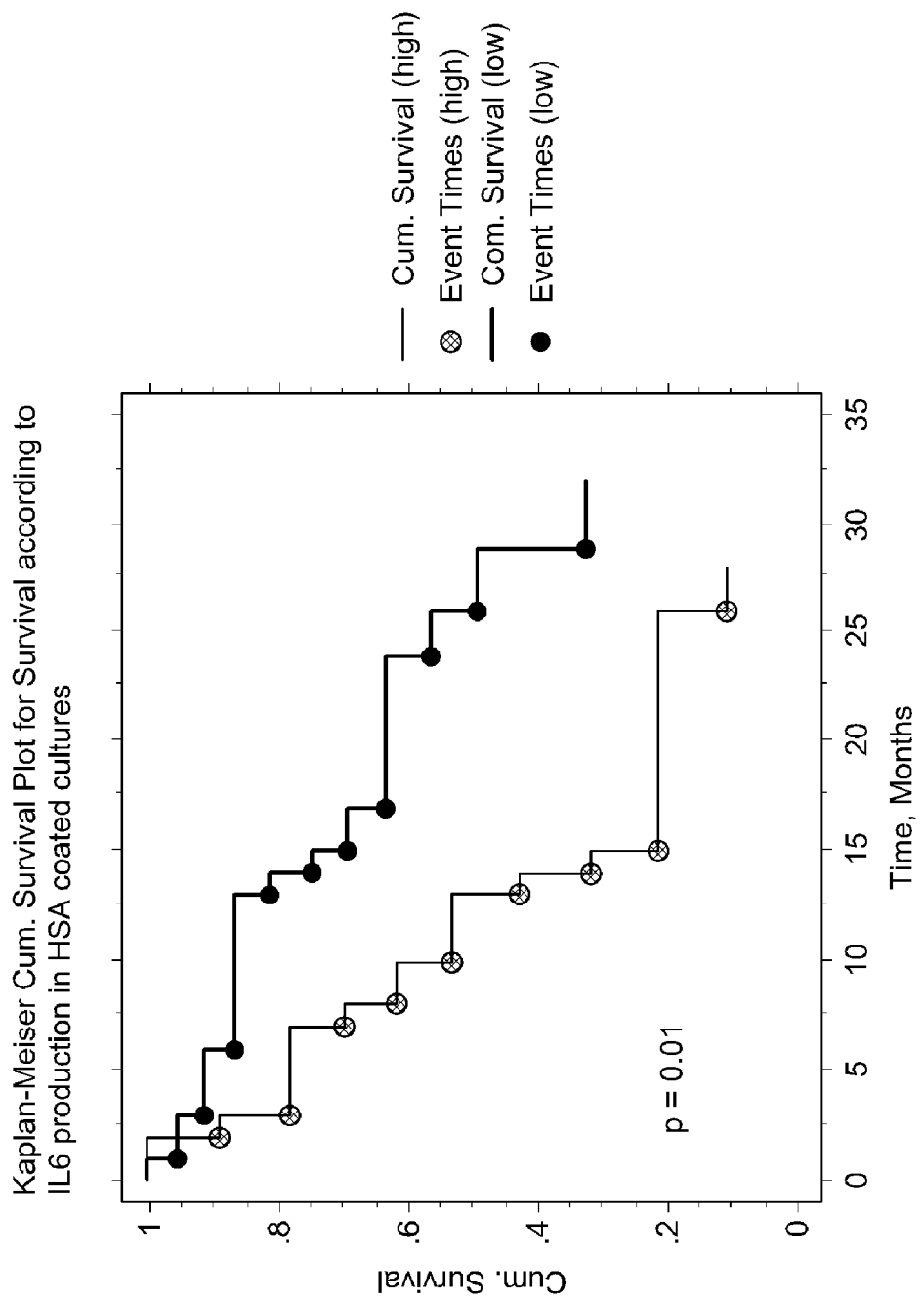

FIG. 10 shows survival in renal cell carcinoma patients according to IL-6 production by PBMCs in short term cultures where the microtitre plates were coated with HSA. High production is >2500 μg/ml.

Figure 11:
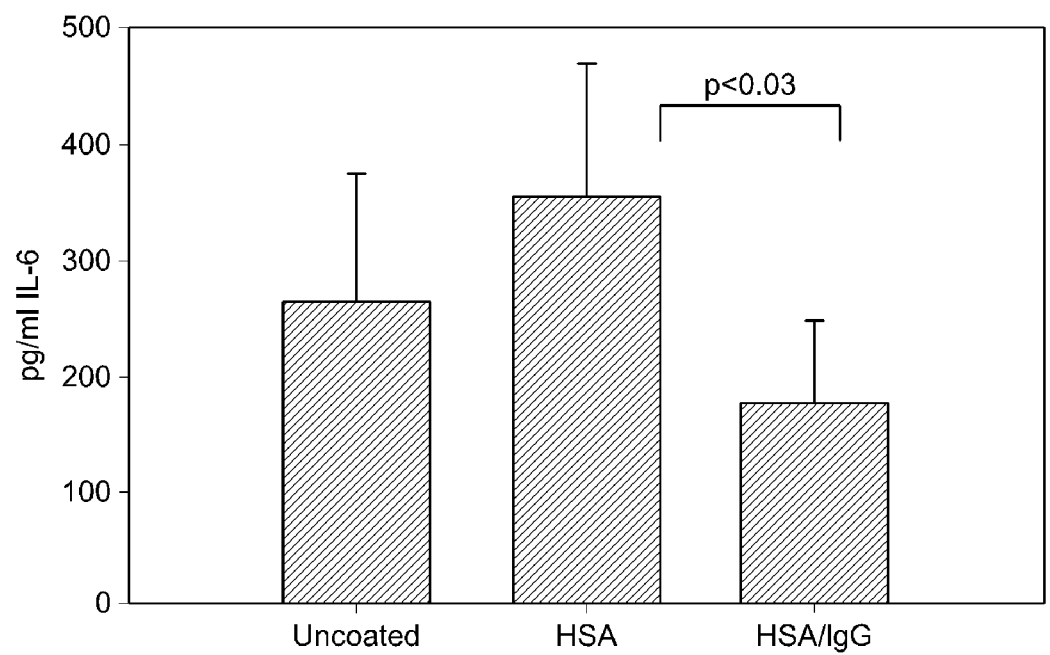

FIG. 11 shows inhibition of IL-6 production by IgG. Production of IL-6 by control PBMCs after culture on uncoated tissue culture wells (n=37), HSA-coated (n=37), or wells coated with HSA/IgG (n=36).

Figure 12:
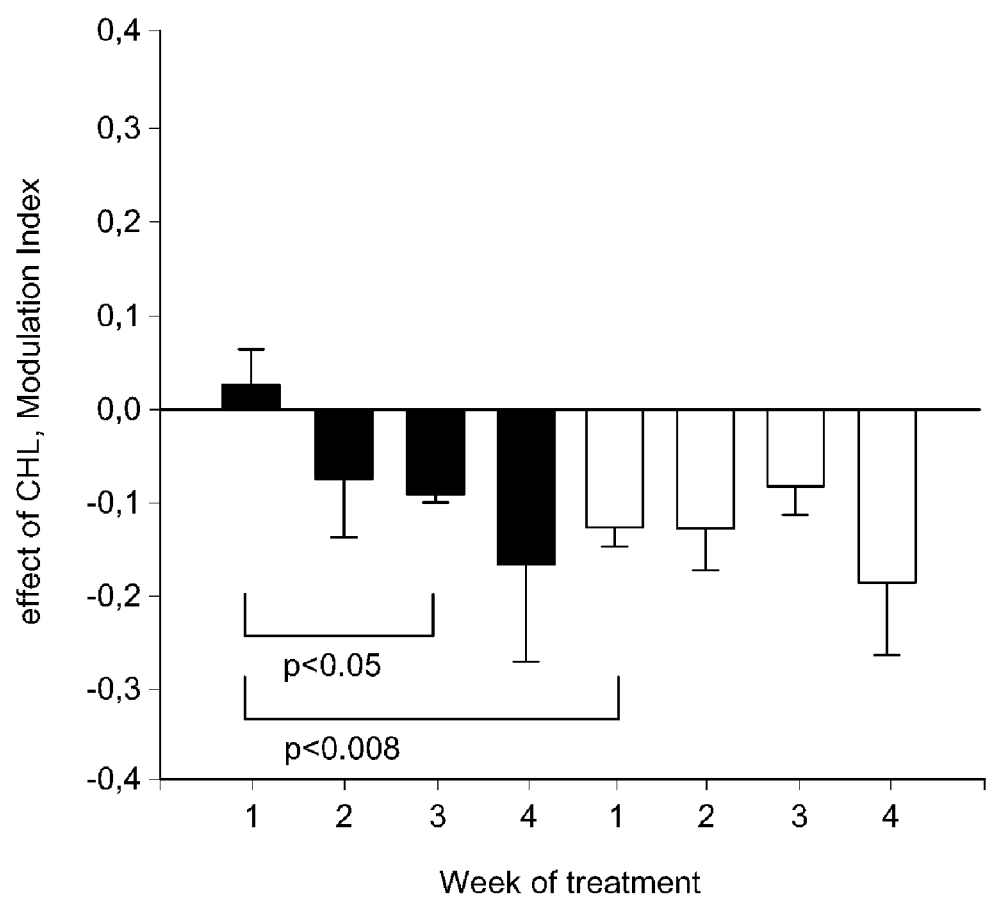

FIG. 12 shows the effect of chlorambucil on PHA-induced proliferation of PBL from RCC patients before treatment with IL-2. Modulation Index (MI) was calculated as described under Materials and Methods. The assays were performed at the following time points: 1) before start of treatment, 2) one week later, 48 hours after five days of IL-2 treatment, 3) after one week without IL-2 administration and 4) after an additional week, 48 hours after another five days of IL-2 treatment combined with chlorambucil.

Figure 13:
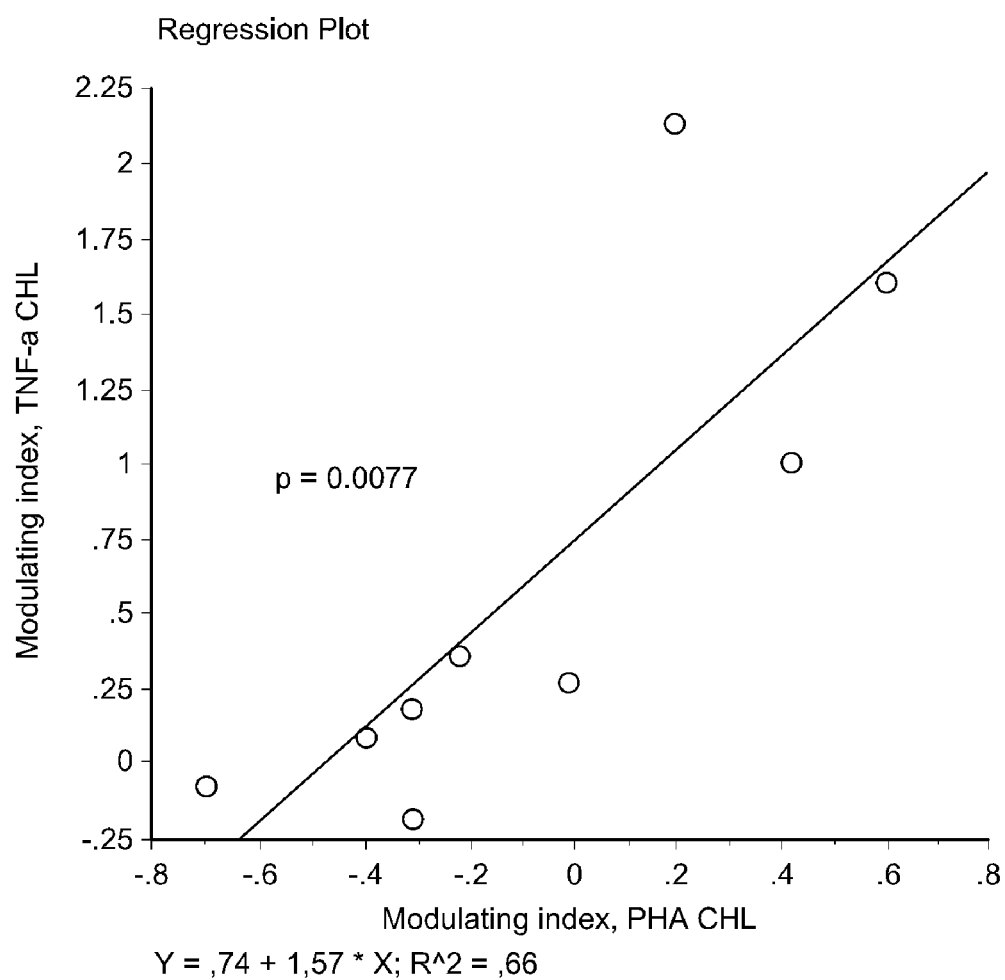

FIG. 13 shows the effect of chlorambucil (CHL) on TNF-α production and proliferation of PHA-stimulated PBMC from RCC patients. PBMC were cultured with PHA in the presence or absence of CHL for 72 hours and the cellular $^3$H-uptake and the TN-α concentration in cell-free culture supernatants were assessed. Modulation Index was calculated as described under Materials and Methods. Each circle represents one patient.

Figure 14:
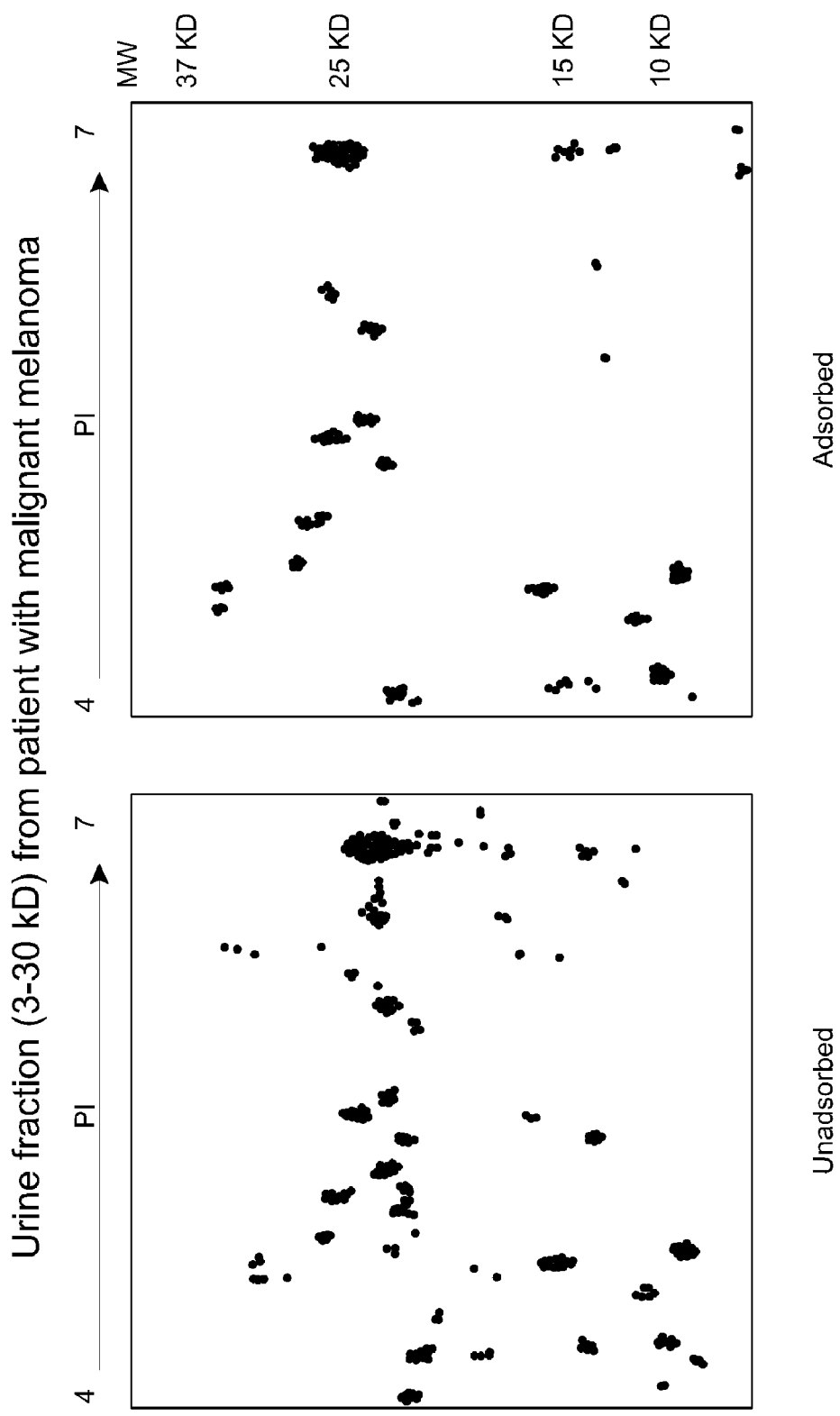

FIG. 14. 2D gel electrophoresis of PBMC-adsorbed and unadsorbed urine fractions pooled from two patients with renal cell carcinoma. 230 ug of protein was loaded per 2D gel. Separated proteins (based on isoelectric focusing in the first dimension and molecular mass in the second dimension) were detected by SYPRO Ruby staining.

Figure 15:
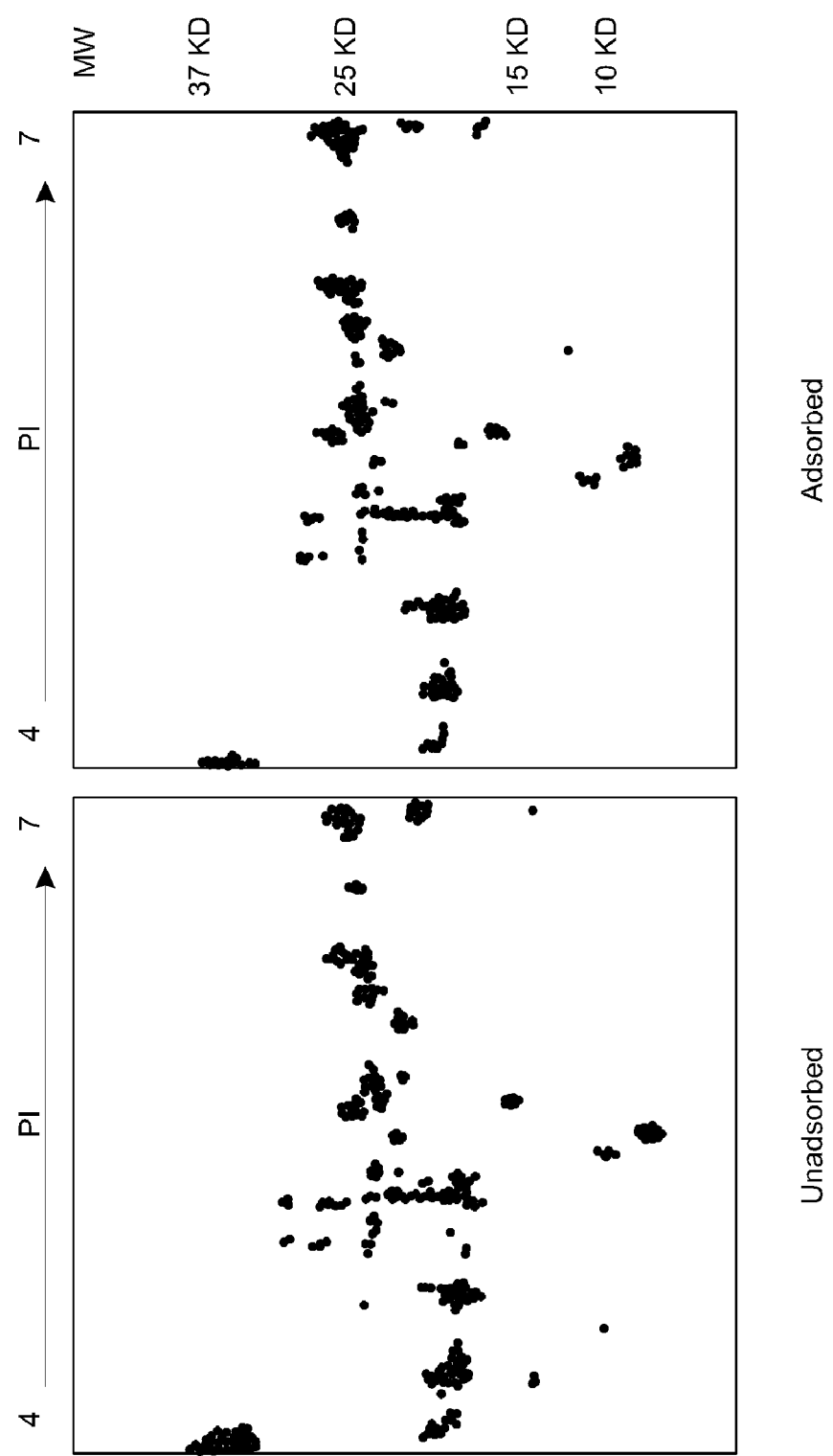

FIG. 15. 2D gel electrophoresis of PBMC-adsorbed and unadsorbed urine fractions from a patient with malignant melanoma. 350 ug of protein was loaded per 2D gel. Separated proteins (based on isoelectric focusing in the first dimension and molecular mass in the second dimension) were detected by SYPRO Ruby staining.

Figure 16:
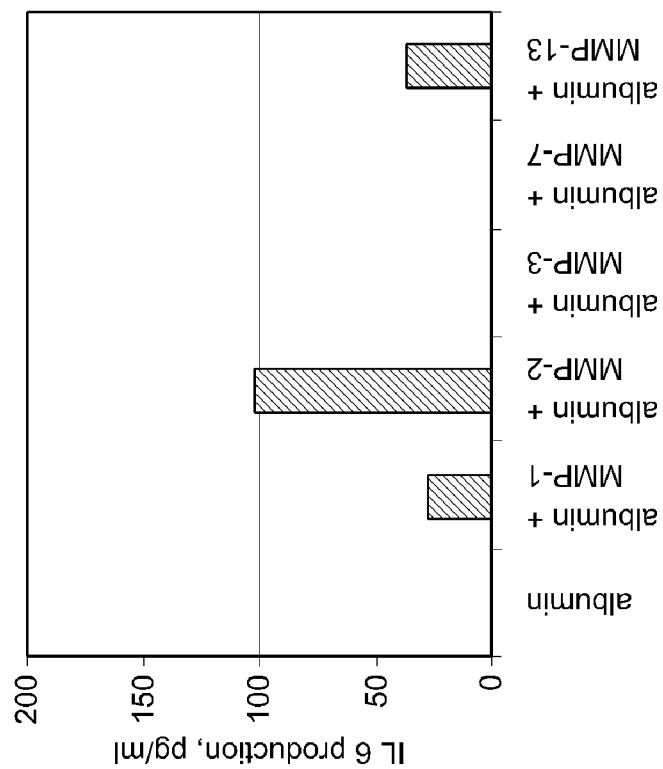
Figure 16:
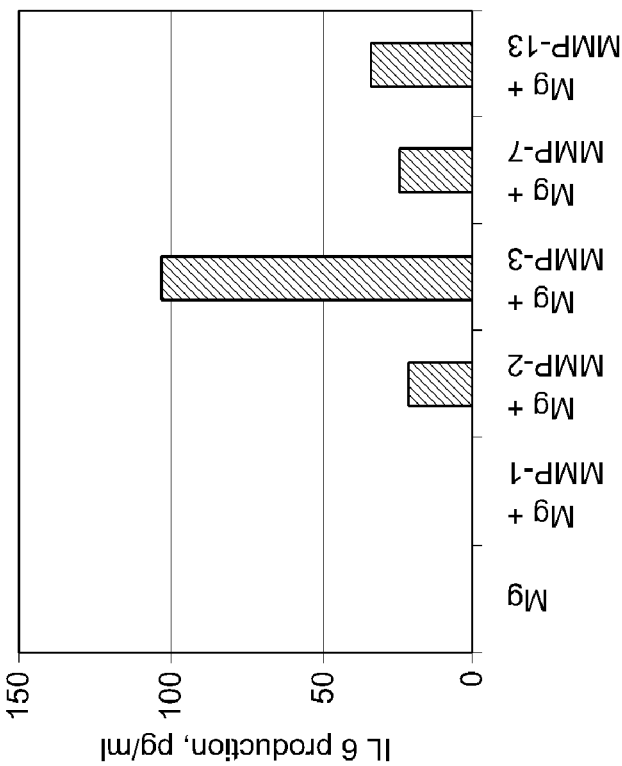
Figure 16B:
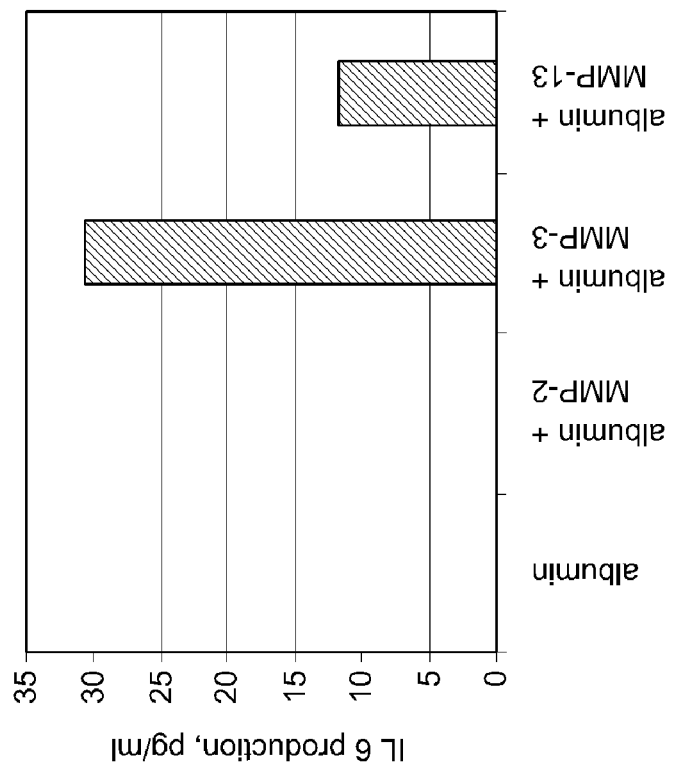
Figure 16B:
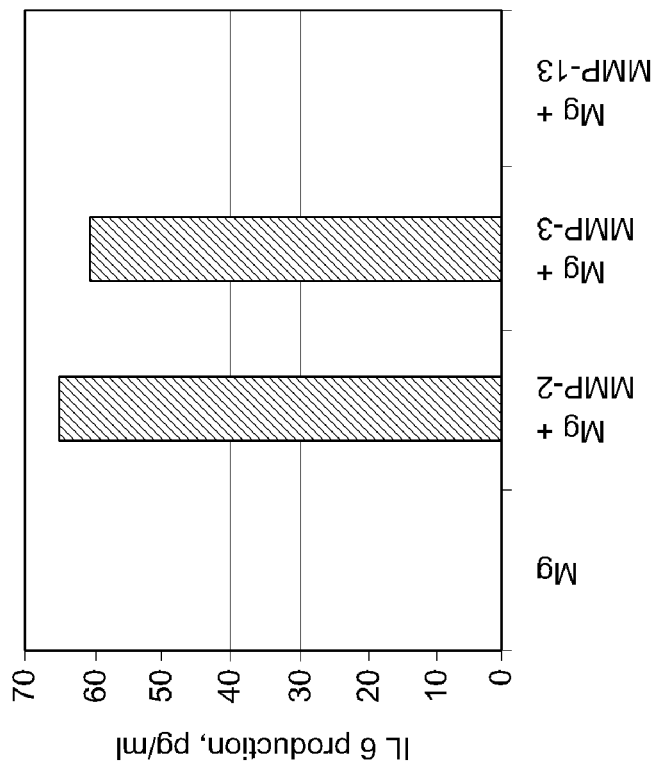

FIG. 16. Generation of IL-6 inducing factors by incubation of IgG (A and C) and albumin (B and D) with MMPs. Two experiments using different buffer systems are shown (as described in Material and Methods). The substrates were incubated with MMPs for 20 hours in experiments A, B, C and for 5 hours in experiment D. The production of IL-6 was then tested in cultures of PBMCs from healthy controls.

Figure 17:
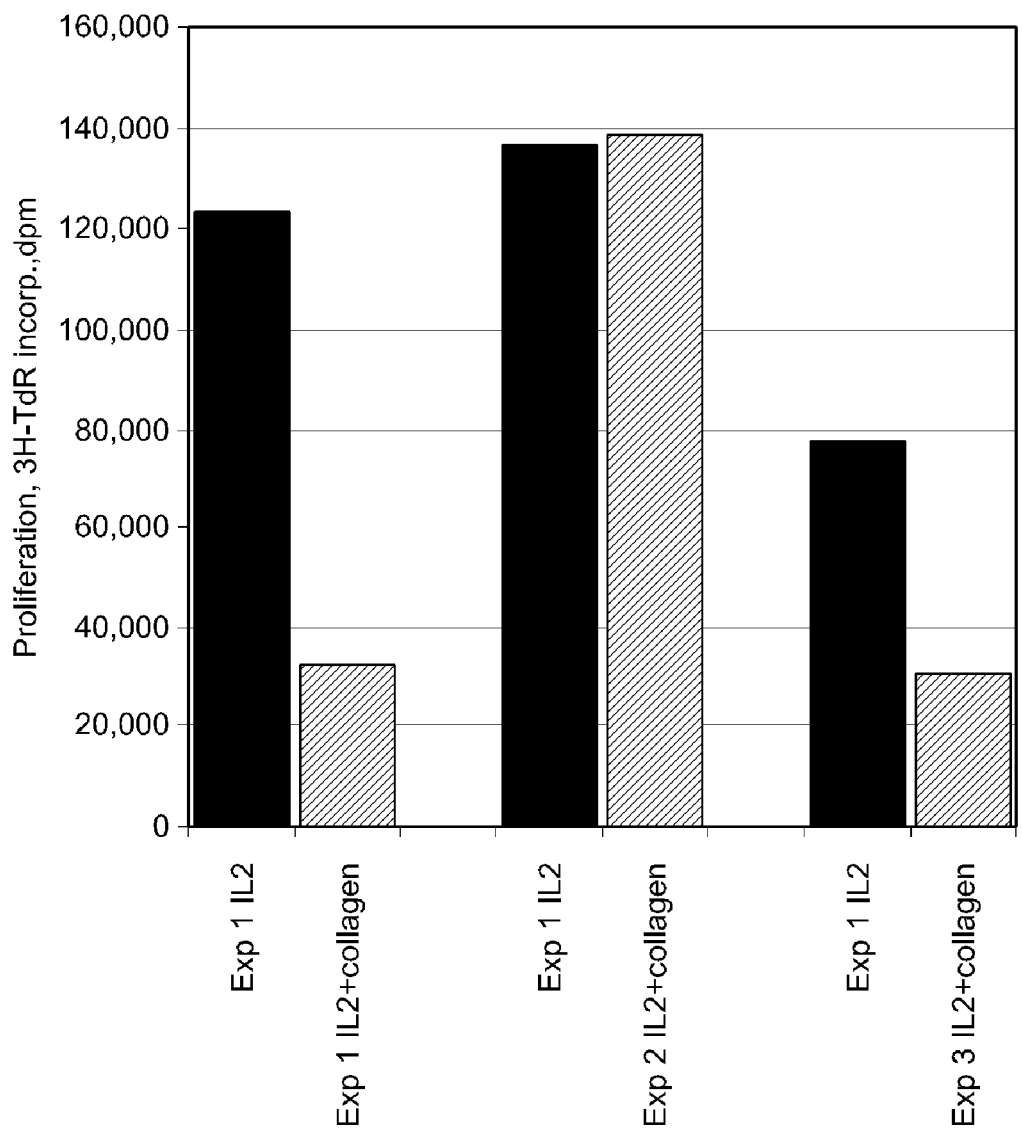

FIG. 17. Effect of collagen/collagen fragments on the proliferative response (measured as incorporation of $^3$H-TdR) of normal PBMCs to IL-2. As can be seen a strong inhibitory effect was demonstrated in two out of three experiments.

Figure 18A:
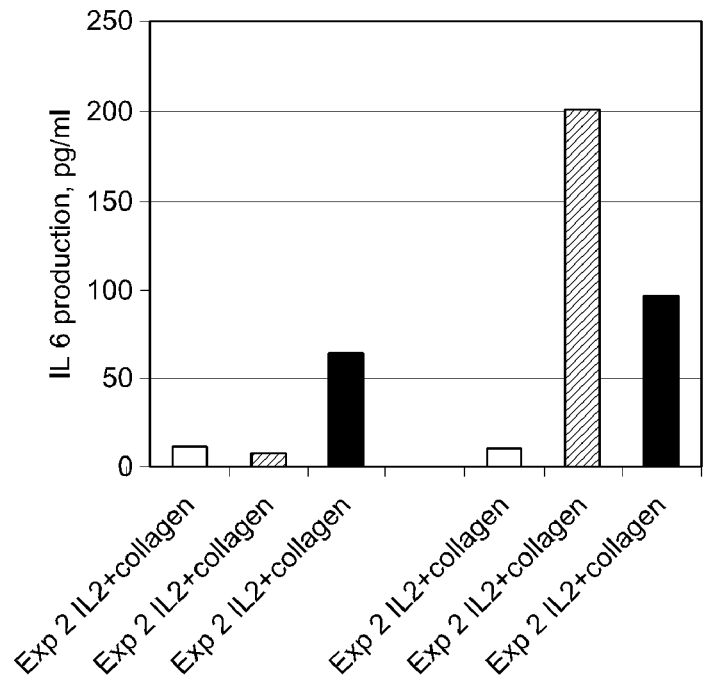
Figure 18B:
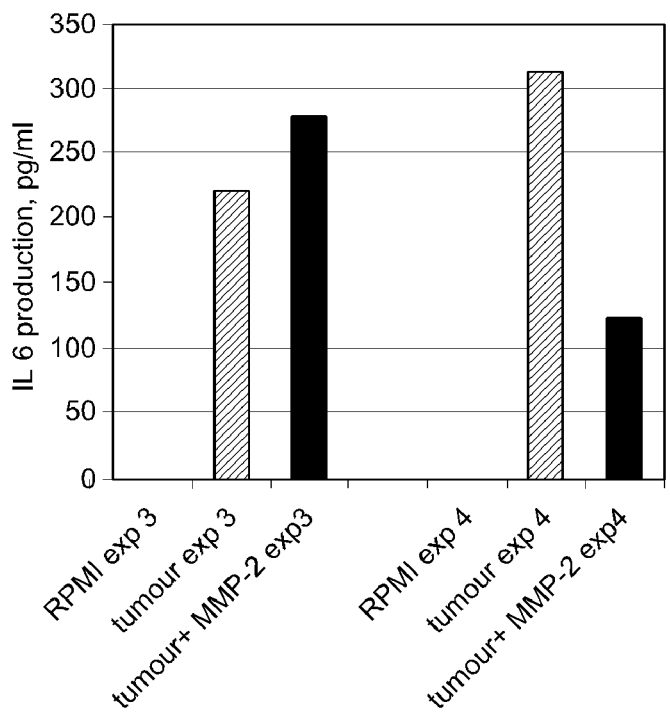

FIG. 18. Modulation of IL-6 inducing factors by incubation of homogenised, washed tumour tissue with MMP-2. A and B represent two separate experiments with two different tumour tissues in each. The effect of this enzyme varies, dependent on the intra-tumoural milieu of different tumours, but it is clearly shown that MMP-2 has a modulatory effect on the production of IL-6 inducing factor/activity, which was tested in cultures of PBMCs from healthy controls.

Figure 19A:
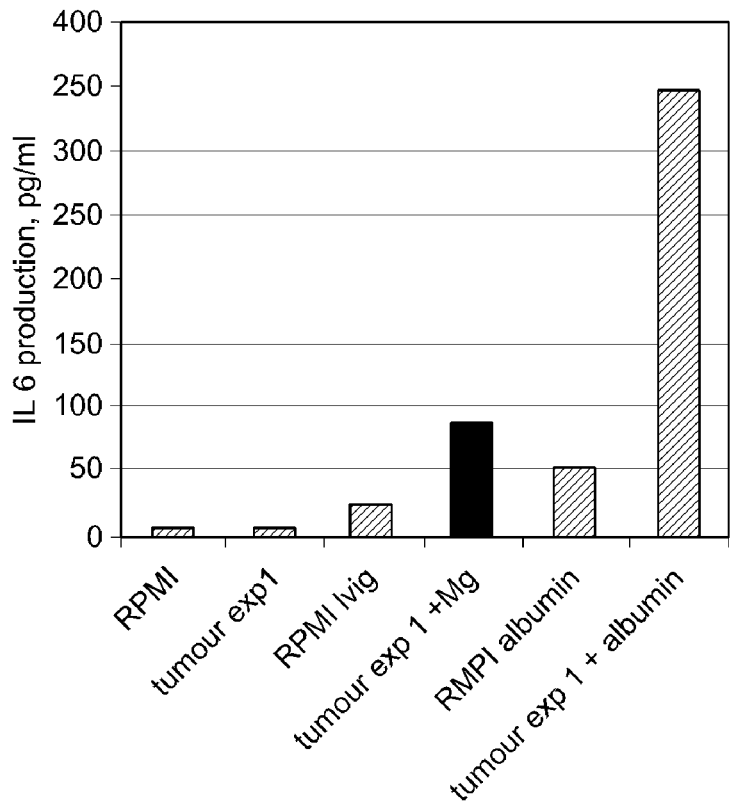
Figure 19B:
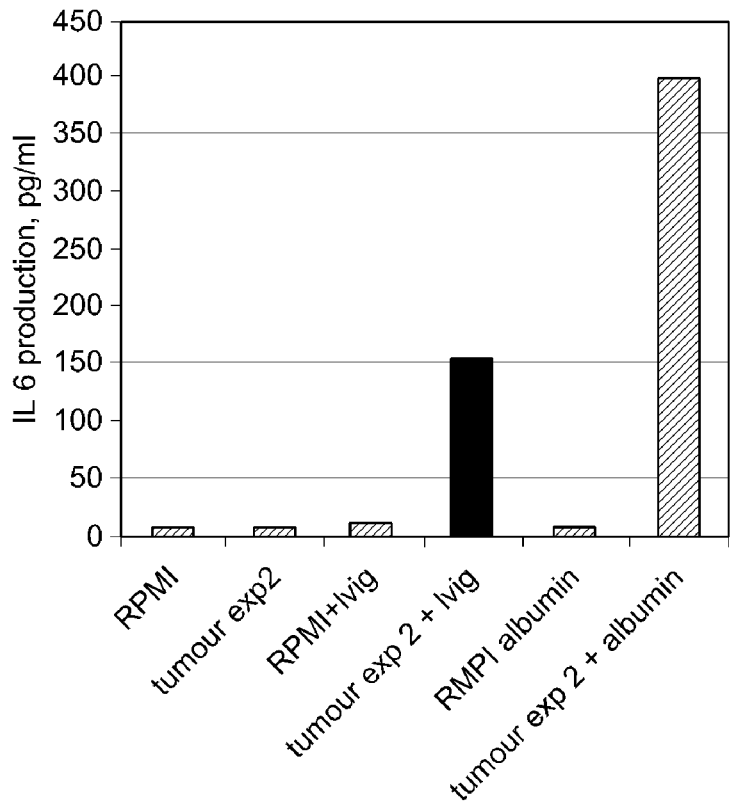

FIG. 19. Generation of IL-6 inducing factors/activity by incubation of IgG and albumin with homogenised, washed tumour tissue. A and B represent two separate experiments. As shown in these two experiments adding IgG and in particular albumin to tumour tissue markedly increases the production of IL-6 inducing factor/activity, which was tested in cultures of PBMCs from healthy controls.

The invention claimed is:

1. A method for identifying a human albumin fragment that induces IL-6 production by human immune cells comprising:
    contacting an isolated human albumin fragment with isolated human immune cells;
    measuring the amount of IL-6 produced by said isolated human immune cells in response to contact with said isolated human albumin fragment; and
    classifying said isolated human albumin fragment as a human albumin fragment that induces IL-6 production when the amount of IL-6 produced by said isolated human immune cells is increased in response to contact with said isolated human albumin fragment.

2. The method of claim 1, wherein said human immune cells are peripheral blood mononuclear cells (PBMCs).

3. The method of claim 1, further comprising detecting the presence of an albumin fragment bound to the human immune cells.

4. The method of claim 2, further comprising detecting the presence of an albumin fragment bound to the PBMCs.

5. The method of claim 1, further comprising detecting the production of IL-10, TNF-α, or IL-1β by said human immune cells.

6. The method of claim 2, further comprising detecting the production of IL-10, TNF-α, or IL-1β by said PBMCs.

7. The method of claim 3, further comprising detecting the production of IL-10, TNF-α, or IL-1β by said human immune cells.

8. The method of claim 4, further comprising detecting the production of IL-10, TNF-α, or IL-1β by said PBMCs.

* * * * *